US011149069B2

(12) United States Patent
Sodroski et al.

(10) Patent No.: US 11,149,069 B2
(45) Date of Patent: Oct. 19, 2021

(54) COMPOSITIONS AND METHODS FOR CONFORMATIONALLY STABILIZING PRIMATE IMMUNODEFICIENCY VIRUS ENVELOPE GLYCOPROTEIN TRIMERS

(71) Applicant: Dana-Farber Cancer Institute, Inc., Boston, MA (US)

(72) Inventors: Joseph Sodroski, Medford, MA (US); Youdong Mao, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1520 days.

(21) Appl. No.: 14/418,544

(22) PCT Filed: Jul. 31, 2013

(86) PCT No.: PCT/US2013/052855
§ 371 (c)(1),
(2) Date: Oct. 20, 2015

(87) PCT Pub. No.: WO2014/022475
PCT Pub. Date: Feb. 6, 2014

(65) Prior Publication Data
US 2015/0183836 A1 Jul. 2, 2015

Related U.S. Application Data

(60) Provisional application No. 61/742,139, filed on Aug. 3, 2012.

(51) Int. Cl.
*A61K 39/21* (2006.01)
*C07K 14/005* (2006.01)
(Continued)

(52) U.S. Cl.
CPC ............ *C07K 14/005* (2013.01); *A61K 39/12* (2013.01); *A61K 39/21* (2013.01); *C07K 16/1063* (2013.01); *C12N 7/00* (2013.01); *A61K 2039/545* (2013.01); *A61K 2039/555* (2013.01); *C07K 2317/14* (2013.01);
(Continued)

(58) Field of Classification Search
None
See application file for complete search history.

(56) References Cited

U.S. PATENT DOCUMENTS 7,939,083 B2 * 5/2011 Dey ........................ A61K 39/21
424/188.1
2009/0191235 A1 7/2009 Kwong et al.
(Continued)

FOREIGN PATENT DOCUMENTS

| WO | WO-2004/053100 A2 | 6/2004 |
| WO | WO-2011/023705 A1 | 3/2011 |
| WO | WO-2012/003234 A2 | 1/2012 |

OTHER PUBLICATIONS

Kim et al., "HIV Vaccines—Lessons learned and the way forward," Curr Opin HIV AIDS 5(5): 428-434 (Year: 2010).*
(Continued)

*Primary Examiner* — M Franco G Salvoza
(74) *Attorney, Agent, or Firm* — Foley Hoag LLP

(57) ABSTRACT

The invention provides compositions and methods related to conformationally stabilizing primate immunodeficiency virus envelope glycoprotein trimers.

7 Claims, 17 Drawing Sheets

Specification includes a Sequence Listing.

(51) Int. Cl.
*A61K 39/12* (2006.01)
*C07K 16/10* (2006.01)
*C12N 7/00* (2006.01)
*A61K 39/00* (2006.01)

(52) U.S. Cl.
CPC ...... *C07K 2317/76* (2013.01); *C07K 2319/35* (2013.01); *C12N 2740/15022* (2013.01); *C12N 2740/16022* (2013.01); *C12N 2740/16122* (2013.01)

(56) References Cited

U.S. PATENT DOCUMENTS

2011/0250220 A1  10/2011  Dey et al.
2012/0045472 A1   2/2012  Harrison et al.

OTHER PUBLICATIONS

Pejchal et al., "Structure-based vaccine in HIV: blind men and the elephant?" Curr Pharm Des 16(33): 3744-3753 (Year: 2010).*
Kumar et al., "Targeting a Neutralizing Epitope of HIV Envelope Gp120 by Immune Complex Vaccine," J AIDS Clin Res Suppl 8(2) (Year: 2012).*
Dey et al., "Structure-Based Stabilization of HIV-1 gp120 Enhances Humoral Immune Responses to the Induced Co-Receptor Binding Site," PLos Pathogens, 5:1000445 (2009).
International Search Report dated Feb. 21, 2014, from PCT/US2013/052855.

* cited by examiner

A

B

A

B

SEQUENCE LISTING

<160> NUMBER OF SEQ ID NOS: 18

<210> SEQ ID NO 1
<211> LENGTH: 2571
<212> TYPE: DNA
<213> ORGANISM: Human immunodeficiency virus type 1

<400> SEQUENCE: 1

| | | | | | |
|---|---|---|---|---|---|
| atgagagtga | aggagaaata | tcagcacttg | tggagatggg | ggtggagatg | gggcaccatg | 60 |
| ctccttggga | tgttgatgat | ctgtagtgct | acagaaaaat | tgtgggtcac | agtctattat | 120 |
| ggggtacctg | tgtggaagga | agcaaccacc | actctatttt | gtgcatcaga | tgctaaagca | 180 |
| tatgatacag | aggtacataa | tgtttgggcc | acacatgcct | gtgtacccac | agaccccaac | 240 |
| ccacaagaag | tagtattggt | aaatgtgaca | gaaaatttta | acatgtggaa | aaatgacatg | 300 |
| gtagaacaga | tgcatgagga | tataatcagt | ttatgggatc | aaagcctaaa | gccatgtgta | 360 |
| aaattaaccc | cactctgtgt | tagtttaaag | tgcactgatt | tgaagaatga | tactaatacc | 420 |
| aatagtagta | gcgggagaat | gataatggag | aaaggagaga | taaaaaactg | ctctttcaat | 480 |
| atcagcacaa | gcataagagg | taaggtgcag | aaagaatatg | catttttta | taaacttgat | 540 |
| ataataccaa | tagataatga | tactaccagc | tataagttga | caagttgtaa | cacctcagtc | 600 |
| attacacagg | cctgtccaaa | ggtatccttt | gagccaattc | ccatacatta | ttgtgccccg | 660 |
| gctggttttg | cgattctaaa | atgtaataat | aagacgttca | atggaacagg | accatgtaca | 720 |
| aatgtcagca | cagtacaatg | tacacatgga | attaggccag | tagtatcaac | tcaactgctg | 780 |
| ttaaatggca | gtctagcaga | agaagaggta | gtaattagat | ctgtcaattt | cacggacaat | 840 |
| gctaaaacca | taatagtaca | gctgaacaca | tctgtagaaa | ttaattgtac | aagacccaac | 900 |
| aacaatacaa | gaaaagaat | ccgtatccag | agaggaccag | ggagagcatt | tgttacaata | 960 |
| ggaaaaatag | gaaatatgag | acaagcacat | tgtaacatta | gtagagcaaa | atggaataac | 1020 |
| actttaaaac | agatagctag | caaattaaga | gaacaatttg | gaataataa | aacaataatc | 1080 |
| tttaagcaat | cctcaggagg | ggacccagaa | attgtaacgc | acagttttaa | ttgtggaggg | 1140 |
| gaatttttct | actgtaattc | aacacaactg | tttaatagta | cttggtttaa | tagtacttgg | 1200 |
| agtactgaag | ggtcaaataa | cactgaagga | agtgacacaa | tcaccctccc | atgcagaata | 1260 |
| aaacaaatta | taaacatgtg | gcagaaagta | ggaaaagcaa | tgtatgcccc | tcccatcagt | 1320 |
| ggacaaatta | gatgttcatc | aaatattaca | gggctgctat | taacaagaga | tggtggtaat | 1380 |
| agcaacaatg | agtccgagat | cttcagacct | ggaggaggag | atatgaggga | caattggaga | 1440 |
| agtgaattat | ataaatataa | agtagtaaaa | attgaaccat | taggagtagc | acccaccaag | 1500 |
| gcaaagagaa | gagtggtgca | gagagaaaaa | agagcagtgg | gaataggagc | tttgttcctt | 1560 |
| gggttcttgg | gagcagcagg | aagcactatg | ggcgcagcct | caatgacgct | gacggtacag | 1620 |
| gccagacaat | tattgtctgg | tatagtgcag | cagcagaaca | atttgctgag | ggctattgag | 1680 |
| gcgcaacagc | atctgttgca | actcacagtc | tggggcatca | agcagctcca | ggcaagaatc | 1740 |
| ctggctgtgg | aaagatacct | aaaggatcaa | cagctcctgg | gatttgggg | ttgctctgga | 1800 |
| aaactcattt | gcaccactgc | tgtgccttgg | aatgctagtt | ggagtaataa | atctctggaa | 1860 |
| cagatttgga | atcacacgac | ctggatggag | tgggacagag | aaattaacaa | ttacacaagc | 1920 |
| ttaatacact | ccttaattga | agaatcgcaa | aaccagcaag | aaaagaatga | acaagaatta | 1980 |
| ttggaattag | ataaatgggc | aagtttgtgg | aattggttta | acataacaaa | ttggctgtgg | 2040 |
| tatataaaat | tattcataat | gatagtagga | ggcttggtag | gtttaagaat | agttttgct | 2100 |

-continued

```
gtactttcta tagtgaatag agttaggcag ggatattcac cattatcgtt tcagacccac    2160
ctcccaaccc cgaggggacc cgacaggccc gaaggaataa agaagaaggt ggagagaga    2220 gacagagaca gatccattcg attagtgaac ggatccttgg cacttatctg ggacgatctg    2280
cggagcctgt gcctcttcag ctaccaccgc ttgagagact tactcttgat tgtaacgagg    2340
attgtggaac ttctgggacg caggggtgtgg gaagccctca atattggtg gaatctccta    2400 cagtattgga gtcaggaact aaagaatagt gctgttagct tgctcaatgc cacagccata    2460
gcagtagctg aggggacaga tagggttata gaagtagtac aaggagcttg tagagctatt    2520
cgccacatac ctagaagaat aagacagggc ttggaaagga ttttgctata a             2571
```

<210> SEQ ID NO 2
<211> LENGTH: 856
<212> TYPE: PRT
<213> ORGANISM: Human immunodeficiency virus type 1

<400> SEQUENCE: 2

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
        275                 280                 285
```

```
Asn Thr Ser Val Glu Ile Asn Cys Thr Arg Pro Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
                340                 345                 350

Phe Gly Asn Asn Lys Thr Ile Ile Phe Lys Gln Ser Ser Gly Gly Asp
                355                 360                 365

Pro Glu Ile Val Thr His Ser Phe Asn Cys Gly Gly Glu Phe Phe Tyr
370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
                420                 425                 430

Ala Met Tyr Ala Pro Pro Ile Ser Gly Gln Ile Arg Cys Ser Ser Asn
                435                 440                 445

Ile Thr Gly Leu Leu Leu Thr Arg Asp Gly Gly Asn Ser Asn Asn Glu
                450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
                500                 505                 510

Val Gly Ile Gly Ala Leu Phe Leu Gly Phe Leu Gly Ala Ala Gly Ser
                515                 520                 525

Thr Met Gly Ala Ala Ser Met Thr Leu Thr Val Gln Ala Arg Gln Leu
                530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
                580                 585                 590

Leu Gly Ile Trp Gly Cys Ser Gly Lys Leu Ile Cys Thr Thr Ala Val
                595                 600                 605

Pro Trp Asn Ala Ser Trp Ser Asn Lys Ser Leu Glu Gln Ile Trp Asn
610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
                660                 665                 670

Phe Asn Ile Thr Asn Trp Leu Trp Tyr Ile Lys Leu Phe Ile Met Ile
                675                 680                 685

Val Gly Gly Leu Val Gly Leu Arg Ile Val Phe Ala Val Leu Ser Ile
                690                 695                 700

Val Asn Arg Val Arg Gln Gly Tyr Ser Pro Leu Ser Phe Gln Thr His
```

| | | | 705 | | | | | 710 | | | | | 715 | | | | | 720 | |

Leu Pro Thr Pro Arg Gly Pro Asp Arg Pro Glu Gly Ile Glu Glu Glu
                           725                           730                     735

Gly Gly Glu Arg Asp Arg Asp Arg Ser Ile Arg Leu Val Asn Gly Ser
                  740                           745                         750

Leu Ala Leu Ile Trp Asp Asp Leu Arg Ser Leu Cys Leu Phe Ser Tyr
755                           760                         765

His Arg Leu Arg Asp Leu Leu Leu Ile Val Thr Arg Ile Val Glu Leu
    770                         775                         780

Leu Gly Arg Arg Gly Trp Glu Ala Leu Lys Tyr Trp Trp Asn Leu Leu
785                         790                         795                     800

Gln Tyr Trp Ser Gln Glu Leu Lys Asn Ser Ala Val Ser Leu Leu Asn
                  805                           810                         815

Ala Thr Ala Ile Ala Val Ala Glu Gly Thr Asp Arg Val Ile Glu Val
             820                         825                         830

Val Gln Gly Ala Cys Arg Ala Ile Arg His Ile Pro Arg Arg Ile Arg
         835                    840                         845

Gln Gly Leu Glu Arg Ile Leu Leu
850                         855

<210> SEQ ID NO 3
<211> LENGTH: 2544
<212> TYPE: DNA
<213> ORGANISM: Human immunodeficiency virus type 1

<400> SEQUENCE: 3

| | | |
|---|---|---|
| atgagagtga aggggatcag gaagagttat cagtacttgt ggaaggggg cacctrgctc | 60 |
| cttgggatat taatgatctg tagtgctgta gaaaagttgt gggtcacagt ctattatggg | 120 |
| gtacctgtgt ggaaagaagc aaccaccact ctattttgtg catcagatgc taaagcatat | 180 |
| gatacagagg tacataatgt ttgggccaca catgcctgtg tacccacaga ccccaaccca | 240 |
| caagaagtag tattggaaaa tgtaacagaa catttaaca tgtggaaaaa taacatggta | 300 |
| gaacagatgc aggaggatat aatcagttta tgggatcaaa gcctaaagcc atgtgtaaaa | 360 |
| ttaaccccac tctgtgttac tttaaattgc aaggatgtga atgctactaa taccactaat | 420 |
| gatagcgagg gaacgatgga gagggagaa ataaaaaact gctctttcaa tatcaccaca | 480 |
| agcataagag atgaggtgca gaaagaatat gctcttttt ataaacttga tgtagtacca | 540 |
| atagataata ataataccag ctataggttg ataagttgtg acacctcagt cattacacag | 600 |
| gcctgtccaa agatatcctt tgagccaatt cccatacatt attgtgcccc ggctggtttt | 660 |
| gcgattctaa gtgtaatga taagacgttc aatggaaaag gaccatgtaa aaatgtcagc | 720 |
| acagtacaat gtacacatgg aattaggcca gtagtatcaa ctcaactgct gctaaatggc | 780 |
| agtctagcag aagaagaggt agtaattaga tctgacaatt tcacgaacaa tgctaaaacc | 840 |
| ataatagtac agctgaaaga atctgtagaa attaattgta caagacccaa caacaataca | 900 |
| agaaaaagta tacatatagg accagggaga gcattttata ctacaggaga ataataggga | 960 |
| gatataagac aagcacattg taacattagt agagcaaaat ggaatgacac tttaaaacag | 1020 |
| atagttataa aattaagaga acaatttgag aataaaacaa tagtctttaa tcactcctca | 1080 |
| ggaggggacc cagaaattgt aatgcacagt tttaattgtg gaggagaatt tttctactgt | 1140 |
| aattcaacac aactgtttaa tagtacttgg aataataata ctgaagggtc aaataacact | 1200 |
| gaaggaaata ctatcacact cccatgcaga ataaaacaaa ttataaacat gtggcaggaa | 1260 |

-continued

```
gtaggaaaag caatgtatgc ccctcccatc agaggacaaa ttagatgttc atcaaatatt    1320
acagggctgc tattaacaag agatggtggt attaatgaga atgggaccga gatcttcaga    1380
cctggaggag gagatatgag ggacaattgg agaagtgaat tatataaata taaagtagta    1440
aaaattgaac cattaggagt agcacccacc aaggcaaaga gaagagtggt gcaaagagaa    1500
aaaagagcag tgggaatagg agctgtgttc cttgggttct tgggagcagc aggaagcact    1560
atgggcgcag cgtcaatgac actgacggta caggccagac tattattgtc tggtatagtg    1620
caacagcaga acaatttgct gagggctatt gaggcgcaac agcgtatgtt gcaactcaca    1680
gtctggggca tcaagcagct ccaggcaaga gtcctggctg tggaaagata cctaggggat    1740
caacagctcc tggggatttg gggttgctct ggaaaactca tttgcaccac tgctgtgcct    1800
tggaatgcta gttggagtaa taatctctg gataggattt ggaataacat gacctggatg    1860
gagtgggaaa gagaaattga caattacaca agcgaaatat acaccctaat tgaagaatcg    1920
cagaaccaac aagaaaagaa tgaacaagaa ttattggaat tagataaatg gcaagtttg    1980
tggaattggt ttgacataac aaaatggctg tggtatataa aaatattcat aatgatagta    2040
ggaggcttag taggtttaag actagttttt actgtacttt ctatagtgaa tagagttagg    2100
cagggatact caccattatc gtttcagacc ctcctcccag ccccgagggg acccgacagg    2160
cccgaaggaa tcgaagaaga aggtggagag agagacagag acagatccgg acgattagtg    2220
aacggattct tagcacttat ctgggtcgac ctgcggagcc tgtgcctctt cagctaccac    2280
cgcttgagag acttactctt gactgtaacg aggattgtgg aacttctggg acgcaggggg    2340
tgggaagtcc tgaaatattg gtggaatctc ctacagtatt ggagtcagga actaaagaat    2400
agtgctgtta gcttgctcaa tgccacagcc atagcagtag ctgaggggac agataggatt    2460
atagaagcat tacaaagaac ttatagagct attctccaca tacctacaag aataagacag    2520
ggcttggaaa gggctttgct ataa                                           2544
```

<210> SEQ ID NO 4
<211> LENGTH: 847
<212> TYPE: PRT
<213> ORGANISM: Human immunodeficiency virus type 1

<400> SEQUENCE: 4

```
Met Arg Val Lys Gly Ile Arg Lys Ser Tyr Gln Tyr Leu Trp Lys Gly
1               5                   10                  15

Gly Thr Leu Leu Leu Gly Ile Leu Met Ile Cys Ser Ala Val Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu His Phe Asn Met Trp Lys
                85                  90                  95

Asn Asn Met Val Glu Gln Met Gln Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Lys Asp Val Asn Ala Thr Asn Thr Thr Asn Asp Ser Glu Gly
    130                 135                 140
```

```
Thr Met Glu Arg Gly Glu Ile Lys Asn Cys Ser Phe Asn Ile Thr
145                 150                 155                 160

Ser Ile Arg Asp Glu Val Gln Lys Glu Tyr Ala Leu Phe Tyr Lys Leu
                165                 170                 175

Asp Val Val Pro Ile Asp Asn Asn Thr Ser Tyr Arg Leu Ile Ser
            180                 185                 190

Cys Asp Thr Ser Val Ile Thr Gln Ala Cys Pro Lys Ile Ser Phe Glu
        195                 200                 205

Pro Ile Pro Ile His Tyr Cys Ala Pro Ala Gly Phe Ala Ile Leu Lys
    210                 215                 220

Cys Asn Asp Lys Thr Phe Asn Gly Lys Gly Pro Cys Lys Asn Val Ser
225                 230                 235                 240

Thr Val Gln Cys Thr His Gly Ile Arg Pro Val Val Ser Thr Gln Leu
                245                 250                 255

Leu Leu Asn Gly Ser Leu Ala Glu Glu Val Val Ile Arg Ser Asp
            260                 265                 270

Asn Phe Thr Asn Asn Ala Lys Thr Ile Ile Val Gln Leu Lys Glu Ser
        275                 280                 285

Val Glu Ile Asn Cys Thr Arg Pro Asn Asn Thr Arg Lys Ser Ile
    290                 295                 300

His Ile Gly Pro Gly Arg Ala Phe Tyr Thr Thr Gly Glu Ile Ile Gly
305                 310                 315                 320

Asp Ile Arg Gln Ala His Cys Asn Ile Ser Arg Ala Lys Trp Asn Asp
                325                 330                 335

Thr Leu Lys Gln Ile Val Ile Lys Leu Arg Glu Gln Phe Glu Asn Lys
            340                 345                 350

Thr Ile Val Phe Asn His Ser Ser Gly Gly Asp Pro Glu Ile Val Met
        355                 360                 365

His Ser Phe Asn Cys Gly Gly Glu Phe Phe Tyr Cys Asn Ser Thr Gln
    370                 375                 380

Leu Phe Asn Ser Thr Trp Asn Asn Asn Thr Glu Gly Ser Asn Asn Thr
385                 390                 395                 400

Glu Gly Asn Thr Ile Thr Leu Pro Cys Arg Ile Lys Gln Ile Ile Asn
                405                 410                 415

Met Trp Gln Glu Val Gly Lys Ala Met Tyr Ala Pro Pro Ile Arg Gly
            420                 425                 430

Gln Ile Arg Cys Ser Ser Asn Ile Thr Gly Leu Leu Leu Thr Arg Asp
        435                 440                 445

Gly Gly Ile Asn Glu Asn Gly Thr Glu Ile Phe Arg Pro Gly Gly Gly
    450                 455                 460

Asp Met Arg Asp Asn Trp Arg Ser Glu Leu Tyr Lys Tyr Lys Val Val
465                 470                 475                 480

Lys Ile Glu Pro Leu Gly Val Ala Pro Thr Lys Ala Lys Arg Arg Val
                485                 490                 495

Val Gln Arg Glu Lys Arg Ala Val Gly Ile Gly Ala Val Phe Leu Gly
            500                 505                 510

Phe Leu Gly Ala Ala Gly Ser Thr Met Gly Ala Ala Ser Met Thr Leu
        515                 520                 525

Thr Val Gln Ala Arg Leu Leu Ser Gly Ile Val Gln Gln Gln Asn
    530                 535                 540

Asn Leu Leu Arg Ala Ile Glu Ala Gln Gln Arg Met Leu Gln Leu Thr
545                 550                 555                 560

Val Trp Gly Ile Lys Gln Leu Gln Ala Arg Val Leu Ala Val Glu Arg
```

Tyr Leu Gly Asp Gln Gln Leu Leu Gly Ile Trp Gly Cys Ser Gly Lys
       580                 585                 590

Leu Ile Cys Thr Thr Ala Val Pro Trp Asn Ala Ser Trp Ser Asn Lys
       595                 600                 605

Ser Leu Asp Arg Ile Trp Asn Asn Met Thr Trp Met Glu Trp Glu Arg
       610                 615                 620

Glu Ile Asp Asn Tyr Thr Ser Glu Ile Tyr Thr Leu Ile Glu Glu Ser
625                 630                 635                 640

Gln Asn Gln Gln Glu Lys Asn Glu Gln Glu Leu Leu Glu Leu Asp Lys
               645                 650                 655

Trp Ala Ser Leu Trp Asn Trp Phe Asp Ile Thr Lys Trp Leu Trp Tyr
               660                 665                 670

Ile Lys Ile Phe Ile Met Ile Val Gly Gly Leu Val Gly Leu Arg Leu
               675                 680                 685

Val Phe Thr Val Leu Ser Ile Val Asn Arg Val Arg Gln Gly Tyr Ser
       690                 695                 700

Pro Leu Ser Phe Gln Thr Leu Leu Pro Ala Pro Arg Gly Pro Asp Arg
705                 710                 715                 720

Pro Glu Gly Ile Glu Glu Gly Gly Glu Arg Asp Arg Asp Arg Ser
               725                 730                 735

Gly Arg Leu Val Asn Gly Phe Leu Ala Leu Ile Trp Val Asp Leu Arg
               740                 745                 750

Ser Leu Cys Leu Phe Ser Tyr His Arg Leu Arg Asp Leu Leu Leu Thr
               755                 760                 765

Val Thr Arg Ile Val Glu Leu Leu Gly Arg Arg Gly Trp Glu Val Leu
       770                 775                 780

Lys Tyr Trp Trp Asn Leu Leu Gln Tyr Trp Ser Gln Glu Leu Lys Asn
785                 790                 795                 800

Ser Ala Val Ser Leu Leu Asn Ala Thr Ala Ile Ala Val Ala Glu Gly
               805                 810                 815

Thr Asp Arg Ile Ile Glu Ala Leu Gln Arg Thr Tyr Arg Ala Ile Leu
               820                 825                 830

His Ile Pro Thr Arg Ile Arg Gln Gly Leu Glu Arg Ala Leu Leu
               835                 840                 845

<210> SEQ ID NO 5
<211> LENGTH: 2586
<212> TYPE: DNA
<213> ORGANISM: Human immunodeficiency virus type 1

<400> SEQUENCE: 5

```
atgagagtga tggggacaca gacgagttat cagcacttgt ggagatgggg aatcttaatt      60
ttggggatgc taataatttg taaagctaca gattggtggg tcacagtata ctatggagta     120
cctgtgtgga agatgcaga aaccacctta ttttgcgcat cagatgataa agcatatgag     180
acagaagcgc ataatgtctg gccacacat gcctgtgtac ccacagaccc caacccacaa     240
gaagtaaacc taaaaatgt gacagaagat tttaacatgt ggaaaaataa tatggtagag     300
cagatgcatg aagatataat cagtctatgg gatcaaagcc taaagccatg tgtaaaatta     360 accccctctct gtgtcacgtt aaactgtagc aatgccaaca ccaatagcac caatagcact     420
agcgccccta gcatgggccc tggagaaata aaaaactgtt cttttaatgt taccacagaa     480
gtaagagata agaaaagaa agtctatgca ctgttttata aacttgatgt agtacaaatt     540
```

```
aatgaaagtg acagtaatag tacaaaggat agtactcagt atagactaat aaattgtaat    600
acctcagcca tcacacaggc ttgtccaaag gtatcctttg agccaattcc tatacattat    660
tgtgccccag ctggttttgc gattctaaag tgtgaggatc cgagattcaa tggaacagga    720
ccatgcaata atgttagctc agtacaatgt acacatggaa ttatgccagt agcatcaact    780
caactgctgt tgaatggcag tctagcagaa aaagaggtga tgattagatc tgaaaatatt    840
acaaacaatg ccaaaaacat aatagtacag tttaatgaat cggtaccaat tacttgtatc    900
agacccaaca acaatacgag aaaaggtata cctattggac caggacaagt cttctataca    960
agtgacataa taggggatat aagacaagca tattgtagta tcaacaaaac aaaatgggat   1020
gcctctttac aaaaggtagc tgaacaatta agaaaacact ccctaataa acaataaat    1080 tttaccaaac cctcaggagg ggatctagaa attacaacac atagttttaa ttgtggagga   1140
gaatttttct attgtaatac aacaagcctg tttaatagca catggaagaa tggcgccacc   1200
atacaggaga atagcacgga gacaaatgga attatgactc tcccatgcag aataaaacaa   1260
attgtagaca tgtggcagga agtaggacaa gcaatgtatg cccctcccat tgcaggagta   1320
atatattgta catcaaacat tacaggaata atattgacaa gagatggtgg gagcagtaac   1380
accaatagta gatctttag gcctggagga ggagatatga gggacaattg gagaagtgaa   1440
ttatataagt ataaagtagt aaaaattgaa ccactaggag tagcacccctc cagggcaaag   1500 agaagagtgg tggagagaga aaaaagagca gtgggaatag gagctgtttt ccttgggttc   1560
ttgggagctg caggaagcac tatgggcgcg gcgtcaataa cgctgacggt acaggccaga   1620
cagttattat ctggcatagt gcaacagcaa agcaatttgc tgaaggctat agaggctcaa   1680
cagcatctgt tgaaactcac agtctggggc attaaacagc tccaggcaag agtcctggct   1740
ctggagagat acctacaaga tcaacagctc ctgggaattt ggggttgctc tggaaaactc   1800
atctgcacca ctactgtgcc ctggaactct agttggagta ataagactta cgaggagatt   1860
tggaacaaca tgacctggtt gcaatgggat agagaaattg acaattacac aaatataata   1920
tacaatctac ttgaagaatc gcagaaccag caggaaaaga atgaacaaga cttactggca   1980
ttagataaat gggcaagttt gtggaattgg tttagcataa caaactggct gtggtatata   2040
agaatattca taatgatagt aggaggcttg ataggattaa gaatagttat ggctataatt   2100
tctgtagtga atagagttag gcagggatac tcacctttgt catttcagat ccctacccca   2160
aacccagagg gtctcgacag gcacggaaga atcgaagaag aggtggagag caagacaga   2220 accagatcga ttcgattagt gagcggattc ttgggacttg cctgggacga cctacggagc   2280
ctgtgcctct tcagctacca ccgattgaga gattgcatct tgattgtagc gaggactgtg   2340
gaacttctgg gacacagcag tctcaaggga ctgagactgg ggtgggaggg cctcaaatat   2400 tggggaacc ttctactgta ttggggtcgg gaattgaaaa atagtgctat tagtttacta   2460
aattccacag caatagcagt agctgagtgg acagataggg ttatagaaat aggacaaaga   2520
gcttgcagag ctattctcaa catacctaga agaatcagac agggcttcga aagagcttta   2580
ctataa                                                              2586
```

<210> SEQ ID NO 6
<211> LENGTH: 861
<212> TYPE: PRT
<213> ORGANISM: Human immunodeficiency virus type 1

<400> SEQUENCE: 6

Met Arg Val Met Gly Thr Gln Thr Ser Tyr Gln His Leu Trp Arg Trp

```
1               5                   10                  15
Gly Ile Leu Ile Leu Gly Met Leu Ile Ile Cys Lys Ala Thr Asp Trp
                20                  25                  30

Trp Val Thr Val Tyr Tyr Gly Val Pro Val Trp Lys Asp Ala Glu Thr
                35                  40                  45

Thr Leu Phe Cys Ala Ser Asp Lys Ala Tyr Glu Thr Glu Ala His
            50                  55                  60

Asn Val Trp Ala Thr His Ala Cys Val Pro Thr Asp Pro Asn Pro Gln
65                  70                  75                  80

Glu Val Asn Leu Lys Asn Val Thr Glu Asp Phe Asn Met Trp Lys Asn
                85                  90                  95

Asn Met Val Glu Gln Met His Glu Asp Ile Ile Ser Leu Trp Asp Gln
                100                 105                 110

Ser Leu Lys Pro Cys Val Lys Leu Thr Pro Leu Cys Val Thr Leu Asn
                115                 120                 125

Cys Ser Asn Ala Asn Thr Asn Ser Thr Asn Ser Thr Ser Ala Pro Ser
    130                 135                 140

Met Gly Pro Gly Glu Ile Lys Asn Cys Ser Phe Asn Val Thr Thr Glu
145                 150                 155                 160

Val Arg Asp Lys Glu Lys Val Tyr Ala Leu Phe Tyr Lys Leu Asp
                165                 170                 175

Val Val Gln Ile Asn Glu Ser Asp Ser Asn Ser Thr Lys Asp Ser Thr
                180                 185                 190

Gln Tyr Arg Leu Ile Asn Cys Asn Thr Ser Ala Ile Thr Gln Ala Cys
                195                 200                 205

Pro Lys Val Ser Phe Glu Pro Ile Pro Ile His Tyr Cys Ala Pro Ala
    210                 215                 220

Gly Phe Ala Ile Leu Lys Cys Glu Asp Pro Arg Phe Asn Gly Thr Gly
225                 230                 235                 240

Pro Cys Asn Asn Val Ser Ser Val Gln Cys Thr His Gly Ile Met Pro
                245                 250                 255

Val Ala Ser Thr Gln Leu Leu Leu Asn Gly Ser Leu Ala Glu Lys Glu
                260                 265                 270

Val Met Ile Arg Ser Glu Asn Ile Thr Asn Asn Ala Lys Asn Ile Ile
                275                 280                 285

Val Gln Phe Asn Glu Ser Val Pro Ile Thr Cys Ile Arg Pro Asn Asn
                290                 295                 300

Asn Thr Arg Lys Gly Ile Pro Ile Gly Pro Gly Gln Val Phe Tyr Thr
305                 310                 315                 320

Ser Asp Ile Ile Gly Asp Ile Arg Gln Ala Tyr Cys Ser Ile Asn Lys
                325                 330                 335

Thr Lys Trp Asp Ala Ser Leu Gln Lys Val Ala Glu Gln Leu Arg Lys
                340                 345                 350

His Phe Pro Asn Lys Thr Ile Asn Phe Thr Lys Pro Ser Gly Gly Asp
                355                 360                 365

Leu Glu Ile Thr Thr His Ser Phe Asn Cys Gly Gly Glu Phe Phe Tyr
                370                 375                 380

Cys Asn Thr Thr Ser Leu Phe Asn Ser Thr Trp Lys Asn Gly Ala Thr
385                 390                 395                 400

Ile Gln Glu Asn Ser Thr Glu Thr Asn Gly Ile Met Thr Leu Pro Cys
                405                 410                 415

Arg Ile Lys Gln Ile Val Asp Met Trp Gln Glu Val Gly Gln Ala Met
                420                 425                 430
```

```
Tyr Ala Pro Pro Ile Ala Gly Val Ile Tyr Cys Thr Ser Asn Ile Thr
            435                 440                 445

Gly Ile Ile Leu Thr Arg Asp Gly Gly Ser Ser Asn Thr Asn Ser Glu
    450                 455                 460

Ile Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Ser Arg Ala Lys Arg Arg Val Val Glu Arg Glu Lys Arg Ala Val Gly
            500                 505                 510

Ile Gly Ala Val Phe Leu Gly Phe Leu Gly Ala Ala Gly Ser Thr Met
            515                 520                 525

Gly Ala Ala Ser Ile Thr Leu Thr Val Gln Ala Arg Gln Leu Leu Ser
            530                 535                 540

Gly Ile Val Gln Gln Gln Ser Asn Leu Leu Lys Ala Ile Glu Ala Gln
545                 550                 555                 560

Gln His Leu Leu Lys Leu Thr Val Trp Gly Ile Lys Gln Leu Gln Ala
                565                 570                 575

Arg Val Leu Ala Leu Glu Arg Tyr Leu Gln Asp Gln Gln Leu Leu Gly
            580                 585                 590

Ile Trp Gly Cys Ser Gly Lys Leu Ile Cys Thr Thr Thr Val Pro Trp
            595                 600                 605

Asn Ser Ser Trp Ser Asn Lys Thr Tyr Glu Glu Ile Trp Asn Asn Met
            610                 615                 620

Thr Trp Leu Gln Trp Asp Arg Glu Ile Asp Asn Tyr Thr Asn Ile Ile
625                 630                 635                 640

Tyr Asn Leu Leu Glu Glu Ser Gln Asn Gln Gln Glu Lys Asn Glu Gln
                645                 650                 655

Asp Leu Leu Ala Leu Asp Lys Trp Ala Ser Leu Trp Asn Trp Phe Ser
            660                 665                 670

Ile Thr Asn Trp Leu Trp Tyr Ile Arg Ile Phe Ile Met Ile Val Gly
            675                 680                 685

Gly Leu Ile Gly Leu Arg Ile Val Met Ala Ile Ile Ser Val Val Asn
            690                 695                 700

Arg Val Arg Gln Gly Tyr Ser Pro Leu Ser Phe Gln Ile Pro Thr Pro
705                 710                 715                 720

Asn Pro Glu Gly Leu Asp Arg His Gly Arg Ile Glu Glu Gly Gly Gly
                725                 730                 735

Glu Gln Asp Arg Thr Arg Ser Ile Arg Leu Val Ser Gly Phe Leu Gly
            740                 745                 750

Leu Ala Trp Asp Asp Leu Arg Ser Leu Cys Leu Phe Ser Tyr His Arg
            755                 760                 765

Leu Arg Asp Cys Ile Leu Ile Val Ala Arg Thr Val Glu Leu Leu Gly
            770                 775                 780

His Ser Ser Leu Lys Gly Leu Arg Leu Gly Trp Glu Gly Leu Lys Tyr
785                 790                 795                 800

Leu Gly Asn Leu Leu Leu Tyr Trp Gly Arg Glu Leu Lys Asn Ser Ala
                805                 810                 815

Ile Ser Leu Leu Asn Ser Thr Ala Ile Ala Val Ala Glu Trp Thr Asp
            820                 825                 830

Arg Val Ile Glu Ile Gly Gln Arg Ala Cys Arg Ala Ile Leu Asn Ile
            835                 840                 845
```

Pro Arg Arg Ile Arg Gln Gly Phe Glu Arg Ala Leu Leu
    850                 855                 860

<210> SEQ ID NO 7
<211> LENGTH: 2526
<212> TYPE: DNA
<213> ORGANISM: Human immunodeficiency virus type 1

<400> SEQUENCE: 7

| | | | | |
|---|---|---|---|---|
| atgagagtga | agggatatt | gaggaattgt | caacaatggt | ggatatgggg | catcttaggc | 60 |
| ttttggatgc | taatgatttg | taatgtggtg | ggaaacttgt | gggtcacagt | ctattatggg | 120 |
| gtacctgtgt | ggaaagaagc | aaaaactact | ctattctgtg | catcagatgc | taaatcatat | 180 |
| gagagagaag | tgcataatgt | atgggctaca | catgcctgtg | tacccacaga | ccccgaccca | 240 |
| caagaactgg | ttatggcaaa | tgtaacagaa | aattttaaca | tgtggaaaaa | tgacatggta | 300 |
| gatcagatgc | atgaggatat | aatcagttta | tgggatcaaa | gcctaaagcc | atgtgtaaaa | 360 |
| ttgaccccac | tctgtgtcac | tttaaattgt | acaagtcctg | ctgccacaa | tgagagcgag | 420 |
| acaagagtaa | acattgctc | tttcaatata | accacagatg | taaaagatag | aaaacagaag | 480 |
| gtgaatgcaa | cttttatga | ccttgatata | gtaccactta | gcagctctga | caactctagc | 540 |
| aactctagtc | tgtatagatt | aataagttgt | aatacctcaa | ccataacaca | agcctgtcca | 600 |
| aaggtctctt | ttgacccaat | tcctatacat | tattgtgctc | cagctggtta | tgcgattcta | 660 |
| aaatgtaata | ataagacatt | cagtgggaaa | ggaccatgtt | ctaatgtcag | tacagtacaa | 720 |
| tgtacacatg | gaattaggcc | agtggtatca | actcaactgc | tgttaaatgg | tagcctagca | 780 |
| gaagaagaga | tagtaattag | atctgaaaat | ctgacagaca | atgccaaaac | aataatagta | 840 |
| catcttaata | aatctgtaga | aattgagtgt | ataagacctg | gcaataatac | aagaaaaagt | 900 |
| ataaggctag | gaccaggaca | aacattctat | gcaacagggg | atgtaatagg | agacataaga | 960 |
| aaggcatatt | gtaaaattaa | tggaagtgag | tggaatgaaa | ctttaacaaa | agtaagtgaa | 1020 |
| aaattaaaag | aatattttaa | taaaacaata | agatttgccc | agcactcggg | aggggaccta | 1080 |
| gaagtgacaa | cacatagctt | taattgtaga | ggagaatttt | tctattgcaa | tacatcagaa | 1140 |
| ctatttaata | gtaatgcaac | agaaagcaac | atcacactcc | catgcagaat | aaaacaaatt | 1200 |
| ataaacatgt | ggcagggggt | aggacgagca | atgtatgccc | ctcccatcag | aggagaaata | 1260 |
| aaatgtacat | caaatatcac | aggactacta | ttaacacgcg | atggaggcaa | caacaataat | 1320 |
| tcaacagagg | agatattcag | acctgaagga | ggaaatatga | gggacaattg | gagaagtgaa | 1380 |
| ttatacaaat | ataagtggt | ggagattaag | ccattgggaa | tagcacccac | tgaggcaaaa | 1440 |
| aggagagtgg | tgcagagaga | aaaaagagca | gtgggaatag | gagctgtgtt | ccttgggttc | 1500 |
| ttgggagcag | caggaagcac | tatgggcgcg | gcgtcaataa | cgctgacggt | acaggccaga | 1560 |
| caattattgt | ctggtatagt | gcaacagcaa | agcaatttgc | tgagggctat | agaggcgcaa | 1620 |
| caacatctgt | tgcaactcac | agtctggggc | attaagcagc | tccaggcaag | agtcctggct | 1680 |
| atagaaagat | acctacagga | tcaacagctc | ctagggattt | ggggctgctc | tggaaaactc | 1740 |
| atctgcacca | ctgcagtgcc | ttggaactcc | agttggagta | ataaatctaa | ggaagaaatt | 1800 |
| tggggcaaca | tgacctggat | gcagtgggat | aagaagtta | gtaattacac | attcacaata | 1860 |
| taccagttgc | ttgaagaatc | gcaataccag | caggaacaaa | atgaaaaaga | actattagca | 1920 |
| ttgaacaagt | ggaatgatct | gtggagttgg | tttaacataa | caattggtt | gtggtatata | 1980 |
| aaaatattca | taatgatagt | aggaggctta | ataggtttaa | gaataatttt | tgctgtactt | 2040 |

-continued

```
tccatagtga atagagttag gcagggatac tcacctttgt cgtttcagac ccttaccccg    2100
aacccagggg gacccgacag gctcggaaga atcgaaggag aaggtggaga gcaagacaaa    2160
aacagatcca ttcgattagt gaacggattc ttagctctta tctgggacga cctgtggagc    2220
ctgtgccgct tcagctacca cctattgaga gacttcatat tgattgtagc gagagcggtg    2280
gaacttctgg gacgcagcag tctcaaggga ctacagaggg ggtgggaagc tcttaaatat    2340
ctgggaaatc ttatgcagta ttggggtctg gaactaaaaa gaagtgctat taatctgtta    2400
gataacacag cagtagcagt agctgaagga acagatagga ttatagaatt agcacaaggc    2460
atttatagag ctatctgcaa catacctaga agaataagac agggctttga agcagcttta    2520
caataa                                                                2526
```

<210> SEQ ID NO 8
<211> LENGTH: 841
<212> TYPE: PRT
<213> ORGANISM: Human immunodeficiency virus type 1

<400> SEQUENCE: 8

```
Met Arg Val Lys Gly Ile Leu Arg Asn Cys Gln Gln Trp Trp Ile Trp
1               5                   10                  15

Gly Ile Leu Gly Phe Trp Met Leu Met Ile Cys Asn Val Val Gly Asn
                20                  25                  30

Leu Trp Val Thr Val Tyr Tyr Gly Val Pro Val Trp Lys Glu Ala Lys
            35                  40                  45

Thr Thr Leu Phe Cys Ala Ser Asp Ala Lys Ser Tyr Glu Arg Glu Val
        50                  55                  60

His Asn Val Trp Ala Thr His Ala Cys Val Pro Thr Asp Pro Asp Pro
65                  70                  75                  80

Gln Glu Leu Val Met Ala Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Ser Pro Ala Ala His Asn Glu Ser Glu Thr Arg Val Lys
130                 135                 140

His Cys Ser Phe Asn Ile Thr Thr Asp Val Lys Asp Arg Lys Gln Lys
145                 150                 155                 160

Val Asn Ala Thr Phe Tyr Asp Leu Asp Ile Val Pro Leu Ser Ser Ser
                165                 170                 175

Asp Asn Ser Ser Asn Ser Ser Leu Tyr Arg Leu Ile Ser Cys Asn Thr
            180                 185                 190

Ser Thr Ile Thr Gln Ala Cys Pro Lys Val Ser Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Ser Gly Lys Gly Pro Cys Ser Asn Val Ser Thr Val Gln
225                 230                 235                 240

Cys Thr His Gly Ile Arg Pro Val Val Ser Thr Gln Leu Leu Leu Asn
                245                 250                 255

Gly Ser Leu Ala Glu Glu Glu Ile Val Ile Arg Ser Glu Asn Leu Thr
            260                 265                 270

Asp Asn Ala Lys Thr Ile Ile Val His Leu Asn Lys Ser Val Glu Ile
        275                 280                 285
```

```
Glu Cys Ile Arg Pro Gly Asn Asn Thr Arg Lys Ser Ile Arg Leu Gly
    290                 295                 300
Pro Gly Gln Thr Phe Tyr Ala Thr Gly Asp Val Ile Gly Asp Ile Arg
305                 310                 315                 320
Lys Ala Tyr Cys Lys Ile Asn Gly Ser Glu Trp Asn Glu Thr Leu Thr
                325                 330                 335
Lys Val Ser Glu Lys Leu Lys Glu Tyr Phe Asn Lys Thr Ile Arg Phe
            340                 345                 350
Ala Gln His Ser Gly Gly Asp Leu Glu Val Thr Thr His Ser Phe Asn
        355                 360                 365
Cys Arg Gly Glu Phe Phe Tyr Cys Asn Thr Ser Glu Leu Phe Asn Ser
    370                 375                 380
Asn Ala Thr Glu Ser Asn Ile Thr Leu Pro Cys Arg Ile Lys Gln Ile
385                 390                 395                 400
Ile Asn Met Trp Gln Gly Val Gly Arg Ala Met Tyr Ala Pro Pro Ile
                405                 410                 415
Arg Gly Glu Ile Lys Cys Thr Ser Asn Ile Thr Gly Leu Leu Leu Thr
            420                 425                 430
Arg Asp Gly Gly Asn Asn Asn Ser Thr Glu Glu Ile Phe Arg Pro
        435                 440                 445
Glu Gly Gly Asn Met Arg Asp Asn Trp Arg Ser Glu Leu Tyr Lys Tyr
    450                 455                 460
Lys Val Val Glu Ile Lys Pro Leu Gly Ile Ala Pro Thr Glu Ala Lys
465                 470                 475                 480
Arg Arg Val Val Gln Arg Glu Lys Arg Ala Val Gly Ile Gly Ala Val
                485                 490                 495
Phe Leu Gly Phe Leu Gly Ala Ala Gly Ser Thr Met Gly Ala Ala Ser
            500                 505                 510
Ile Thr Leu Thr Val Gln Ala Arg Gln Leu Leu Ser Gly Ile Val Gln
        515                 520                 525
Gln Gln Ser Asn Leu Leu Arg Ala Ile Glu Ala Gln Gln His Leu Leu
    530                 535                 540
Gln Leu Thr Val Trp Gly Ile Lys Gln Leu Gln Ala Arg Val Leu Ala
545                 550                 555                 560
Ile Glu Arg Tyr Leu Gln Asp Gln Gln Leu Leu Gly Ile Trp Gly Cys
                565                 570                 575
Ser Gly Lys Leu Ile Cys Thr Thr Ala Val Pro Trp Asn Ser Ser Trp
            580                 585                 590
Ser Asn Lys Ser Lys Glu Glu Ile Trp Gly Asn Met Thr Trp Met Gln
        595                 600                 605
Trp Asp Lys Glu Val Ser Asn Tyr Thr Phe Thr Ile Tyr Gln Leu Leu
    610                 615                 620
Glu Glu Ser Gln Tyr Gln Gln Glu Gln Asn Glu Lys Glu Leu Leu Ala
625                 630                 635                 640
Leu Asn Lys Trp Asn Asp Leu Trp Ser Trp Phe Asn Ile Thr Asn Trp
                645                 650                 655
Leu Trp Tyr Ile Lys Ile Phe Ile Met Ile Val Gly Gly Leu Ile Gly
            660                 665                 670
Leu Arg Ile Ile Phe Ala Val Leu Ser Ile Val Asn Arg Val Arg Gln
        675                 680                 685
Gly Tyr Ser Pro Leu Ser Phe Gln Thr Leu Thr Pro Asn Pro Gly Gly
    690                 695                 700
```

```
Pro Asp Arg Leu Gly Arg Ile Glu Gly Glu Gly Glu Gln Asp Lys
705                 710                 715                 720

Asn Arg Ser Ile Arg Leu Val Asn Gly Phe Leu Ala Leu Ile Trp Asp
            725                 730                 735

Asp Leu Trp Ser Leu Cys Arg Phe Ser Tyr His Leu Leu Arg Asp Phe
                740                 745                 750

Ile Leu Ile Val Ala Arg Ala Val Glu Leu Leu Gly Arg Ser Ser Leu
            755                 760                 765

Lys Gly Leu Gln Arg Gly Trp Glu Ala Leu Lys Tyr Leu Gly Asn Leu
        770                 775                 780

Met Gln Tyr Trp Gly Leu Glu Leu Lys Arg Ser Ala Ile Asn Leu Leu
785                 790                 795                 800

Asp Thr Thr Ala Val Ala Val Ala Glu Gly Thr Asp Arg Ile Ile Glu
                805                 810                 815

Leu Ala Gln Gly Ile Tyr Arg Ala Ile Cys Asn Ile Pro Arg Arg Ile
            820                 825                 830

Arg Gln Gly Phe Glu Ala Ala Leu Gln
        835                 840

<210> SEQ ID NO 9
<211> LENGTH: 2592
<212> TYPE: DNA
<213> ORGANISM: Human immunodeficiency virus type 1

<400> SEQUENCE: 9
atgatagtga ctatgaaagc aatggagaag aggaacaaga agttatggac cttgtactta      60
gccatggctt tgataacccc atgtttgagc cttagacagc tatatgcaac agtctatgct     120
ggggtgcctg tatgggaaga tgcaacacca gtactattct gtgcttcaga tgctaaccta     180
acaagcactg aaaagcataa tatttgggca tcacaagcct gtgttcctac agaccccact     240
ccatatgaat atccattgca caatgtgaca atgactttta atatatgaa aaattacatg     300 gtagaacaaa tgcaggaaga cattattagt ttatgggacc agagtcttaa accttgtgtt     360
caaatgactt tcctgtgtgt acaaatggag tgtacaaaca tagctggaac aacaaatgaa     420
aaccttatga gaagtgtga gtttaatgta accactgtta tcaaagacaa aaaggagaaa     480
aaacaggctc tattctatgt atcagatttg atggaactga atgagacaag cagcacaaat     540
aagacaaaca gcaaaatgta tacattaact aattgtaact ccacaaccat cacgcaagcc     600
tgtccaaagg tatcttttga accaattcca atacactatt gtgctccagc aggatatgct     660
atctttaagt gtaacagcac agaatttaat ggaacaggca catgcagaaa cataacggta     720
gttacttgta cacatggcat taggccaaca gtaagtactc agctaatatt aaatgggaca     780
ctctctaaag gaaaaataag aatgatgca aaagatattt ggaaggtgg aaaaaatatc     840 atagtgaccc taaactctac cctaaacatg acctgtgaaa gaccacaaat agacatacaa     900
gagatgagaa taggtccaat ggcctggtac agcatgggaa taggggaac agcaggaaac     960 agctcaaggg cagcttattg caagtataat gccactgatt ggggaaaaat attaaaacaa    1020
acagctgaaa ggtatttaga actagtaaac aatacaggta gtattaacat gacattcaat    1080
cacagcagcg gtggagatct agaggtaacc catttacact taactgtca tggagaattc    1140 ttttattgta acacagctaa gatgtttaat tatacctttt catgtaacgg aaccacctgt    1200
agtgttagta atgttagtca aggtaacaat ggcactctac cttgcaaact gagacaggtg    1260
gtaaggtcat ggataagggg acagtcggga ctctatgcac ctcccatcaa aggtaatcta    1320
```

```
acatgtatgt caaacataac tggaatgatc ctacaaatgg ataacacatg gaacagcagc    1380
aacaacaatg taacatttag accaataggg ggagacatga aagatatatg gagaactgaa    1440
ttgttcaact acaaagtagt aagggtaaaa cctttagtg tggcacccac acgtattgca    1500
aggccagtca taagcactag aactcataga gaaaaagag cagtaggatt gggaatgcta    1560 ttcttgggg ttctaagtgc agcaggtagc actatgggcg cagcggcaac aacgctggcg    1620
gtacagaccc acactttgct gaagggtata gtgcaacagc aggacaacct gctaagagca    1680
atacaggccc agcagcaatt gctgaggcta tctrtatggg gtatcagaca actccgagct    1740
cgcctgctag ccttagaaac cttactacag aatcagcaac tcctaagcct atggggctgt    1800
aaaggaaagc tagtctgcta cacatcagta aaatggaata gaacatggat aggaaacgaa    1860
agcatttggg acaccttaac atggcaggaa tgggatcggc agataagcaa cataagctcc    1920
accatatatg aggaaataca aaaggcacaa gtacagcagg aacaaaatga gaaaagttg    1980 ctggagttag atgaatgggc ctctatttgg aattggcttg acataactaa atggttgtgg    2040
tatataaaaa tagcaataat catagtagga gcactagtag gggtgagagt tatcatgata    2100
gtacttaata tagtgaaaaa cattaggcag ggatatcaac ccctctcgtt acagatcccc    2160
aaccatcacc aagaggaagc aggaacgcca ggaagaacag gaggaggagg tggagaagaa    2220
ggcaggccca ggtggatacc ctcgccgcaa gggttcttgc cactgttgta cacggacctc    2280
agaacaataa tattgtggac ttaccacctc ttgagcaact tagcatcagg gatccagaag    2340
gtgatcagct atctgaggct tggactgtgg atcctagggc agaagataat taatgtttgc    2400
agaatttgtg cagctgtaac acaatactgg ctacaagaat tgcagaatag tgctacaagc    2460
ttgctagaca cacttgcagt ggcagtagcc aattggactg acggcataat cgcagggata    2520
caaagaatag gaacaggaat tcgtaacatc ccaaggagaa ttagacaggg cttagaaaga    2580
agtttattgt aa                                                        2592
```

<210> SEQ ID NO 10
<211> LENGTH: 863
<212> TYPE: PRT
<213> ORGANISM: Human immunodeficiency virus type 1
<220> FEATURE:
<221> NAME/KEY: misc_feature
<222> LOCATION: (572)..(572)
<223> OTHER INFORMATION: Xaa can be any naturally occurring amino acid

<400> SEQUENCE: 10

```
Met Ile Val Thr Met Lys Ala Met Glu Lys Arg Asn Lys Lys Leu Trp
1               5                   10                  15

Thr Leu Tyr Leu Ala Met Ala Leu Ile Thr Pro Cys Leu Ser Leu Arg
                20                  25                  30

Gln Leu Tyr Ala Thr Val Tyr Ala Gly Val Pro Val Trp Glu Asp Ala
            35                  40                  45

Thr Pro Val Leu Phe Cys Ala Ser Asp Ala Asn Leu Thr Ser Thr Glu
        50                  55                  60

Lys His Asn Ile Trp Ala Ser Gln Ala Cys Val Pro Thr Asp Pro Thr
65                  70                  75                  80

Pro Tyr Glu Tyr Pro Leu His Asn Val Thr Asp Phe Asn Ile Trp
                85                  90                  95

Lys Asn Tyr Met Val Glu Gln Met Gln Glu Asp Ile Ile Ser Leu Trp
                100                 105                 110

Asp Gln Ser Leu Lys Pro Cys Val Gln Met Thr Phe Leu Cys Val Gln
            115                 120                 125
```

```
Met Glu Cys Thr Asn Ile Ala Gly Thr Thr Asn Glu Asn Leu Met Lys
130                 135                 140

Lys Cys Glu Phe Asn Val Thr Thr Val Ile Lys Asp Lys Lys Glu Lys
145                 150                 155                 160

Lys Gln Ala Leu Phe Tyr Val Ser Asp Leu Met Glu Leu Asn Glu Thr
                165                 170                 175

Ser Ser Thr Asn Lys Thr Asn Ser Lys Met Tyr Thr Leu Thr Asn Cys
                180                 185                 190

Asn Ser Thr Thr Ile Thr Gln Ala Cys Pro Lys Val Ser Phe Glu Pro
                195                 200                 205

Ile Pro Ile His Tyr Cys Ala Pro Ala Gly Tyr Ala Ile Phe Lys Cys
210                 215                 220

Asn Ser Thr Glu Phe Asn Gly Thr Gly Thr Cys Arg Asn Ile Thr Val
225                 230                 235                 240

Val Thr Cys Thr His Gly Ile Arg Pro Thr Val Ser Thr Gln Leu Ile
                245                 250                 255

Leu Asn Gly Thr Leu Ser Lys Gly Lys Ile Arg Met Met Ala Lys Asp
                260                 265                 270

Ile Leu Glu Gly Gly Lys Asn Ile Ile Val Thr Leu Asn Ser Thr Leu
                275                 280                 285

Asn Met Thr Cys Glu Arg Pro Gln Ile Asp Ile Gln Glu Met Arg Ile
290                 295                 300

Gly Pro Met Ala Trp Tyr Ser Met Gly Ile Gly Gly Thr Ala Gly Asn
305                 310                 315                 320

Ser Ser Arg Ala Ala Tyr Cys Lys Tyr Asn Ala Thr Asp Trp Gly Lys
                325                 330                 335

Ile Leu Lys Gln Thr Ala Glu Arg Tyr Leu Glu Leu Val Asn Asn Thr
                340                 345                 350

Gly Ser Ile Asn Met Thr Phe Asn His Ser Ser Gly Gly Asp Leu Glu
                355                 360                 365

Val Thr His Leu His Phe Asn Cys His Gly Glu Phe Phe Tyr Cys Asn
370                 375                 380

Thr Ala Lys Met Phe Asn Tyr Thr Phe Ser Cys Asn Gly Thr Thr Cys
385                 390                 395                 400

Ser Val Ser Asn Val Ser Gln Gly Asn Asn Gly Thr Leu Pro Cys Lys
                405                 410                 415

Leu Arg Gln Val Val Arg Ser Trp Ile Arg Gly Gln Ser Gly Leu Tyr
                420                 425                 430

Ala Pro Pro Ile Lys Gly Asn Leu Thr Cys Met Ser Asn Ile Thr Gly
                435                 440                 445

Met Ile Leu Gln Met Asp Asn Thr Trp Asn Ser Ser Asn Asn Asn Val
450                 455                 460

Thr Phe Arg Pro Ile Gly Gly Asp Met Lys Asp Ile Trp Arg Thr Glu
465                 470                 475                 480

Leu Phe Asn Tyr Lys Val Val Arg Val Lys Pro Phe Ser Val Ala Pro
                485                 490                 495

Thr Arg Ile Ala Arg Pro Val Ile Ser Thr Arg Thr His Arg Glu Lys
                500                 505                 510

Arg Ala Val Gly Leu Gly Met Leu Phe Leu Gly Val Leu Ser Ala Ala
                515                 520                 525

Gly Ser Thr Met Gly Ala Ala Ala Thr Thr Leu Ala Val Gln Thr His
530                 535                 540
```

Thr Leu Leu Lys Gly Ile Val Gln Gln Gln Asp Asn Leu Leu Arg Ala
545                 550                 555                 560

Ile Gln Ala Gln Gln Leu Leu Arg Leu Ser Xaa Trp Gly Ile Arg
            565                 570                 575

Gln Leu Arg Ala Arg Leu Leu Ala Leu Glu Thr Leu Leu Gln Asn Gln
            580                 585                 590

Gln Leu Leu Ser Leu Trp Gly Cys Lys Gly Lys Leu Val Cys Tyr Thr
            595                 600                 605

Ser Val Lys Trp Asn Arg Thr Trp Ile Gly Asn Glu Ser Ile Trp Asp
    610                 615                 620

Thr Leu Thr Trp Gln Glu Trp Asp Arg Gln Ile Ser Asn Ile Ser Ser
625                 630                 635                 640

Thr Ile Tyr Glu Glu Ile Gln Lys Ala Gln Val Gln Gln Glu Gln Asn
            645                 650                 655

Glu Lys Lys Leu Leu Glu Leu Asp Glu Trp Ala Ser Ile Trp Asn Trp
        660                 665                 670

Leu Asp Ile Thr Lys Trp Leu Trp Tyr Ile Lys Ile Ala Ile Ile Ile
    675                 680                 685

Val Gly Ala Leu Val Gly Val Arg Val Ile Met Ile Val Leu Asn Ile
690                 695                 700

Val Lys Asn Ile Arg Gln Gly Tyr Gln Pro Leu Ser Leu Gln Ile Pro
705                 710                 715                 720

Asn His His Gln Glu Glu Ala Gly Thr Pro Gly Arg Thr Gly Gly Gly
            725                 730                 735

Gly Gly Glu Glu Gly Arg Pro Arg Trp Ile Pro Ser Pro Gln Gly Phe
        740                 745                 750

Leu Pro Leu Leu Tyr Thr Asp Leu Arg Thr Ile Ile Leu Trp Thr Tyr
    755                 760                 765

His Leu Leu Ser Asn Leu Ala Ser Gly Ile Gln Lys Val Ile Ser Tyr
770                 775                 780

Leu Arg Leu Gly Leu Trp Ile Leu Gly Gln Lys Ile Ile Asn Val Cys
785                 790                 795                 800

Arg Ile Cys Ala Ala Val Thr Gln Tyr Trp Leu Gln Glu Leu Gln Asn
            805                 810                 815

Ser Ala Thr Ser Leu Leu Asp Thr Leu Ala Val Ala Val Ala Asn Trp
        820                 825                 830

Thr Asp Gly Ile Ile Ala Gly Ile Gln Arg Ile Gly Thr Gly Ile Arg
    835                 840                 845

Asn Ile Pro Arg Arg Ile Arg Gln Gly Leu Glu Arg Ser Leu Leu
850                 855                 860

<210> SEQ ID NO 11
<211> LENGTH: 2577
<212> TYPE: DNA
<213> ORGANISM: Simian immunodeficiency virus
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (1473)..(1473)
<223> OTHER INFORMATION: n is a, c, g, or t

<400> SEQUENCE: 11
atgaggaagc cgatacatat tatttggggt ctggctttgc taatccagtt tatagagaag      60
gggacgaatg aagactatgt aacagtattc tatggagtcc ctgtctggag aaatgcgaca     120

-continued

```
cctactctat tttgtgccac aaatgcctcc atgacaagta cagaggtgca caatgtatgg    180
gcaactacca gttgtgtgcc aatagatcca gatcctattg tagttaggct caatacctca    240
gtctggttta atgcttataa aaattatatg gtagaaagta tgacagaaga tatgntacaa    300
ttattccaac aaagccataa gccatgtgta aaactaacac ctatgtgtat aaaaatgaat    360
tgtacaggat acaatggaac acctacaaca ccaagtacaa caacaagtac agtaacacca    420
aagacaacaa caccaatagt agatggcatg aagctacaag aatgtaactt taatcagagc    480
acaggattta aagataagaa acaaaaaatg aaagccatat tttataaagg agatcttatg    540
aagtgtcagg acaacaatga gactaactgc tattacttat ggcactgcaa caccacaact    600
atcacacaat cctgtgaaaa gtctactttt gaaccaattc ctatacatta ttgtgctcca    660
gcaggatatg ctatattgag atgtgaagat gaggatttta caggagtagg gatgtgtaaa    720
aatgtctcag tagtacattg cactcatgga ataagcccaa tggtggcaac atggttacta    780
ttaaatggaa cttaccaaac aaacacttca gtagtaatga atggtcgcaa aaatgaatct    840
gtgcttgtaa gatttggaaa agaattcgaa aacttaacaa ttacatgtat aagaccagga    900
aataggacag taagaaatct acaaatagga ccaggaatga cttttctataa cgtagaaata    960 gcaacaggag acactaggaa agcgttctgt acagtcaata agacgctatg ggaacaagca   1020
cgtaacaaaa cagagcacgt tcttgcggag cattggaaaa aagtagacaa caaaaccaat   1080
gcgaaaacaa tatggacatt ccaagatgga gatcctgaag taaagtgca ttggtttaat    1140 tgccaaggag aattctttta ttgtgatata cacccttggt tcaatgccac atacacggga   1200
aacctcatca caaacggagc cctcatagca cattgcagaa ttaagcagat agttaatcat   1260
tggggcatag tttcaaaagg catttactta gcccctagga gagggaatgt ttcctgtact   1320
tccagcataa ctggaattat gttggaaggt caaatatata atgaaactgt taagtgtca   1380 cctgctgcaa gagtagcaga ccaatggaga gcggagttgt ccaggtacca ggtggtagag   1440
attgrtccct tgtcagtagc cccaacaaca ggnaaaaggc cagaaataaa acaacactcc   1500
agacaaaaaa gaggcattgg aatagggctg ttcttcttgg gtcttctcag tgcagctggc   1560
agtacaatgg gcgcagcgtc aatagcgctg acggcacaga ccaggaattt gytccatggt   1620
attgtacaac agcaggccaa tctgctgcaa gccatagaga cacagcaaca tctgctacag   1680
ctctcggtct ggggagtaaa acaactccag gcaagaatgc ttgcagtcga agtaccta    1740 agagatcaac aactattgag cctctggggt tgtgctgaca aggtgacctg tcacactacg   1800
gtgccttgga taattcctg ggtaaacttc acgcaaacat gtgcaaagaa cagcagtgat   1860
atacaatgta tttgggaaaa tatgacatgg caagaatggg acagattagt acagaattca   1920
acaggacaga tatataatat cttacaaata gcacatgagc aacaagagag aaataaaaag   1980
gaattatatg aactagacaa atggagctca ttatggaatt ggtttgacat aacacaatgg   2040
ctatggtata taaaaatatt tattatgata gtaggagcta ttgtaggact aagaattttg   2100
cttgtattag ttagttgctt aagaaaggtt aggcagggat atcatcctct gtcatttcag   2160
atccctaccc aaaaccagca ggatccagag cagccagaag aaataagaga agaaggtgga   2220
agaaaagaca ggatcaggtg gagggccttg cagcacgggt tcttcgcact cttgtgggtg   2280
gacctgacga gcataatcca gtggatctac cagatctgca gaacctgtct cttgaacctt   2340
tgggcagtcc tccaacacct ctgcagaatt actttcagac tgtgcaacca tctggagaac   2400
aatctcagca ccctctggac aataatcaga actgagatca ttaagaacat tgacagactt   2460
```

-continued

```
gctatttggg taggggaaaa acagatagc atacttctag ctctccaaac tatagtcaga    2520
atcataaggg aagtacctag gcgcatcaga caagggttgg aaattgcatt aaattaa      2577
```

<210> SEQ ID NO 12
<211> LENGTH: 858
<212> TYPE: PRT
<213> ORGANISM: Simian immunodeficiency virus
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (538)..(538)
<223> OTHER INFORMATION: Xaa can be any naturally occurring amino acid

<400> SEQUENCE: 12

Met Arg Lys Pro Ile His Ile Ile Trp Gly Leu Ala Leu Leu Ile Gln
1               5                   10                  15

Phe Ile Glu Lys Gly Thr Asn Glu Asp Tyr Val Thr Val Phe Tyr Gly
            20                  25                  30

Val Pro Val Trp Arg Asn Ala Thr Pro Thr Leu Phe Cys Ala Thr Asn
        35                  40                  45

Ala Ser Met Thr Ser Thr Glu Val His Asn Val Trp Ala Thr Thr Ser
    50                  55                  60

Cys Val Pro Ile Asp Pro Asp Pro Ile Val Arg Leu Asn Thr Ser
65                  70                  75                  80

Val Trp Phe Asn Ala Tyr Lys Asn Tyr Met Val Glu Ser Met Thr Glu
                85                  90                  95

Asp Met Xaa Gln Leu Phe Gln Gln Ser His Lys Pro Cys Val Lys Leu
            100                 105                 110

Thr Pro Met Cys Ile Lys Met Asn Cys Thr Gly Tyr Asn Gly Thr Pro
        115                 120                 125

Thr Thr Pro Ser Thr Thr Thr Ser Thr Val Thr Pro Lys Thr Thr Thr
    130                 135                 140

Pro Ile Val Asp Gly Met Lys Leu Gln Glu Cys Asn Phe Asn Gln Ser
145                 150                 155                 160

Thr Gly Phe Lys Asp Lys Lys Gln Lys Met Lys Ala Ile Phe Tyr Lys
                165                 170                 175

Gly Asp Leu Met Lys Cys Gln Asp Asn Asn Glu Thr Asn Cys Tyr Tyr
            180                 185                 190

Leu Trp His Cys Asn Thr Thr Thr Ile Thr Gln Ser Cys Glu Lys Ser
        195                 200                 205

Thr Phe Glu Pro Ile Pro Ile His Tyr Cys Ala Pro Ala Gly Tyr Ala
    210                 215                 220

Ile Leu Arg Cys Glu Asp Glu Asp Phe Thr Gly Val Gly Met Cys Lys
225                 230                 235                 240

Asn Val Ser Val Val His Cys Thr His Gly Ile Ser Pro Met Val Ala
                245                 250                 255

Thr Trp Leu Leu Leu Asn Gly Thr Tyr Gln Thr Asn Thr Ser Val Val
            260                 265                 270

Met Asn Gly Arg Lys Asn Glu Ser Val Leu Val Arg Phe Gly Lys Glu
        275                 280                 285

Phe Glu Asn Leu Thr Ile Thr Cys Ile Arg Pro Gly Asn Arg Thr Val

-continued

```
                290                 295                 300
Arg Asn Leu Gln Ile Gly Pro Gly Met Thr Phe Tyr Asn Val Glu Ile
305                 310                 315                 320

Ala Thr Gly Asp Thr Arg Lys Ala Phe Cys Thr Val Asn Lys Thr Leu
                325                 330                 335

Trp Glu Gln Ala Arg Asn Lys Thr Glu His Val Leu Ala Glu His Trp
                340                 345                 350

Lys Lys Val Asp Asn Lys Thr Asn Ala Lys Thr Ile Trp Thr Phe Gln
                355                 360                 365

Asp Gly Asp Pro Glu Val Lys Val His Trp Phe Asn Cys Gln Gly Glu
                370                 375                 380

Phe Phe Tyr Cys Asp Ile Thr Pro Trp Phe Asn Ala Thr Tyr Thr Gly
385                 390                 395                 400

Asn Leu Ile Thr Asn Gly Ala Leu Ile Ala His Cys Arg Ile Lys Gln
                405                 410                 415

Ile Val Asn His Trp Gly Ile Val Ser Lys Gly Ile Tyr Leu Ala Pro
                420                 425                 430

Arg Arg Gly Asn Val Ser Cys Thr Ser Ser Ile Thr Gly Ile Met Leu
                435                 440                 445

Glu Gly Gln Ile Tyr Asn Glu Thr Val Lys Val Ser Pro Ala Ala Arg
450                 455                 460

Val Ala Asp Gln Trp Arg Ala Glu Leu Ser Arg Tyr Gln Val Val Glu
465                 470                 475                 480

Ile Xaa Pro Leu Ser Val Ala Pro Thr Thr Gly Lys Arg Pro Glu Ile
                485                 490                 495

Lys Gln His Ser Arg Gln Lys Arg Gly Ile Gly Ile Gly Leu Phe Phe
                500                 505                 510

Leu Gly Leu Leu Ser Ala Ala Gly Ser Thr Met Gly Ala Ala Ser Ile
                515                 520                 525

Ala Leu Thr Ala Gln Thr Arg Asn Leu Xaa His Gly Ile Val Gln Gln
                530                 535                 540

Gln Ala Asn Leu Leu Gln Ala Ile Glu Thr Gln Gln His Leu Leu Gln
545                 550                 555                 560

Leu Ser Val Trp Gly Val Lys Gln Leu Gln Ala Arg Met Leu Ala Val
                565                 570                 575

Glu Lys Tyr Leu Arg Asp Gln Gln Leu Leu Ser Leu Trp Gly Cys Ala
                580                 585                 590

Asp Lys Val Thr Cys His Thr Thr Val Pro Trp Asn Asn Ser Trp Val
                595                 600                 605

Asn Phe Thr Gln Thr Cys Ala Lys Asn Ser Ser Asp Ile Gln Cys Ile
                610                 615                 620

Trp Glu Asn Met Thr Trp Gln Glu Trp Asp Arg Leu Val Gln Asn Ser
625                 630                 635                 640

Thr Gly Gln Ile Tyr Asn Ile Leu Gln Ile Ala His Glu Gln Gln Glu
                645                 650                 655

Arg Asn Lys Lys Glu Leu Tyr Glu Leu Asp Lys Trp Ser Ser Leu Trp
                660                 665                 670

Asn Trp Phe Asp Ile Thr Gln Trp Leu Trp Tyr Ile Lys Ile Phe Ile
                675                 680                 685

Met Ile Val Gly Ala Ile Val Gly Leu Arg Ile Leu Leu Val Leu Val
                690                 695                 700

Ser Cys Leu Arg Lys Val Arg Gln Gly Tyr His Pro Leu Ser Phe Gln
705                 710                 715                 720
```

```
Ile Pro Thr Gln Asn Gln Gln Asp Pro Glu Gln Pro Glu Glu Ile Arg
                725                 730                 735

Glu Glu Gly Gly Arg Lys Asp Arg Ile Arg Trp Arg Ala Leu Gln His
            740                 745                 750

Gly Phe Phe Ala Leu Leu Trp Val Asp Leu Thr Ser Ile Ile Gln Trp
        755                 760                 765

Ile Tyr Gln Ile Cys Arg Thr Cys Leu Leu Asn Leu Trp Ala Val Leu
    770                 775                 780

Gln His Leu Cys Arg Ile Thr Phe Arg Leu Cys Asn His Leu Glu Asn
785                 790                 795                 800

Asn Leu Ser Thr Leu Trp Thr Ile Ile Arg Thr Glu Ile Ile Lys Asn
                805                 810                 815

Ile Asp Arg Leu Ala Ile Trp Val Gly Glu Lys Thr Asp Ser Ile Leu
            820                 825                 830

Leu Ala Leu Gln Thr Ile Val Arg Ile Ile Arg Glu Val Pro Arg Arg
        835                 840                 845

Ile Arg Gln Gly Leu Glu Ile Ala Leu Asn
    850                 855

<210> SEQ ID NO 13
<211> LENGTH: 2589
<212> TYPE: DNA
<213> ORGANISM: Human immunodeficiency virus type 2

<400> SEQUENCE: 13
atgatgtcta gtagaaatca gctgcttgtt actatcttac tagctagtgc ttgcttagta    60
tattgtaaac aatatgtgac tgttttttat ggcgtgccag catggaaaaa tgcatccatt   120
cccctctttt gtgcaaccaa aaatagagat acttggggaa ccatacagtg cttaccagac   180
aatgatgatt atcaggaaat agctttgaat gtgacagagg ctttcgatgc atgggataat   240
acagtaacag aacaagcagt agaagatgtc tggagactat ttgagacatc aataaaacca   300
tgtgtcaagt taacaccttt atgtatagca atgaagtgta gcaacataag cacagagagc   360
acaaccacat ccccgagccc agggagcaca ctcaaacccc tgataaatga gagcgatcca   420
tgcataaagg cagacaactg ccccagggga ctaggggatg aagagatggt caattgtcgg   480
ttcaacatga caggattaca gagagataag ccaaaacagt ataatgaaac atggtactca   540
aaagatgtgg tttgtgaacc atttaacacc accacaaacc agaccaggtg ttacatgaac   600
cattgcaaca catcagtcat cacagagtca tgtgataagc actattggga tgctataagg   660
tttagatact gtgcaccacc tggttacgcc ctactaagat gcgatgatat caattattca   720
ggctttgcac ccaattgctc taagtagta gctgctacat gcacaaggat gatggagacg   780
caaacttcta cttggtttgg ctttaatggc actagggcag aaaatagaac atatatctat   840
tggcatggta gagataatag aactatcatc agcttaaaca acattataa tcttactatg   900 cattgtaaga ggccaggaaa taagacagtt gtaccaataa cacttatgtc agggttaata   960
tttcactccc agccaatcaa taaagaccc agacaagcat ggtgctggtt caaaggcgaa  1020
tggaggaaag ccatgcagga ggtgaaggaa acccttgtaa acatcccag gtataaagga  1080 accaatgaca caaaccaaat taactttaca aaaccaggaa gaggctcaga tgcagaagtg  1140
gtatatatgt ggactaactg cagaggagaa tttctccatt gcaacatgac ttggttcctc  1200 aattgggtgaa aaacaaaac gggtcaggaa cagcacaatt atgcaccgtg ccatataaag  1260
caaataatta atatctggca caaagcaggg aaaaatgtat atttgcctcc tagggaagga  1320
```

-continued

```
gagttgacct gcaactcaac agtaaccagc ttgattgcta acattgacac ggatggcaac      1380
cagacaaata ttacctttag tgcagaggtg cagaactat  accgattaga attgggggat      1440
tataaattag tagagataac accaattggc ttcgcaccta catcagaaag gagatactcc      1500
tctactccaa ggaggaataa agaggtgtg  ttcgtgctag ggttcttagg ttttctcgcg      1560
acagcaggtt ctgcaatggg cacggcagct taacgctgt  ctgctcagtc tcggactttta     1620 ttggccggga tagtgcagca acagcaacag ctgttggacg tggtcaagag acaacaggaa      1680
atgttgcgac tgaccgtctg ggaacgaaa  aatctccagg caagagtcac tgctatcgag      1740
aaatacttaa aggaccaggc gcggctaaat tcatggggat gtgcatttag acaagtctgc      1800
cacactactg taccatgggt aaataactcc ttaaaacctg attgggacaa catgacgtgg      1860
caagagtggg aacaacaagt ccgttaccta gaggcaaata tcagtgaaca gttagaacgg      1920
gcacaaattc agcaagaaaa gaatacgtat gaactacaaa aattaaatag ctgggatgtt      1980
tttaccaact ggcttgactt aaccgcctgg gtcaagtata ttcaatatgg agtttatata     2040
atagtaggaa tagtagctct tagaatagta atatatgtag tgcaaatgtt aagtagactc      2100
aggaagggct ataggcctgt tttctcctcc cctcccggtt acatccaaca gatccatatc      2160
cacaaggacc aggaacagcc aaccagagga gaaacagaag aagacgttgg agacaacgtt      2220
ggggacagat tgtggccctg gccgatcgca tatttacatt tcctgatcca cctgctagct      2280
cgcctcttga tcgggctgta cagcatctgc agggacttac tatccaggat ctccccgatc      2340
ctccaaccga tcttccggag tcttcagaga gcgctgacaa caatcaggga ctggctgaga      2400
cttaaagcag cctacctgca gtatgggtgc gagtggatcc aagaagcgtt ccgggccttt      2460
gcaaggattg cgagagagac tcttacaaac acctggagag acttgtgggg ggcagtgcag      2520
tgggtcggga ggaggatact cgcagtccca aggaggatca ggcaggggc  agaaattgcc      2580 ctcctgtga                                                             2589
```

<210> SEQ ID NO 14
<211> LENGTH: 862
<212> TYPE: PRT
<213> ORGANISM: Human immunodeficiency virus type 2

<400> SEQUENCE: 14

```
Met Met Ser Ser Arg Asn Gln Leu Leu Val Thr Ile Leu Leu Ala Ser
1               5                   10                  15

Ala Cys Leu Val Tyr Cys Lys Gln Tyr Val Thr Val Phe Tyr Gly Val
                20                  25                  30

Pro Ala Trp Lys Asn Ala Ser Ile Pro Leu Phe Cys Ala Thr Lys Asn
            35                  40                  45

Arg Asp Thr Trp Gly Thr Ile Gln Cys Leu Pro Asp Asn Asp Asp Tyr
        50                  55                  60

Gln Glu Ile Ala Leu Asn Val Thr Glu Ala Phe Asp Ala Trp Asp Asn
65                  70                  75                  80

Thr Val Thr Glu Gln Ala Val Glu Asp Val Trp Arg Leu Phe Glu Thr
                85                  90                  95

Ser Ile Lys Pro Cys Val Lys Leu Thr Pro Leu Cys Ile Ala Met Lys
            100                 105                 110

Cys Ser Asn Ile Ser Thr Glu Ser Thr Thr Thr Ser Pro Ser Pro Gly
        115                 120                 125

Ser Thr Leu Lys Pro Leu Ile Asn Glu Ser Asp Pro Cys Ile Lys Ala
    130                 135                 140
```

```
Asp Asn Cys Pro Arg Gly Leu Gly Asp Glu Glu Met Val Asn Cys Arg
145                 150                 155                 160

Phe Asn Met Thr Gly Leu Gln Arg Asp Lys Pro Lys Gln Tyr Asn Glu
            165                 170                 175

Thr Trp Tyr Ser Lys Asp Val Val Cys Glu Pro Phe Asn Thr Thr Thr
                180                 185                 190

Asn Gln Thr Arg Cys Tyr Met Asn His Cys Asn Thr Ser Val Ile Thr
            195                 200                 205

Glu Ser Cys Asp Lys His Tyr Trp Asp Ala Ile Arg Phe Arg Tyr Cys
        210                 215                 220

Ala Pro Pro Gly Tyr Ala Leu Leu Arg Cys Asp Asp Ile Asn Tyr Ser
225                 230                 235                 240

Gly Phe Ala Pro Asn Cys Ser Lys Val Val Ala Ala Thr Cys Thr Arg
                245                 250                 255

Met Met Glu Thr Gln Thr Ser Thr Trp Phe Gly Phe Asn Gly Thr Arg
            260                 265                 270

Ala Glu Asn Arg Thr Tyr Ile Tyr Trp His Gly Arg Asp Asn Arg Thr
        275                 280                 285

Ile Ile Ser Leu Asn Lys His Tyr Asn Leu Thr Met His Cys Lys Arg
290                 295                 300

Pro Gly Asn Lys Thr Val Val Pro Ile Thr Leu Met Ser Gly Leu Ile
305                 310                 315                 320

Phe His Ser Gln Pro Ile Asn Lys Arg Pro Arg Gln Ala Trp Cys Trp
                325                 330                 335

Phe Lys Gly Glu Trp Arg Lys Ala Met Gln Glu Val Lys Glu Thr Leu
            340                 345                 350

Val Lys His Pro Arg Tyr Lys Gly Thr Asn Asp Thr Asn Gln Ile Asn
        355                 360                 365

Phe Thr Lys Pro Gly Arg Gly Ser Asp Ala Glu Val Val Tyr Met Trp
370                 375                 380

Thr Asn Cys Arg Gly Glu Phe Leu His Cys Asn Met Thr Trp Phe Leu
385                 390                 395                 400

Asn Trp Val Glu Asn Lys Thr Gly Gln Glu Gln His Asn Tyr Ala Pro
                405                 410                 415

Cys His Ile Lys Gln Ile Ile Asn Ile Trp His Lys Ala Gly Lys Asn
            420                 425                 430

Val Tyr Leu Pro Pro Arg Glu Gly Glu Leu Thr Cys Asn Ser Thr Val
        435                 440                 445

Thr Ser Leu Ile Ala Asn Ile Asp Thr Asp Gly Asn Gln Thr Asn Ile
450                 455                 460

Thr Phe Ser Ala Glu Val Ala Glu Leu Tyr Arg Leu Glu Leu Gly Asp
465                 470                 475                 480

Tyr Lys Leu Val Glu Ile Thr Pro Ile Gly Phe Ala Pro Thr Ser Glu
                485                 490                 495

Arg Arg Tyr Ser Ser Thr Pro Arg Asn Lys Arg Gly Val Phe Val
            500                 505                 510

Leu Gly Phe Leu Gly Phe Leu Ala Thr Ala Gly Ser Ala Met Gly Thr
        515                 520                 525

Ala Ala Leu Thr Leu Ser Ala Gln Ser Arg Thr Leu Leu Ala Gly Ile
530                 535                 540

Val Gln Gln Gln Gln Leu Leu Asp Val Val Lys Arg Gln Gln Glu
545                 550                 555                 560
```

```
Met Leu Arg Leu Thr Val Trp Gly Thr Lys Asn Leu Gln Ala Arg Val
                565                 570                 575
Thr Ala Ile Glu Lys Tyr Leu Lys Asp Gln Ala Arg Leu Asn Ser Trp
            580                 585                 590
Gly Cys Ala Phe Arg Gln Val Cys His Thr Thr Val Pro Trp Val Asn
        595                 600                 605
Asn Ser Leu Lys Pro Asp Trp Asp Asn Met Thr Trp Gln Glu Trp Glu
    610                 615                 620
Gln Gln Val Arg Tyr Leu Glu Ala Asn Ile Ser Glu Gln Leu Glu Arg
625                 630                 635                 640
Ala Gln Ile Gln Gln Glu Lys Asn Thr Tyr Glu Leu Gln Lys Leu Asn
                645                 650                 655
Ser Trp Asp Val Phe Thr Asn Trp Leu Asp Leu Thr Ala Trp Val Lys
            660                 665                 670
Tyr Ile Gln Tyr Gly Val Tyr Ile Val Gly Ile Val Ala Leu Arg
        675                 680                 685
Ile Val Ile Tyr Val Val Gln Met Leu Ser Arg Leu Arg Lys Gly Tyr
    690                 695                 700
Arg Pro Val Phe Ser Ser Pro Gly Tyr Ile Gln Gln Ile His Ile
705                 710                 715                 720
His Lys Asp Gln Glu Gln Pro Thr Arg Gly Glu Thr Glu Glu Asp Val
                725                 730                 735
Gly Asp Asn Val Gly Asp Arg Leu Trp Pro Trp Pro Ile Ala Tyr Leu
            740                 745                 750
His Phe Leu Ile His Leu Leu Ala Arg Leu Leu Ile Gly Leu Tyr Ser
        755                 760                 765
Ile Cys Arg Asp Leu Leu Ser Arg Ile Ser Pro Ile Leu Gln Pro Ile
    770                 775                 780
Phe Arg Ser Leu Gln Arg Ala Leu Thr Thr Ile Arg Asp Trp Leu Arg
785                 790                 795                 800
Leu Lys Ala Ala Tyr Leu Gln Tyr Gly Cys Glu Trp Ile Gln Glu Ala
                805                 810                 815
Phe Arg Ala Phe Ala Arg Ile Ala Arg Glu Thr Leu Thr Asn Thr Trp
            820                 825                 830
Arg Asp Leu Trp Gly Ala Val Gln Trp Val Gly Arg Arg Ile Leu Ala
        835                 840                 845
Val Pro Arg Arg Ile Arg Gln Gly Ala Glu Ile Ala Leu Leu
    850                 855                 860

<210> SEQ ID NO 15
<211> LENGTH: 2640
<212> TYPE: DNA
<213> ORGANISM: Simian immunodeficiency virus

<400> SEQUENCE: 15
atgggatgtc ttgggaatca gctgcttatc gccatcttgc ttttaagtgt ctatgggatc      60
tattgtactc tatatgtcac agtctttat ggtgtaccag cttggaggaa tgcgacaatt      120
ccctcttttt gtgcaaccaa gaatagggat acttggggaa caactcagtg cctaccagat     180
aatggtgatt attcagaagt ggcccttaat gttacagaaa gctttgatgc ctggaataat     240
acagtcacag aacaggcaat agaggatgta tggcaactct ttgagacctc aataaagcct     300
tgtgtaaaat tatccccatt atgcattact atgagatgca ataaaagtga gacagataga     360
tggggattga caaatcaat aacaacaaca gcatcaacaa catcaacgac agcatcagca     420
```

| | |
|---|---|
| aaagtagaca tggtcaatga gactagttct tgtatagccc aggataattg cacaggcttg | 480 |
| gaacaagagc aaatgataag ctgtaaattc aacatgacag ggttaaaaag agacaagaaa | 540 |
| aaagagtaca atgaaacttg gtactctgca gatttggtat gtgaacaagg aataacact | 600 |
| ggtaatgaaa gtagatgtta catgaaccac tgtaacactt ctgttatcca agagtcttgt | 660 |
| gacaaacatt attgggatgc tattagattt aggtattgtg cacctccagg ttatgctttg | 720 |
| cttagatgta atgacacaaa ttattcaggc tttatgccta aatgttctaa ggtggtggtc | 780 |
| tcttcatgca caaggatgat ggagacacag acttctactt ggtttggctt taatggaact | 840 |
| agagcagaaa atagaactta tatttactgg catggtaggg ataataggac tataattagt | 900 |
| ttaaataagt attataatct aacaatgaaa tgtagaagac caggaaataa acagttttta | 960 |
| ccagtcacca ttatgtctgg attggttttc cactcacaac caatcaatga taggccaaag | 1020 |
| caggcatggt gttggtttgg aggaaaatgg aaggatgcaa taaagaggt gaagcagacc | 1080 |
| attgtcaaac atcccaggta tactggaact aacaatactg ataaaatcaa tttgacggct | 1140 |
| cctggaggag gagatccgga agttaccttc atgtggacaa attgcagagg agagttcctc | 1200 |
| tactgtaaaa tgaattggtt tctaaattgg gtagaagata ggaatacagc taaccagaag | 1260 |
| ccaaaggaac agcataaaag gaattacgtg ccatgtcata ttagacaaat aatcaacact | 1320 |
| tggcataaag taggcaaaaa tgtttatttg cctccaagag agggagacct cacgtgtaac | 1380 |
| tccacagtga ccagtctcat agcaaacata gattggattg atgaaaccaa actaatatc | 1440 |
| accatgagtg cagaggtggc agaactgtat cgattggaat gggagattta aaattagta | 1500 |
| gagatcactc caattggctt ggcccccaca gatgtgaaga ggtacactac tggtggcacc | 1560 |
| tcaagaaata aagagggggt cttttgtgcta gggttcttgg gttttctcgc aacggcaggt | 1620 |
| tctgcaatgg gcgcggcgtc gttgacgctg accgctcagt cccgaacttt attggctggg | 1680 |
| atagtgcagc aacagcaaca gctgttggac gtggtcaaga gacaacaaga attgttgcga | 1740 |
| ctgaccgtct ggggaacaaa gaacctccag actagggtca ctgccatcga agtacttaa | 1800 |
| aaggaccagg cgcagctgaa tgcttgggga tgtgcgttta gacaagtctg ccacactact | 1860 |
| gtaccatggc caaatgcaag tctaacacca aagtggaaca atgagacttg gcaagagtgg | 1920 |
| gagcgaaagg ttgacttctt ggaagaaaat ataacagccc tcctagagga ggcacaaatt | 1980 |
| caacaagaga agaacatgta tgaattacaa aagttgaata gctgggatgt gtttggcaat | 2040 |
| tggtttgacc ttgcttcttg gataaagtat atacaatatg gagtttatat agttgtagga | 2100 |
| gtaatactgt taagaatagt gatctatata gtacaaatgc tagctaagtt aaggcagggg | 2160 |
| tataggccag tgttctcttc cccaccctct tatttccagc agacccatat ccaacaggac | 2220 |
| ccggcactgc caaccagaga aggcaaagaa agagacggtg gagaaggcgg tgcaacagc | 2280 |
| tcctggcctt ggcagataga atatattcat ttcctgatcc gccaactgat acgcctcttg | 2340 |
| acttggctat tcagcaactg cagaaccttg ctatcgagag tataccagat cctccaacca | 2400 |
| atactccaga ggctctctgc gaccctacag aggattcgag aagtcctcag gactgaactg | 2460 |
| acctacctac aatatgggtg gagctatttc catgaggcgg tccaggccgt ctggagatct | 2520 |
| gcgacagaga ctcttgcggg cgcgtgggga gacttatggg agactcttag gagaggtgga | 2580 |
| agatggatac tcgcaatccc caggaggatt agacaagggc ttgagctcac tctcttgtga | 2640 |

<210> SEQ ID NO 16
<211> LENGTH: 879
<212> TYPE: PRT
<213> ORGANISM: Simian immunodeficiency virus

<400> SEQUENCE: 16

```
Met Gly Cys Leu Gly Asn Gln Leu Leu Ile Ala Ile Leu Leu Leu Ser
1               5                   10                  15

Val Tyr Gly Ile Tyr Cys Thr Leu Tyr Val Thr Val Phe Tyr Gly Val
            20                  25                  30

Pro Ala Trp Arg Asn Ala Thr Ile Pro Leu Phe Cys Ala Thr Lys Asn
        35                  40                  45

Arg Asp Thr Trp Gly Thr Thr Gln Cys Leu Pro Asp Asn Gly Asp Tyr
    50                  55                  60

Ser Glu Val Ala Leu Asn Val Thr Glu Ser Phe Asp Ala Trp Asn Asn
65                  70                  75                  80

Thr Val Thr Glu Gln Ala Ile Glu Asp Val Trp Gln Leu Phe Glu Thr
                85                  90                  95

Ser Ile Lys Pro Cys Val Lys Leu Ser Pro Leu Cys Ile Thr Met Arg
            100                 105                 110

Cys Asn Lys Ser Glu Thr Asp Arg Trp Gly Leu Thr Lys Ser Ile Thr
        115                 120                 125

Thr Thr Ala Ser Thr Thr Ser Thr Thr Ala Ser Ala Lys Val Asp Met
    130                 135                 140

Val Asn Glu Thr Ser Ser Cys Ile Ala Gln Asp Asn Cys Thr Gly Leu
145                 150                 155                 160

Glu Gln Glu Gln Met Ile Ser Cys Lys Phe Asn Met Thr Gly Leu Lys
                165                 170                 175

Arg Asp Lys Lys Lys Glu Tyr Asn Glu Thr Trp Tyr Ser Ala Asp Leu
            180                 185                 190

Val Cys Glu Gln Gly Asn Asn Thr Gly Asn Glu Ser Arg Cys Tyr Met
        195                 200                 205

Asn His Cys Asn Thr Ser Val Ile Gln Glu Ser Cys Asp Lys His Tyr
    210                 215                 220

Trp Asp Ala Ile Arg Phe Arg Tyr Cys Ala Pro Pro Gly Tyr Ala Leu
225                 230                 235                 240

Leu Arg Cys Asn Asp Thr Asn Tyr Ser Gly Phe Met Pro Lys Cys Ser
                245                 250                 255

Lys Val Val Val Ser Ser Cys Thr Arg Met Met Glu Thr Gln Thr Ser
            260                 265                 270

Thr Trp Phe Gly Phe Asn Gly Thr Arg Ala Glu Asn Arg Thr Tyr Ile
        275                 280                 285

Tyr Trp His Gly Arg Asp Asn Arg Thr Ile Ile Ser Leu Asn Lys Tyr
    290                 295                 300

Tyr Asn Leu Thr Met Lys Cys Arg Arg Pro Gly Asn Lys Thr Val Leu
305                 310                 315                 320

Pro Val Thr Ile Met Ser Gly Leu Val Phe His Ser Gln Pro Ile Asn
                325                 330                 335

Asp Arg Pro Lys Gln Ala Trp Cys Trp Phe Gly Gly Lys Trp Lys Asp
            340                 345                 350

Ala Ile Lys Glu Val Lys Gln Thr Ile Val Lys His Pro Arg Tyr Thr
        355                 360                 365

Gly Thr Asn Asn Thr Asp Lys Ile Asn Leu Thr Ala Pro Gly Gly Gly
    370                 375                 380

Asp Pro Glu Val Thr Phe Met Trp Thr Asn Cys Arg Gly Glu Phe Leu
385                 390                 395                 400

Tyr Cys Lys Met Asn Trp Phe Leu Asn Trp Val Glu Asp Arg Asn Thr
```

-continued

```
                405                 410                 415
Ala Asn Gln Lys Pro Lys Glu Gln His Lys Arg Asn Tyr Val Pro Cys
        420                 425                 430

His Ile Arg Gln Ile Ile Asn Thr Trp His Lys Val Gly Lys Asn Val
        435                 440                 445

Tyr Leu Pro Pro Arg Glu Gly Asp Leu Thr Cys Asn Ser Thr Val Thr
    450                 455                 460

Ser Leu Ile Ala Asn Ile Asp Trp Ile Asp Gly Asn Gln Thr Asn Ile
465                 470                 475                 480

Thr Met Ser Ala Glu Val Ala Glu Leu Tyr Arg Leu Glu Leu Gly Asp
                485                 490                 495

Tyr Lys Leu Val Glu Ile Thr Pro Ile Gly Leu Ala Pro Thr Asp Val
        500                 505                 510

Lys Arg Tyr Thr Thr Gly Gly Thr Ser Arg Asn Lys Arg Gly Val Phe
        515                 520                 525

Val Leu Gly Phe Leu Gly Phe Leu Ala Thr Ala Gly Ser Ala Met Gly
    530                 535                 540

Ala Ala Ser Leu Thr Leu Thr Ala Gln Ser Arg Thr Leu Leu Ala Gly
545                 550                 555                 560

Ile Val Gln Gln Gln Gln Leu Leu Asp Val Val Lys Arg Gln Gln
                565                 570                 575

Glu Leu Leu Arg Leu Thr Val Trp Gly Thr Lys Asn Leu Gln Thr Arg
            580                 585                 590

Val Thr Ala Ile Glu Lys Tyr Leu Lys Asp Gln Ala Gln Leu Asn Ala
        595                 600                 605

Trp Gly Cys Ala Phe Arg Gln Val Cys His Thr Thr Val Pro Trp Pro
    610                 615                 620

Asn Ala Ser Leu Thr Pro Lys Trp Asn Asn Glu Thr Trp Gln Glu Trp
625                 630                 635                 640

Glu Arg Lys Val Asp Phe Leu Glu Glu Asn Ile Thr Ala Leu Leu Glu
                645                 650                 655

Glu Ala Gln Ile Gln Gln Glu Lys Asn Met Tyr Glu Leu Gln Lys Leu
            660                 665                 670

Asn Ser Trp Asp Val Phe Gly Asn Trp Phe Asp Leu Ala Ser Trp Ile
        675                 680                 685

Lys Tyr Ile Gln Tyr Gly Val Tyr Ile Val Gly Val Ile Leu Leu
    690                 695                 700

Arg Ile Val Ile Tyr Ile Val Gln Met Leu Ala Lys Leu Arg Gln Gly
705                 710                 715                 720

Tyr Arg Pro Val Phe Ser Ser Pro Ser Tyr Phe Gln Gln Thr His
                725                 730                 735

Ile Gln Gln Asp Pro Ala Leu Pro Thr Arg Glu Gly Lys Glu Arg Asp
            740                 745                 750

Gly Gly Glu Gly Gly Gly Asn Ser Ser Trp Pro Trp Gln Ile Glu Tyr
        755                 760                 765

Ile His Phe Leu Ile Arg Gln Leu Ile Arg Leu Leu Thr Trp Leu Phe
    770                 775                 780

Ser Asn Cys Arg Thr Leu Leu Ser Arg Val Tyr Gln Ile Leu Gln Pro
785                 790                 795                 800

Ile Leu Gln Arg Leu Ser Ala Thr Leu Gln Arg Ile Arg Glu Val Leu
                805                 810                 815

Arg Thr Glu Leu Thr Tyr Leu Gln Tyr Gly Trp Ser Tyr Phe His Glu
            820                 825                 830
```

Ala Val Gln Ala Val Trp Arg Ser Ala Thr Glu Thr Leu Ala Gly Ala
        835                 840                 845

Trp Gly Asp Leu Trp Glu Thr Leu Arg Arg Gly Arg Trp Ile Leu
    850                 855                 860

Ala Ile Pro Arg Arg Ile Arg Gln Gly Leu Glu Leu Thr Leu Leu
865                 870                 875

<210> SEQ ID NO 17
<211> LENGTH: 2664
<212> TYPE: DNA
<213> ORGANISM: Simian immunodeficiency virus

<400> SEQUENCE: 17

| | | | | |
|---|---|---|---|---|
| atgggatgtc | ttgggaatca | gctgcttatc | gcgctcttgc | tagtaagtgt | tttagagatt | 60 |
| tgttgtgttc | aatatgtaac | agtattctat | ggtgtaccag | catggaagaa | tgcgacaatt | 120 |
| cccctcttct | gtgcaaccag | gaatagggac | acttggggaa | caacacaatg | cttgcctgat | 180 |
| aatgatgatt | actcagaatt | ggcagtcaat | atcacagagg | cttttgatgc | ttggaataat | 240 |
| acagtcacag | aacaagcaat | agaggatgtg | tggaacctct | tgaaacatc | cattaagccc | 300 |
| tgtgtaaaac | ttacccccact | atgtatagca | atgaggtgta | taaaactga | dacagatagg | 360 |
| tggggtttga | caggaagagc | agagacaaca | acaacagcga | atcaacaac | atcaacaaca | 420 |
| acaacaacag | taacaccaaa | ggtcataaat | gaaggtgatt | cttgcataaa | agataatagt | 480 |
| tgtgcaggct | ggaacagga | gcccatgata | ggttgtaaat | ttaacatgac | aggattaaag | 540 |
| agggacaaaa | agatagaata | taatgaaaca | tggtattcaa | gagatttaat | ctgtgagcag | 600 |
| tcagcaaatg | gaagtgagag | taaatgttac | atgcagcatt | gtaacaccag | tgttattcag | 660 |
| gaatcctgtg | acaagcatta | ttgggatgct | attagattta | gatactgtgc | accgccaggt | 720 |
| tatgctttgc | ttaggtgtaa | tgattcaaat | tattcaggct | tgctcctaa | atgttctaag | 780 |
| gtagtggttt | cttcatgcac | aagaatgatg | agacgcaaa | cctctacttg | gtttggcttc | 840 |
| aatggtacta | gggcagaaaa | tagaacatac | atttattggc | atggcaatag | taatagaacc | 900 |
| ataattagct | taaataagta | ttataatcta | caataagat | gtaaaagacc | aggaaataag | 960 |
| acagttttac | cagtcaccat | tatgtcaggg | ttggtcttcc | attcgcaaac | cataaatacg | 1020 |
| agaccaaaac | aggcctggtg | ctggtttgaa | ggaaactgga | gcaaggccat | ccaggaagtg | 1080 |
| aaggaaaccct | tggtcaaaca | tcccaggtat | acgggaacta | atgatactag | gaaaattaat | 1140 |
| ctaacagctc | cagcaagagg | aaatccagaa | gtcacttta | tgtggacaaa | ttgtcgagga | 1200 |
| gaattcttat | actgcaaaat | gaattggttt | ctcaattggg | tagaggacag | agaccaaaat | 1260 |
| agtaacagat | ggaaacaaca | aaaggagtca | gagcaaaga | agagaaatta | tgtgccatgt | 1320 |
| catattagac | aaataatcaa | cgcgtggcac | aaagtaggca | aaaatgtata | tttgcctcct | 1380 |
| agggaaggag | acctgacatg | taattccact | gtaactagtc | tcatagcaaa | gatagattgg | 1440 |
| atcaataaca | atgagaccaa | tatcaccatg | agtgcagagg | tggcagaact | gtatcgattg | 1500 |
| gagttgggag | attacaaatt | agtagagatt | actccaattg | gcttggcccc | cacaaatgta | 1560 |
| agaaggtaca | ccacaactgg | tgcctcaaga | aataagagag | ggtctttgt | gctagggttc | 1620 |
| ttgggttttc | tcgcgacagc | aggttctgca | atgggcgcgg | cgtcgctgac | gctgtcggct | 1680 |
| cagtcccgga | cttttgttggc | tgggatagtg | cagcaacagc | aacagctgtt | ggatgtggtc | 1740 |
| aagagacaac | aagaattgtt | gcgactgacc | gtctggggaa | ctaagaaacct | ccagactaga | 1800 |
| gtcactgcta | tcgagaagta | cctgaaggat | caggcgcggc | taaattcatg | ggatgtgct | 1860 |

-continued

```
tttaggcaag tctgtcacac tactgtacca tggccaaatg actcattggt gcctaattgg   1920
gacaatatga cttggcaaga gtgggaagga aaggttaact ccctagaggc aaatataact   1980
caattattag aagaagcaca aattcagcaa gaaagaata tgtatgaatt gcaaaaacta   2040
aatagctggg atatctttgg caattggttt gaccttactt cttggataag atatatacaa   2100
tatggtgtac taatagttt aggagtagta gggttaagaa tagtgatata tgtagtgcaa   2160
atgctagcta ggttaagaca gggttatagg ccagtgttct cttcccctcc cgcttatgtt   2220
cagcagatcc ctatccacaa ggaccaggaa ccgccaacca agaaggaga agaaggagaa   2280 ggtggagaca gaggtggcag cagatcttgg ccttggcaga tagaatatat tcatttccta   2340
atccgccaac tgatacgcct cttgacttgg ctattcagca gctgcaggga ttggctattg   2400
aggatctacc agatcctcca accagtgctc cagagactct caaggacgct gcaaagagtt   2460
cgtgaagtca tcagaattga aataacctac ctacaacatg ggtggagcta tttccaagaa   2520
gcagcacagg cgtggtggaa atttgcgcga gagactcttg cgagcgcgtg gagagacata   2580
tgggagactc tgggaagggt tggaagaggg atactcgcaa tccctaggcg cgtcaggcaa   2640
gggcttgagc tcactctctt gtga                                          2664
```

<210> SEQ ID NO 18
<211> LENGTH: 887
<212> TYPE: PRT
<213> ORGANISM: Simian immunodeficiency virus

<400> SEQUENCE: 18

```
Met Gly Cys Leu Gly Asn Gln Leu Leu Ile Ala Leu Leu Leu Val Ser
1               5                   10                  15

Val Leu Glu Ile Cys Cys Val Gln Tyr Val Thr Val Phe Tyr Gly Val
            20                  25                  30

Pro Ala Trp Lys Asn Ala Thr Ile Pro Leu Phe Cys Ala Thr Arg Asn
        35                  40                  45

Arg Asp Thr Trp Gly Thr Thr Gln Cys Leu Pro Asp Asn Asp Asp Tyr
    50                  55                  60

Ser Glu Leu Ala Val Asn Ile Thr Glu Ala Phe Asp Ala Trp Asn Asn
65                  70                  75                  80

Thr Val Thr Glu Gln Ala Ile Glu Asp Val Trp Asn Leu Phe Glu Thr
                85                  90                  95

Ser Ile Lys Pro Cys Val Lys Leu Thr Pro Leu Cys Ile Ala Met Arg
            100                 105                 110

Cys Asn Lys Thr Glu Thr Asp Arg Trp Gly Leu Thr Gly Arg Ala Glu
        115                 120                 125

Thr Thr Thr Thr Ala Lys Ser Thr Thr Ser Thr Thr Thr Thr Thr Val
    130                 135                 140

Thr Pro Lys Val Ile Asn Glu Gly Asp Ser Cys Ile Lys Asp Asn Ser
145                 150                 155                 160

Cys Ala Gly Leu Glu Gln Glu Pro Met Ile Gly Cys Lys Phe Asn Met
                165                 170                 175

Thr Gly Leu Lys Arg Asp Lys Lys Ile Glu Tyr Asn Glu Thr Trp Tyr
            180                 185                 190

Ser Arg Asp Leu Ile Cys Glu Gln Ser Ala Asn Gly Ser Glu Ser Lys
        195                 200                 205

Cys Tyr Met Gln His Cys Asn Thr Ser Val Ile Gln Glu Ser Cys Asp
    210                 215                 220
```

```
Lys His Tyr Trp Asp Ala Ile Arg Phe Arg Tyr Cys Ala Pro Pro Gly
225                 230                 235                 240

Tyr Ala Leu Leu Arg Cys Asn Asp Ser Asn Tyr Ser Gly Phe Ala Pro
            245                 250                 255

Lys Cys Ser Lys Val Val Ser Ser Cys Thr Arg Met Met Glu Thr
        260                 265                 270

Gln Thr Ser Thr Trp Phe Gly Phe Asn Gly Thr Arg Ala Glu Asn Arg
        275                 280                 285

Thr Tyr Ile Tyr Trp His Gly Asn Ser Asn Arg Thr Ile Ile Ser Leu
290                 295                 300

Asn Lys Tyr Tyr Asn Leu Thr Ile Arg Cys Lys Arg Pro Gly Asn Lys
305                 310                 315                 320

Thr Val Leu Pro Val Thr Ile Met Ser Gly Leu Val Phe His Ser Gln
                325                 330                 335

Thr Ile Asn Thr Arg Pro Lys Gln Ala Trp Cys Trp Phe Glu Gly Asn
            340                 345                 350

Trp Ser Lys Ala Ile Gln Glu Val Lys Glu Thr Leu Val Lys His Pro
        355                 360                 365

Arg Tyr Thr Gly Thr Asn Asp Thr Arg Lys Ile Asn Leu Thr Ala Pro
        370                 375                 380

Ala Arg Gly Asn Pro Glu Val Thr Phe Met Trp Thr Asn Cys Arg Gly
385                 390                 395                 400

Glu Phe Leu Tyr Cys Lys Met Asn Trp Phe Leu Asn Trp Val Glu Asp
                405                 410                 415

Arg Asp Gln Asn Ser Asn Arg Trp Lys Gln Gln Lys Glu Ser Glu Gln
            420                 425                 430

Lys Lys Arg Asn Tyr Val Pro Cys His Ile Arg Gln Ile Ile Asn Ala
        435                 440                 445

Trp His Lys Val Gly Lys Asn Val Tyr Leu Pro Pro Arg Glu Gly Asp
        450                 455                 460

Leu Thr Cys Asn Ser Thr Val Thr Ser Leu Ile Ala Lys Ile Asp Trp
465                 470                 475                 480

Ile Asn Asn Asn Glu Thr Asn Ile Thr Met Ser Ala Glu Val Ala Glu
                485                 490                 495

Leu Tyr Arg Leu Glu Leu Gly Asp Tyr Lys Leu Val Glu Ile Thr Pro
            500                 505                 510

Ile Gly Leu Ala Pro Thr Asn Val Arg Arg Tyr Thr Thr Gly Ala
        515                 520                 525

Ser Arg Asn Lys Arg Gly Val Phe Val Leu Gly Phe Leu Gly Phe Leu
530                 535                 540

Ala Thr Ala Gly Ser Ala Met Gly Ala Ala Ser Leu Thr Leu Ser Ala
545                 550                 555                 560

Gln Ser Arg Thr Leu Leu Ala Gly Ile Val Gln Gln Gln Gln Gln Leu
            565                 570                 575

Leu Asp Val Val Lys Arg Gln Gln Glu Leu Leu Arg Leu Thr Val Trp
        580                 585                 590

Gly Thr Lys Asn Leu Gln Thr Arg Val Thr Ala Ile Glu Lys Tyr Leu
        595                 600                 605

Lys Asp Gln Ala Arg Leu Asn Ser Trp Gly Cys Ala Phe Arg Gln Val
        610                 615                 620

Cys His Thr Thr Val Pro Trp Pro Asn Asp Ser Leu Val Pro Asn Trp
625                 630                 635                 640

Asp Asn Met Thr Trp Gln Glu Trp Glu Gly Lys Val Asn Phe Leu Glu
```

-continued

```
            645                 650                 655
Ala Asn Ile Thr Gln Leu Leu Glu Glu Ala Gln Ile Gln Gln Glu Lys
            660                 665                 670

Asn Met Tyr Glu Leu Gln Lys Leu Asn Ser Trp Asp Ile Phe Gly Asn
        675                 680                 685

Trp Phe Asp Leu Thr Ser Trp Ile Arg Tyr Ile Gln Tyr Gly Val Leu
        690                 695                 700

Ile Val Leu Gly Val Val Gly Leu Arg Ile Val Ile Tyr Val Val Gln
705                 710                 715                 720

Met Leu Ala Arg Leu Arg Gln Gly Tyr Arg Pro Val Phe Ser Ser Pro
                725                 730                 735

Pro Ala Tyr Val Gln Gln Ile Pro Ile His Lys Asp Gln Glu Pro Pro
                740                 745                 750

Thr Lys Glu Gly Glu Glu Gly Glu Gly Gly Asp Arg Gly Gly Ser Arg
                755                 760                 765

Ser Trp Pro Trp Gln Ile Glu Tyr Ile His Phe Leu Ile Arg Gln Leu
    770                 775                 780

Ile Arg Leu Leu Thr Trp Leu Phe Ser Ser Cys Arg Asp Trp Leu Leu
785                 790                 795                 800

Arg Ile Tyr Gln Ile Leu Gln Pro Val Leu Gln Arg Leu Ser Arg Thr
                805                 810                 815

Leu Gln Arg Val Arg Glu Val Ile Arg Ile Glu Ile Thr Tyr Leu Gln
                820                 825                 830

His Gly Trp Ser Tyr Phe Gln Glu Ala Ala Gln Ala Trp Trp Lys Phe
                835                 840                 845

Ala Arg Glu Thr Leu Ala Ser Ala Trp Arg Asp Ile Trp Glu Thr Leu
    850                 855                 860

Gly Arg Val Gly Arg Gly Ile Leu Ala Ile Pro Arg Arg Val Arg Gln
865                 870                 875                 880

Gly Leu Glu Leu Thr Leu Leu
                885
```

COMPOSITIONS AND METHODS FOR CONFORMATIONALLY STABILIZING PRIMATE IMMUNODEFICIENCY VIRUS ENVELOPE GLYCOPROTEIN TRIMERS

CROSS-REFERENCE TO RELATED APPLICATIONS

This application is the U.S. national phase of International Patent Application No. PCT/US2013/0052855, filed on 31 Jul. 2013, which claims the benefit of priority to U.S. Provisional Patent Application No. 61/742,139 filed Aug. 3, 2012, the entire content of each application is incorporated herein in their entirety by this reference.

STATEMENT OF RIGHTS

This invention was made with government support under grant numbers AI093256, AI067854, and AI024755 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 29, 2015, is named DFS-109_01_Sequence_Listing.txt and is 99,180 bytes in size.

BACKGROUND OF THE INVENTION

Human immunodeficiency viruses (HIVs) are responsible for the pandemic of acquired immunodeficiency syndrome (AIDS) and related viruses cause similar conditions in other primates (e.g., collectively known as primate immunodeficiency viruses (PIVs). The envelope (Env) glycoprotein trimer (i.e., a trimer of gp120/gp41 protomers that forms the representative "spikes" on the surface of PIV particles) of a PIV is a membrane-fusing machine that mediates virus entry into host cells (Wyatt and Sodroski (1998) *Science* 280: 1884-1888). Binding of the gp120 exterior envelope glycoprotein to CD4 and the chemokine receptor on target cells triggers conformational changes that allow the gp41 transmembrane envelope glycoprotein to fuse the viral and cell membranes. As the only virus-specific protein exposed on PIV particles or infected cell membrane, the envelope glycoprotein trimer represents the sole target for protective antibodies having neutralizing and/or other antiviral capabilities (Wyatt and Sodroski (1998) *Science* 280:1884-1888; Walker and Burton (2008) *Science* 320:760-764). Only about 10% of HIV-1-infected individuals generate broadly neutralizing antibodies (BNAbs), typically after 3-4 years of infection. Monoclonal antibodies that neutralize a broad range of HIV-1 variants have been derived from this subset of chronically infected humans. Some BNAbs passively protect monkeys from infection with viruses bearing HIV-1 Env, suggesting their potential utility in vaccine-elicited protection.

Attempts to elicit such protective antibodies having broad potency against divergent PIV species and/or strains have been unsuccessful to date, due to several factors. First, the structure of the envelope glycoproteins provides only a limited number of conserved sites accessible to antibodies. Second, antibodies must further target these limited epitopes with the correct angle-of-approach in order to bypass steric impediments (e.g., variable loops, glycans, and adjacent subunits) that interfere with antibody binding. Third, many candidate immunogens do not retain important neutralization epitopes in a stable manner. Even in cases where certain conformation-sensitive epitopes can be recognized by desired protective antibodies, these conformations are sampled in only a small percentage of the population of immunogen molecules at a given time due to the lability of the envelope glycoprotein trimer and dissociation of individual gp120 and gp41 subunits.

Indeed, a high percentage of the recently identified HIV-1-neutralizing monoclonal antibodies recognized Env epitopes in a quaternary structure- and/or N-linked carbohydrate-dependent manner that depends upon native envelope glycoprotein trimer structures. For example, the epitope for the broadly neutralizing human monoclonal antibody (mAb), b12, overlaps the CD4-binding site on gp120 and is present on monomeric gp120. However, b12 reacts far better with native, oligomeric gp120 than might be predicted from its monomer reactivity, which accounts for its unusually potent neutralization activity. Thus, the IgG1b12 epitope is oligomer-dependent, but not oligomer-specific. By contrast, many antibodies that are strongly reactive with CD4-binding site-related epitopes on monomeric gp120 fail to react with the native trimer and therefore do not neutralize primate immunodeficiency viruses.

Moreover, the rational design and modification of immunogens that overcome these hurdles has been hampered by a lack of structural information useful for generating soluble envelope glycoprotein trimers that faithfully mimic the native Env spike and function as effective immunogens for eliciting broadly protective antibodies. Although several crystal structures of monomeric HIV-1 gp120 core fragments in the CD4-bound state (Kwong et al. (1998) *Nature* 393:648-659; Huang et al. (2005) *Science* 310:1025-1028; Zhou et al. (2007) *Nature* 445:732-737; Huang et al. (2007) *Science* 317:1930-1934; Pancera et al. (2010) *Proc. Natl. Acad. Sci. USA* 107:1166-1171), trimeric gp41 ectodomain fragments in the post-fusion state (Weissenhorn et al. (1997) *Nature* 387:426-430; Chan et al. (1997) *Cell* 89:263-273; Buzon et al. (2010) *PLoS Pathog.* 6:e1000880), and unliganded monomeric gp120 core complexes from simian immunodeficiency virus (SIV) (Chen et al. (2005) *Nature* 433:834-841) have been determined at the atomic level, structural information is lacking on the unliganded state of gp120 and gp41 in the Env trimer and on the quaternary interactions that maintain the conformational integrity of the native trimer. Such information is critical for the rational design of conformationally stabilized quaternary PIV envelope glycoprotein trimers effective as immunogens for eliciting neutralizing responses (e.g., broadly neutralizing antibodies). Moreover, the currently defined gp120 and gp41 structures do not include a number of functionally important components (gp120 V1/V2 regions; gp41 fusion peptide, disulfide-bonded loop, transmembrane region and cytoplasmic tail; and glycans) that were artificially removed to facilitate crystallization. Although alternatives to X-ray crystallographic methods, such as cryo-electron microscopy (cryo-EM), have yielded electron density maps of purified Env variants at 18-30-Å resolution (Zhu et al. (2006) *Nature* 441:847-852; Zanetti et al. (2006) *PLoS Pathog.* 2:e83; Liu et al. (2008) *Nature* 455:109-113; White et al. (2010) *PLoS Pathog.* 6:e1001249; Wu et al. (2010) *Proc. Natl. Acad. Sci. USA* 107:18844-18849; Hu et al. (2011) *J. Virol.* 85:2741-2750), such models contradict each other and are insufficient for building an atomic model.

Accordingly, there is a great need to identify compositions and methods useful for generating stabilized PIV envelope glycoprotein trimers that can function effectively as immunogens for eliciting protective antibodies.

SUMMARY OF THE INVENTION

The present invention overcomes the longstanding difficulties in generating broadly neutralizing anti-primate immunodeficiency virus agents by providing stabilized envelope trimer complexes and polypeptides thereof that conformationally mimic the natural complexes and enhance immunogenicity.

In one aspect, a stabilized primate immunodeficiency virus (PIV) envelope polypeptide trimer complex is provided, wherein (a) each protomeric unit of the complex comprises a gp120 subunit and a gp41 subunit, or immunogenic fragments thereof, (b) one or more subunits of the complex comprises one or more mutated amino acid residues that increases the stability of the complex, and (c) the one or more mutated amino acid residues does not substantially alter the conformation of the native complex, in which the mutated amino acid residues are not altered. In one embodiment, the conformation of the native complex in which the mutated amino acid residues are not altered is the conformation shown in any one of FIGS. 1-17. In another embodiment, the one or more mutated residues comprise one or more pairs of residues that physically interact within the native complex. In still another embodiment, the positions of the mutated residues are selected from the group consisting of the residues listed in Tables 6-9 and combinations thereof. In yet another embodiment, the residue mutations are selected from the group consisting of cysteine-cysteine substitutions, salt bridges, hydrophobic interactions, covalent bonds resulting from chemoselective reactions, and combinations thereof. In another embodiment, alterations in conformation are determined according to the ability of the stabilized complexes to (a) retain epitopes bound by broadly neutralizing antibodies (e.g., broadly neutralizing antibodies are selected from the group consisting of VRC01; VRC03; VRC-PG04; b12; b13; F105; 2G12; PG9; PG16; PGT121-123; PGT 125, 128; PGT 126, 127; PGT 130, 131; 4E10; Z13; and 2F5), (b) resist antibody neutralization by CD4, (c) form inter-residue interactions predicted for the mutated residues, (d) bind CD4, CCR5, or CXCR4 ligands, (e) reduce complex lability, (f) prevent dissociation of complex protomers and/or (g) resist cold inactivation. In still another embodiment, the one or more subunits of the complex comprise one or more conservative amino acid substitutions. In yet another embodiment, the complex is glycosylated. In another embodiment, the complex comprises the canonical glycosylation sites present in the wild-type gp120 subunits and wild-type gp41 subunits. In still another embodiment, the gp120 subunit and gp41 subunits of one or more protomeric units are proteolytically cleaved from the same polypeptide. In yet another embodiment, the gp120 subunit and gp41 subunit of one or more protomeric units are not truncated relative to the wild-type subunits. In another embodiment, the trimeric complex is immobilized on an object selected from the group consisting of a cell, a metal, a resin, a polymer, a ceramic, a glass, a microelectrode, a graphitic particle, a bead, a gel, a plate, an array, and a capillary tube. In still another embodiment, the PIV is simian immunodeficiency virus (SIV), human immunodeficiency virus type 1 (HIV-1), or human immunodeficiency virus type 2 (HIV-2).

In another aspect, an isolated polypeptide is provided comprising the amino acid sequence of gp120 and gp41 subunits of a PIV envelope polypeptide, wherein (a) one or more subunits comprises one or more mutated amino acid residues that increases the stability of envelope polypeptide trimer complexes comprising the polypeptide and (b) the one or more mutated amino acid residues does not substantially alter the conformation of the native envelope polypeptide trimer complex, in which the mutated amino acid residues are not altered. In one embodiment, the native envelope polypeptide trimer complex in which the mutated amino acid residues are not altered is in the conformation shown in any one of FIGS. 1-17. In another embodiment, the one or more mutated residues comprises one or more pairs of residues that physically interact within the native complex. In still another embodiment, the positions of the mutated residues are selected from the group consisting of residues listed in Tables 6-9 and combinations thereof. In yet another embodiment, the residue mutations are selected from the group consisting of cysteine-cysteine substitutions, salt bridges, hydrophobic interactions, covalent bonds resulting from chemoselective reactions, and combinations thereof. In another embodiment, the polypeptide contains one or more conservative amino acid substitutions. In still another embodiment, the polypeptide is glycosylated. In yet another embodiment, the polypeptide comprises the canonical glycosylation sites present in the wild-type gp120 subunits and wild-type gp41 subunits. In another embodiment, the gp120 subunit and gp41 subunit of one or more protomeric units are proteolytically cleaved from the same polypeptide. In still another embodiment, the gp120 subunit and gp41 subunit of one or more protomeric units are not truncated relative to the wild-type subunits. In yet another embodiment, the polypeptide is immobilized on an object selected from the group consisting of a cell, a metal, a resin, a polymer, a ceramic, a glass, a microelectrode, a graphitic particle, a bead, a gel, a plate, an array, and a capillary tube. In another embodiment, the polypeptide forms a trimeric complex. In still another embodiment, the PIV is SIV, HIV-1, or HIV-2.

In still another aspect, an isolated nucleic acid which encodes polypeptides described herein is provided. In one embodiment, the nucleic acid comprises a nucleotide sequence set forth in Table 4, and further having one or more mutated residues selected from the group of residues listed in Tables 6-9 and combinations thereof; or a degenerate variant thereof. In another embodiment, the nucleic acid is operably linked to a promoter. In yet another aspect, a vector comprising a nucleic acid described herein is provided. In one embodiment, the vector is an expression vector. In another aspect, a host cell which comprises a vector described herein is provided. In one embodiment, the host cell is a mammalian cell having the ability to glycosylate proteins. In still another aspect, a method of producing a polypeptide comprising culturing a host cell in an appropriate culture medium to thereby produce the polypeptide is provided. In one embodiment, the host cell is a mammalian cell having the ability to glycosylate proteins.

In yet another aspect, an isolated broadly neutralizing antibody or antigen-binding portion thereof is provided that specifically binds to a trimeric complex or polypeptide described herein. In one embodiment, the antibody or antigen-binding portion thereof is a monoclonal antibody, polyclonal antibody, chimeric antibody, humanized antibody, single-chain antibody, antibody fragment, or is detectably labeled.

In another aspect, an immunogenic composition is provided comprising a trimeric complex or polypeptide described herein, and a pharmaceutically acceptable carrier. In one embodiment, the immunogenic composition further comprises an adjuvant. In another embodiment, the adjuvant is selected from the group consisting of alum, Freund's incomplete adjuvant, saponin, Quil A, QS-21, Ribi Detox, monophosphoryl lipid A, a CpG oligonucleotide, CRL-1005, L-121, and any combination thereof. In still another embodiment, the immunogenic composition is capable of eliciting primate immunodeficiency virus-specific neutralizing antibodies in mammals. In yet another embodiment, the PIV is SIV, HIV-1, or HIV-2.

In still another aspect, a method of generating stabilized PIV envelope polypeptide trimer complexes is provided, comprising (a) recombinantly modifying a nucleic acid encoding a PIV envelope polypeptide to encode one or more mutated residues selected from the group consisting of mutated residues listed in Tables 6-9 and combinations thereof, wherein the one or more mutated amino acid residues does not substantially alter the conformation of the native envelope polypeptide trimer complex, in which the mutated amino acid residues are not altered; (b) expressing the recombinant nucleic acid to produce PIV envelope polypeptides that form trimers. In one embodiment, the conformation of the native complex when the mutated amino acid residues are not mutated is the conformation shown in any one of FIGS. 1-17. In another embodiment, the one or more mutated residues comprises one or more pairs of residues that physically interact within the native complex. In still another embodiment, the positions of the mutated residues are selected from the group of residues listed in Tables 6-9 and combinations thereof. In yet another embodiment, the residue mutations are selected from the group consisting of cysteine-cysteine substitutions, salt bridges, hydrophobic interactions, covalent bonds resulting from chemoselective reactions, and combinations thereof. In another embodiment, alterations in conformation are determined according to the stabilized complexes ability to (a) retain epitopes bound by broadly neutralizing antibodies (e.g., broadly neutralizing antibodies are selected from the group consisting of VRC01; VRC03; VRC-PG04; b12; b13; F105; 2G12; PG9; PG16; PGT121-123; PGT 125, 128; PGT 126, 127; PGT 130, 131; 4E10; Z13; and 2F5), (b) resist antibody neutralization by CD4, (c) form inter-residue interactions predicted for the mutated residues, (d) bind ligands CD4 and CCR5, (e) reduce complex lability, (f) prevent dissociation of complex protomers and/or (g) resist cold incubation. In still another embodiment, the one or more conservative amino acid substitutions are made to the PIV envelope polypeptide. In yet another embodiment, the complex is glycosylated. In another embodiment, the complex comprises the canonical glycosylation sites present in the wild-type gp120 subunits and wild-type gp41 subunits. In still another embodiment, the gp120 subunit and gp41 subunit of one or more protomeric units are proteolytically cleaved from the same polypeptide. In yet another embodiment, the gp120 subunit and gp41 subunit of one or more protomeric units are not truncated relative to the wild-type subunits. In another embodiment, the trimeric complex is further immobilized on an object selected from the group consisting of a cell, a metal, a resin, a polymer, a ceramic, a glass, a microelectrode, a graphitic particle, a bead, a gel, a plate, an array, and a capillary tube. In still another embodiment, the PIV is SIV, HIV-1, or HIV-2.

In yet another embodiment, a method of identifying broadly neutralizing anti-primate immunodeficiency virus antibodies is provided, comprising (a) administering an effective amount of an agent selected from the group consisting of a trimeric complex, polypeptide, nucleic acid, vector, host cell, and immunogenic composition described herein, to a subject to generate antibodies that neutralize primate immunodeficiency viruses heterologous to the virus strain or subtype from which the immunogen was derived and (b) isolating antibodies specific for the administered complex or composition.

In another embodiment, a method of identifying broadly neutralizing anti-primate immunodeficiency virus antibodies is provided, comprising (a) administering an effective amount of an agent selected from the group consisting of a trimeric complex, polypeptide, nucleic acid, vector, host cell, and immunogenic composition described herein, to B cells in an in vitro cell culture system to generate antibodies that neutralize the primate immunodeficiency viruses heterologous to the virus strain or subtype from which the immunogen was derived and (b) isolating antibodies specific for the administered complex or composition.

In still another embodiment, a method of making an isolated hybridoma which produces a broadly neutralizing antibody that specifically binds to a trimeric complex or polypeptide is provided, the method comprising: a) immunizing a mammal with an effective amount of an agent selected from the group consisting a trimeric complex, polypeptide, nucleic acid, vector, host cell, and immunogenic composition described herein; b) isolating splenocytes from the immunized mammal; c) fusing the isolated splenocytes with an immortalized cell line to form hybridomas; and d) screening individual hybridomas for production of an antibody which specifically binds with said trimeric complex or polypeptide thereof to isolate the hybridoma. In yet another aspect, an antibody produced by methods described herein are provided.

In another aspect, a method of eliciting an immune response in a subject against a primate immunodeficiency virus is provided, comprising administering to the subject a prophylactically or therapeutically effective amount of an agent selected from the group consisting of a trimeric complex, polypeptide, nucleic acid, vector, host cell, immunogenic composition, and antibody described herein, to thereby elicit the immune response. In one embodiment, the agent is administered in a single dose. In another embodiment, the agent is administered in multiple doses. In still another embodiment, the agent is administered as part of a heterologous prime-boost regimen. In yet another embodiment, the immune response comprises eliciting PIV-specific neutralizing antibodies in mammals. In another embodiment, the PIV is SIV, HIV-1, or HIV-2.

In still another aspect, a method of preventing a subject from becoming infected with a primate immunodeficiency virus is provided, comprising administering to the subject a prophylactically effective amount of an agent selected from the group consisting of a trimeric complex, polypeptide, nucleic acid, vector, host cell, immunogenic composition, and antibody described herein, thereby preventing the subject from becoming infected with the primate immunodeficiency virus. In one embodiment, the subject is exposed to the PIV. In another embodiment, administration of the agent elicits PIV-specific neutralizing antibodies in mammals. In still another embodiment, the PIV is SIV, HIV-1, or HIV-2.

In yet another aspect, a method for reducing the likelihood of a subject's becoming infected with a primate immunodeficiency virus is provided, comprising administering to the subject a prophylactically effective amount of an agent selected from the group consisting of a trimeric complex, polypeptide, nucleic acid, vector, host cell, immunogenic composition, and antibody described herein, thereby reducing the likelihood of the subject's becoming infected with the primate immunodeficiency virus. In one embodiment, the subject is exposed to the PIV. In another embodiment, administration of the agent elicits PIV-specific neutralizing antibodies in mammals. In still another embodiment, the PIV is SIV, HIV-1, or HIV-2.

In another aspect, a method for preventing or delaying the onset of, or slowing the rate of progression of, a primate immunodeficiency virus-related disease in a subject infected with a primate immunodeficiency virus is provided, comprising administering to the subject a therapeutically effective amount of an agent selected from the group consisting of a trimeric complex, polypeptide, nucleic acid, vector, host cell, immunogenic composition, and antibody described herein, thereby preventing or delaying the onset of, or slowing the rate of progression of, the primate immunodeficiency virus-related disease in the subject. In one embodiment, administration of the agent elicits PIV-specific neutralizing antibodies in mammals. In another embodiment, the PIV is SIV, HIV-1, or HIV-2.

BRIEF DESCRIPTION OF THE TABLES

Figure 1:
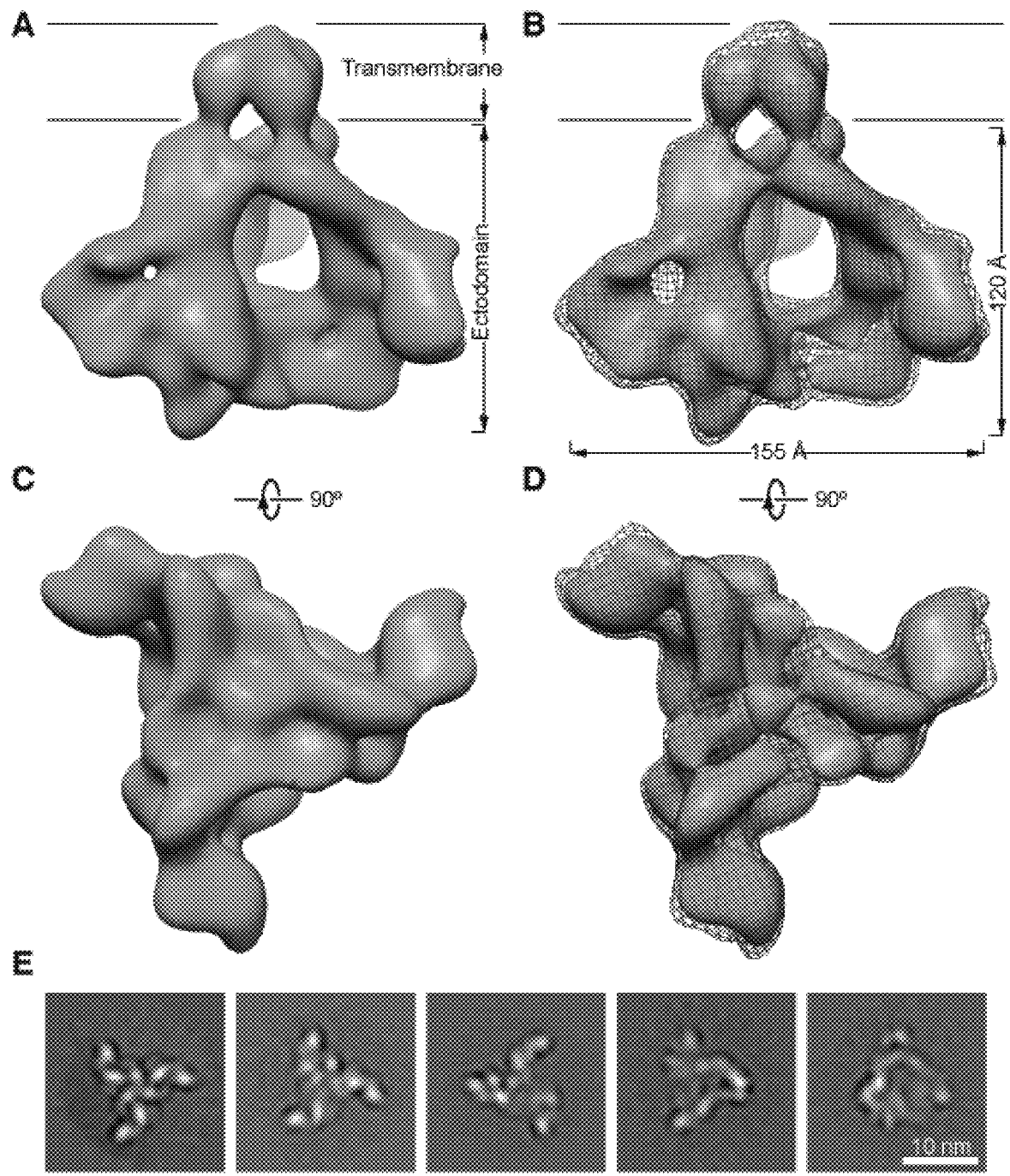
FIGS. 1A-1E show the cryo-EM structure of the membrane-bound HIV-1 Env trimer at ~11-Å resolution. (A) The reconstruction of the HIV-1$_{JR-FL}$ Env(–)$\Delta$CT trimer is shown as a solid surface viewed from a perspective parallel to the viral membrane. The approximate boundaries of the transmembrane region and ectodomain are indicated. (B) The Env trimer reconstruction is visualized at two different levels of contour. The lower and higher levels of contour are illustrated as a meshwork and a solid surface representation, respectively. (C) The Env trimer reconstruction in a solid surface representation is viewed from the perspective of the target cell, at the same contour level as that shown in A. (D) The Env trimer reconstruction is shown at two different levels of contour in the same way as in B, viewed from the perspective of the target cell. (E) The images show typical reference-free class averages produced by maximum-likelihood alignment with no C3 symmetry imposed. Scale bar, 10 nm.

Table 1 shows a list of interactions related to gp120-gp120 association and gp120 TAD stability.

Table 2 shows a list of interactions at the gp41-gp41 interface.

Table 3 shows a list of interactions at the gp120-gp41 interface.

Table 4 shows a list of representative Env nucleic acid and amino acid sequences from numerous primate immunodeficiency viruses.

Table 5 shows a list of interprotomer and intersubunit contacts within the HIV-1 Env trimer.

Table 6 shows a list of interprotomer bonds useful for increasing the stability of Env trimers.

Table 7 shows a list of intersubunit residue pairs useful for increasing the stability of Env trimers, especially using disulfide bonds.

Table 8 shows a list of intrasubunit residue pairs useful for increasing the stability of Env trimers, especially using disulfide bonds or promoting hydrophobic interactions.

Table 9 shows a list of residues useful for increasing the stability of Env trimers by increasing the solubility of the trimers.

DETAILED DESCRIPTION OF THE INVENTION

The present invention is based in part on the elucidation of the structure of the fully glycosylated HIV-1 envelope trimer in its unliganded, pre-fusion state, including the complete ectodomain, the transmembrane region, and all of the peptide-proximal asparagine-linked glycans, by cryo-electron microscopy (cryo-EM). The structure reveals a dramatic conformational transition of gp120 between its unliganded and CD4-bound states, a torus-like fold of gp41 entirely different from its post-fusion conformation, and a conserved topology of the glycan shield. The structure of the trimer exhibits a spring-loaded mechanism that stores the free energy fueling virus entry. The structure further provides insights into virus-host interactions, mechanisms by which primate immunodeficiency viruses evade immune responses, and represents an atomic reference for inhibitor and vaccine design. Specifically, one or more amino acid residue changes, whose positions are numbered herein according to the envelope protein of the HIV-1 HXBc2 reference isolate and equivalent positions identified within envelope proteins from different PIV species, strains, or isolates, can be engineered to enhance the stability of PIV envelope glycoprotein trimers.

Some embodiments of the present invention are directed to envelope complexes in an immunogenic or antigenic conformation sufficient to elicit broadly neutralizing responses (e.g., production of broadly neutralizing antibodies). According to one aspect of the present invention, the sequences described and/or claimed herein can be altered or designed to maintain the same or a substantially similar amino acid sequence or protein in an immunogenic or antigenic conformation. In addition, the amino acid sequences or proteins of the present invention can be altered or modified according to methods known in the art to have different sequences yet still be capable of being placed in an immunogenic or antigenic conformation and/or having increased conformationally stability. It is to be understood that the specific amino acid sequences and proteins described herein include sequences and proteins that are substantially similar or homologous thereto or those that can be modified in a manner contemplated by those skilled in the art without departing from the spirit and operation of the present invention.

In order that the present invention can be more readily understood, certain terms are first defined. Additional definitions are set forth throughout the detailed description.

The term "adjuvants" refers to any agent suitable for enhancing the immunogenicity of an antigen, such as protein and nucleic acid. Adjuvants suitable for use with protein-based immunogens are well known in the art and include, but are not limited to, alum, Freund's incomplete adjuvant (FIA), Saponin, Quil A, QS21, Ribi Detox, Monophosphoryl lipid A (MPL), and nonionic block copolymers such as L-121 (Pluronic; Syntex SAF). Methods of combining adjuvants with antigens are well known to those skilled in the art. Adjuvants can also be in particulate form. The antigen can be incorporated into biodegradable particles composed of poly-lactide-co-glycolide (PLG) or similar polymeric material. Such biodegradable particles are known to provide sustained release of the immunogen and thereby stimulate long-lasting immune responses to the immunogen. Other particulate adjuvants, include but are not limited to, micellular mixtures of Quil A and cholesterol known as immunostimulating complexes (ISCOMs) and aluminum or iron oxide beads. It is also known to those skilled in the art that cytotoxic T lymphocyte and other cellular immune responses are elicited when protein-based immunogens are formulated and administered with appropriate adjuvants, such as ISCOMs and micron-sized polymeric or metal oxide particles. Suitable adjuvants for nucleic acid-based vaccines include, but are not limited to, Quil A, interleukin-12 delivered in purified protein or nucleic acid form, short bacterial immunostimulatory nucleotide sequence, such as CpG-containing motifs, interleukin-2/Ig fusion proteins delivered in purified protein or nucleic acid form, oil in water microemulsions such as MF59, polymeric microparticles, cationic liposomes, monophosphoryl lipid A (MPL), immunomodulators such as Ubenimex, and genetically detoxified toxins such as *E. coli* heat labile toxin and cholera toxin from *Vibrio*. *Such adjuvants and methods of combining adjuvants with antigens are well known to those skilled in the art. In addition, methods for combining antigens and particulate adjuvants are well known to those skilled in the art.*

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

Unless otherwise specified herein, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives can comprise a protein or chemical moiety conjugated to an antibody. The term "antibody" as used herein also includes an "antigen-binding portion" of an antibody (or simply "antibody portion"). The term "antigen-binding portion," as used herein, refers to one or more fragments of an antibody that retain the ability to specifically bind to an antigen (e.g., envelope glycoprotein trimer complexes or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242: 423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Still further, an antibody or antigen-binding portion thereof can be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein. Antibodies can be polyclonal or monoclonal; xenogeneic, allogeneic, or syngeneic; or modified forms thereof (e.g., humanized, chimeric, etc.). Antibodies can also be fully human. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "antigen-presenting cells" include, but are not limited to, dendritic cells, Langerhan cell, monocytes, macrophages, muscle cells and the like. In some embodiments, antigen presenting cells present an antigen, or an immunogenic part thereof, such as a peptide, or derivative and/or analogue thereof, in the context of major histocompatibility complex I or complex II, to other cells.

The term "binding" or "interacting" refers to an association, which can be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" is intended to include tissues, cells and biological fluids isolated from a subject, as well as tissues, cells and fluids present within a subject.

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, and vomit). In some embodiments, media described herein can contain or comprise body fluids.

The term "broadly neutralizing" is well known in the art and refers to the ability of one or more agents (e.g., antibodies, aptamers, protein-binding nucleic acids, small molecules, etc.) to react with an infectious agent to destroy or greatly reduce the virulence of the infectious agent. The presence of such a response has the potential to prevent the establishment of infection and/or to significantly reduce the number of cells that become infected with a PIV, potentially delaying viral spread and allowing for a better control of viral replication in the infected host. A broadly neutralizing antibody against a PIV will typically bind a variety of different clades, groups or mutants of PIV. In some embodiments, the broadly neutralizing anti-PIV agent is an antibody that specifically binds to and neutralizes two, three, four, five, six, seven, eight, nine, ten or more clades and/or two or more groups of PIV (e.g., within HIV-1 or HIV-2).

The term "canonical glycosylation site" includes, but is not limited to, an Asn-X-Ser or Asn-X-Thr sequence of amino acids that defines a site for N-linkage of a carbohydrate. In addition, Ser or Thr residues not present in such sequences to which a carbohydrate can be linked through an O-linkage are canonical glycosylation sites. In the latter case of a canonical glycosylation site, a mutation of the Ser and Thr residue to an amino acid other than a serine or threonine will remove the site of O-linked glycosylation.

The term "CCR5" or "C—C chemokine receptor type 5" refers to a chemokine receptor which binds members of the C—C group of chemokines. At least two transcript variants encoding the same human CCR5 protein exist. The sequence of human CCR5 transcript variant 1, which encodes the longer of the two human CCR5 isoforms (i.e., isoform a), is available to the public at the GenBank database under NM_00579.3 and NP_000570.1. The sequence of human CCR5 transcript variant 2 differs in the 5' untranslated region (UTR) compared to variant 1, while still encoding the same CCR5 protein and the sequences can be found under NM_001100168.1 and NP_001093638.1. Nucleic acid and polypeptide sequences of CCR5 orthologs in organisms other than humans are well known and include, for example, mouse CCR5 (NM_009917.5 and NP_034047.2), chimpanzee CCR5 (NM_001009046.1 and NP_001009046.1), rat CCR5 (NM_043960.3 and NP_446412.2), cow CCR5 (NM_001011672.2 and NP_001011672.2), dog CCR5 (NM_001012342.2 and NP_001012342.2), and chicken CCR5 (NM_001045834.1 and NP_001039299.1). As used herein, CCR5 includes extracellular portions of CCR5 capable of binding PIV envelope proteins.

The term "CD4" refers to a membrane glycoprotein of T lymphocytes that interacts with major histocompatibility complex class II antigens and is also a receptor for PIVs. The sequence of the human CD4 transcript variant 1 is available to the public at the GenBank database under NM_000616.4 and NP_000607.1. Nucleic acid and polypeptide sequences of CD4 orthologs in organisms other than humans are well known and include, for example, mouse CCR5 (NM_013488.2 and NP_038516.1), chimpanzee CD4 (NM_0010099043.1 and NP_001009043.1), rat CD4 (NM_012705.1 and NP_036837.1), cow CD4 (NM_001103225.1 and NP_001096695.1), dog CD4 (NM_001003252.1 and NP_001003252.1), and chicken CD4 (NM_204649.1 and NP_989980.1). As used herein, CD4 includes extracellular portions of CD4 capable of binding PIV envelope proteins. The extracellular domain of CD4 consists of four contiguous immunoglobulin-like regions (D1, D2, D3, and D4, see Sakihama et al., Proc. Natl. Acad. Sci. 92:6444, 1995; U.S. Pat. No. 6,117,655), and amino acids 1 to 183 have been shown to be involved in gp120 binding. For instance, a binding molecule or binding domain derived from CD4 would comprise a sufficient portion of the CD4 protein to mediate specific and functional interaction between the binding fragment and a native or viral binding site of CD4. One such binding fragment includes both the D1 and D2 extracellular domains of CD4 (D1D2 is also a fragment of soluble CD4 or sCD4 which is comprised of D1, D2, D3, and D4), although smaller fragments may also provide specific and functional CD4-like binding. The gp120-binding site has been mapped to D1 of CD4.

The term "chemoselective reaction" refers to reactions that may be used to stabilize peptides or polypeptides. For example, chemoselective ligation reactions that may be used to stabilize such compositions as described herein include, but are not limited to, reactions between amino acids of polypeptides described herein and involving: (i) an aldehyde/ketone and a hydrazide to form a hydrazone; (ii) a ketone and a aminoxy group to form an oxime; (iii) a ketone and a thiosemicarbazide to form a thiosemicarbazone; (iv) an aldehyde and a beta-amino thiol to form a thiazolidine; (v) a thiocarboxylate and a .alpha-halo carbonyl to form a thioester; (vi) a thioester and a N-terminal peptide cysteine to form an amide; (vii) a alkyl halide and a thiol to form a thioether; and, (viii) a maleimide and a thiol to form a thioether.

The term "complex" refers to an association between at least two moieties (e.g. chemical or biochemical) that have an affinity for one another. "Protein complex" or "polypeptide complex" refers to a complex comprising at least one or more polypeptides. In one embodiment, a complex comprises a trimer of protomeric units comprising a gp120 subunit and a gp41 subunit. Embodiments of complexes described herein can encompass other molecules (e.g., polypeptides) that can bind to the complex, such as an antibody.

The term "CXCR4" or "C—X—C chemokine receptor type 4" is a chemokine receptor which binds members of the C—X—C group of chemokines. At least two transcript variants encoding the same human CXCR4 protein exist. The sequence of human CXCR4 transcript variant 1, which encodes the longer of the two human CXCR4 isoforms (i.e., isoform a), is available to the public at the GenBank database under NM_001008540.1 and NP_001008540.1. The sequence of human CXCR4 transcript variant 2 differs in the 5' untranslated region (UTR) and lacks an in-frame portion of the 5' coding region compared to variant 1 and therefore encodes a smaller polypeptide having a shorter N-terminus relative to that of isoform 1. Such nucleic acid and protein sequences can be found under NM_003467.2 and NP_003458.1. Nucleic acid and polypeptide sequences of CXCR4 orthologs in organisms other than humans are well known and include, for example, mouse CXCR4 (NM_009911.3 and NP_034041.2), chimpanzee CXCR4 (NM_001009047.1 and NP_001009047.1), rat CXCR4 (NM_022205.3 and NP_071541.2), cow CXCR4 (NM_174301.3 and NP_776726.1), dog CXCR4 (NM_001048026.1 and NP_001041491.1), and chicken CXCR4 (NM_204617.2 and NP_989948.2). As used herein, CXCR4 includes extracellular portions of CXCR4 capable of binding the PIV envelope protein.

The term "effective amount" refers to an amount sufficient to achieve a desired result. For example, a "prophylactically effective amount" refers to an amount sufficient to reduce the likelihood of a disorder from occurring. In addition, a "therapeutically effective amount" refers to an amount effective to slow, stop or reverse the progression of a disorder.

The term "envelope," "envelope glycoprotein," or "Env" in reference to PIV polypeptides refers to certain polypeptides and/or complexes produced by such viruses. Generally, the env gene encodes gp160, which is proteolytically cleaved into gp120 and gp140. Gp120 binds to the CD4 receptor on a target cell that has such a receptor, such as, e.g., a T-helper cell. Gp41 is non-covalently bound to gp120, and provides the second step by which HIV enters the cell. It is originally buried within the viral envelope, but when gp120 binds to a CD4 receptor, gp120 changes its conformation causing gp41 to become exposed, where it can assist in fusion with the host cell. In some embodiments, the envelope glycoprotein includes a transmembrane gp41 or gp36 (e.g., "gp41/gp36") subunit and an external, noncovalently associated gp120 subunit. The Env complex is expressed as a trimeric structure of three gp120/gp41 pairs ("protomers") that mediates the multistep process of fusion of the virion envelope with the membrane of the target CD4+ T-cell. In some PIVs, the gp41 subunit is truncated to a gp36 subunit. Table 4 shows a list of representative Env nucleic acid and amino acid sequences from numerous primate immunodeficiency viruses.

As used herein, "exposure" to a PIV refers to contact with the PIV such that infection could result.

The term "gp41" or "gp41/gp36" denotes the retroviral transmembrane envelope glycoprotein 41 or glycoprotein 36 that is found in retroviruses, such as PIVs. With respect to PIVs, gp41 or gp36 is a highly immunogenic protein which elicits a strong and sustained antibody response in humans infected with HIV. The structure of gp41 from HIV-1 is described herein and is representative of other gp41 sequences described herein. The term includes, without limitation, (a) whole gp41 including the transmembrane and cytoplasmic domains; (b) gp41 ectodomain (gp41ECTO); (c) gp41 modified by deletion or insertion of one or more glycosylation sites; (d) gp41 modified so as to eliminate or mask the well-known immunodominant epitope; (e) a gp41 fusion protein; and (f) gp41 labeled with an affinity ligand or other detectable marker. As used herein, "ectodomain" means the extracellular region of a transmembrane protein exclusive of the transmembrane spanning and cytoplasmic regions.

The term "gp120" denotes the outer envelope protein found in retroviruses, such as PIVs. The envelope protein is initially synthesized as a longer precursor protein of 845-870 amino acids in size, designated gp160. Gp160 forms a homotrimer and undergoes glycosylation within the Golgi apparatus. It is then cleaved by a cellular protease into gp120 and gp41. Gp41 contains a transmembrane domain and remains in a trimeric configuration and it interacts with gp120 in a non-covalent manner. Gp120 contains most of the external, surface-exposed, domains of the envelope glycoprotein complex, and it is gp120 which binds both to the cellular CD4 receptor and to the cellular chemokine receptors (e.g., CCR5). Fragments similar to those defined for gp41 described herein are also contemplated.

The term "immunizing" refers to generating an immune response to an antigen in a subject. This can be accomplished, for example, by administering a primary dose of an immunogen to a subject, followed after a suitable period of time by one or more subsequent administrations of the immunogen, so as to generate in the subject an immune response against the immunogen. A suitable period of time between administrations of the immunogen can readily be determined by one skilled in the art, and is usually on the order of several weeks to months.

The term "immune response" is intended to include, but is not limited to, T and/or B cell responses, that is, cellular and/or humoral immune responses. The immune response of a subject can be determined by, for example, assaying antibody production, immune cell proliferation, the release of cytokines, the expression of cell surface markers, cytotoxicity, and the like. As used herein, the term "immune cell" is intended to include, but is not limited to, cells that are of hematopoietic origin and play a role in an immune response. Immune cells include, but are not limited to, lymphocytes, such as B cells and T cells; natural killer cells; myeloid cells, such as monocytes, macrophages, eosinophils, mast cells, basophils, and granulocytes.

As used herein, the term "inhibit" includes the decrease, limitation, or blockage, of, for example a particular action, function, or interaction. For example, a PIV-related infection or disease is "inhibited" if at least one symptom of the disease, such as viral load or low T cell count, is alleviated, terminated, slowed, or prevented. As used herein, PIV-related infection or disease is also "inhibited" if recurrence of a disease symptom is reduced, slowed, delayed, or prevented. Such an inhibition can affect a PIV-mediated activity (e.g., infection, fusion (e.g., target cell entry and/or syncytia formation), viral spread and the like) and/or a decrease in viral titer. For example, a PIV-mediated activity can be decreased by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more. The term "promote," in some embodiments, can be used in the exact opposite manner as "inhibit."

The term "isolated polypeptide" refers to a polypeptide that (1) is not associated with proteins that it is normally found within nature, (2) is isolated from the cell in which it normally occurs, (3) is substantially free of other proteins from the same cellular source, (4) is expressed by a cell from a different species, or (5) does not occur in nature. The term "substantially free of cellular material" includes preparations of protein in which the protein is separated from cellular components of the cells in which it is naturally or recombinantly produced. In one embodiment, the language "substantially free of cellular material" includes preparations of envelope protein having less than about 30% (by dry weight) of non-envelope protein (also referred to herein as a "contaminating protein"), more preferably less than about 20% of non-envelope protein, still more preferably less than about 10% of non-envelope protein, and most preferably less than about 5% non-envelope protein. When the protein is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of envelope protein in which the protein is separated from chemical precursors or other chemicals which are involved in the synthesis of the protein. In one embodiment, the language "substantially free of chemical precursors or other chemicals" includes preparations of envelope protein having less than about 30% (by dry weight) of chemical precursors of non-envelope chemicals, more preferably less than about 20% chemical precursors of non-envelope chemicals, still more preferably less than about 10% chemical precursors of non-envelope chemicals, and most preferably less than about 5% chemical precursors of non-envelope chemicals. In preferred embodiments, isolated proteins or biologically active portions thereof lack contaminating proteins from the same animal from which the envelope protein is derived. Typically, such proteins are produced by recombinant expression of, for example, a human envelope protein in a nonhuman cell. Similar considerations apply for "isolated nucleic acids."

The term "not substantially altered," "not substantially modulated," and the like, unless otherwise defined, refers to a minimal deviation of a measured attribute in comparison to a reference control. The deviation can be measured according to quantitative or qualitative means. In one embodiment, the attribute's alteration is less than 30%, 29%, 28%, 27%, 26%, 25%, 24%, 23%, 22%, 21%, 20%, 19%, 18%, 17%, 16%, 15%, 10%, 9%, 8%, 7%, 6%, 5%, 4%, 2%, 1% or less different relative to the control (e.g., inter-residue differences, angles-of-approach, affinity for antibody binding, etc.).

The terms "label" or "labeled" refer to incorporation or attachment, optionally covalently or non-covalently, of a detectable marker into a molecule, such as a polypeptide. Various methods of labeling polypeptides are known in the art and can be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

An "overexpression" or "significantly higher level of expression or copy number" of a marker refers to an expression level or copy number in a test sample that is greater than the standard error of the assay employed to assess expression or copy number, and is preferably at least twice, and more preferably three, four, five or ten or more times the expression level or copy number of the marker in a control sample (e.g., sample from a healthy subject not afflicted with a PIV infection or related disease) and preferably, the average expression level or copy number of the marker in several control samples.

The term "primate immunodeficiency virus" or "PIV" refers to a group of well-known viruses infecting primates. The term includes human immunodeficiency viruses (HIV) and simian immunodeficiency viruses (SIV). For example, the term includes the human viruses, HIV-1 and HIV-2; the chimpanzee virus SIVcpz such as, for example, SIVcpzGab, SIVcpzCam, SIVcpzAnt, and SIVcpzUS; the sooty mangabey virus SIVsm; the African green monkey virus SIVagm such as, for example, SIVagm-1 and SIVagm-2; the mandrill virus SIVmnd such as, for example, SIVmnd14 and SIV mndGB 1, as well as a host of others including SIVsun/lhoest, SIVcol, SIVrcm, SIVsyk, SIVdeb, SIVgsn, SIVmon, SIVmus, and SIVtal. PIV is inclusive of all strains (e.g., SIVcpz) and sub-strains (e.g., SIVcpzGab). Regarding human immunodeficiency viruses, HIVs can be categorized into multiple clades with a high degree of genetic divergence. As used herein, the term "clade" refers to related human immunodeficiency viruses classified according to their degree of genetic similarity. There are currently three groups of HIV-1 isolates: M, N, and O. Group M (major strains) consists of at least ten clades, A through J. Group O (outer strains) can consist of a similar number of clades. Group N is a new HIV-1 isolate that has not been categorized in either group M or O.

The term "reducing the likelihood of a subject's becoming infected with a virus" refers to reducing the likelihood of the subject's becoming infected with the virus by at least two-fold. For example, if a subject has a 1% chance of becoming infected with the virus, a two-fold reduction in the likelihood of the subject becoming infected with the virus would result in the subject having a 0.5% chance of becoming infected with the virus. In one embodiment, reducing the likelihood of the subject's becoming infected with the virus means reducing the likelihood of the subject's becoming infected with the virus by at least 2-, 3-, 4-, 5-, 6-, 7-, 8-, 9-, 10-fold, or more.

The term "response to therapy" relates to any response of the PIV-related infection or disease to a therapy. Responses can be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of PIV-related infection or disease response can be done early after the onset of therapy, e.g., after a few hours, days, weeks or preferably after a few months. Additional criteria for evaluating the response to therapies are related to "survival," which includes all of the following: survival until mortality, also known as overall survival (wherein said mortality can be either irrespective of cause or tumor related); "recurrence-free survival" (e.g., viral load below a detectable threshold); metastasis free survival; disease free survival. The length of said survival can be calculated by reference to a defined start point (e.g., time of diagnosis or start of treatment) and end point (e.g., death, recurrence or metastasis). In addition, criteria for efficacy of treatment can be expanded to include response to therapy, probability of survival, probability of disease manifestation recurrence within a given time period. For example, in order to determine appropriate threshold values, a particular therapeutic regimen can be administered to a population of subjects and the outcome can be correlated to viral load or other measurements that were determined prior to administration of any therapy. Alternatively, outcome measures, such as overall survival and disease-free survival can be monitored over a period of time for subjects following therapy for whom measurement values are known.

The term "stabilizing" or "enhancing stability" of an entity, such as a polypeptide or protein complex, means to make the entity more long-lived or resistant to dissociation. Enhancing stability can be achieved, for example, by enhancing covalent interactions, by enhancing non-covalent interactions, and/or reducing steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds (e.g., disulfide bonds and chemoselective reactions). Non-covalent interactions include, but are not limited to ionic bonds (e.g., salt bridges), hydrogen bonds, hydrophobic interactions, van der Waals interactions, and weak chemical bonds (via short-range noncovalent interactions). A review of noncovalent interactions can be found in Alberts et al., in Molecular Biology of the Cell, 3rd Ed., Garland Publishing, 1994. Steric interactions are generally understood to include those where the structure of the compound is such that it is capable of occupying a site by virtue of its three dimensional structure, as opposed to any attractive forces between the compound and the site. Stabilizing interactions can include one or more of the interactions described herein, or any combination thereof. Stability-enhancing changes can be introduced by recombinant methods. As used herein, "mutant" means that which is not wild type, compared to a reference control.

The term "subject" refers to any healthy animal, mammal or human, or any animal, mammal or human afflicted with a PIV-related infection or disease.

The term "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following: survival until mortality, also known as overall survival (wherein said mortality can be either irrespective of cause or tumor related); "recurrence-free survival" (wherein the term recurrence shall include both localized and distant recurrence); disease free survival (wherein the term disease shall include antiviral infection and diseases associated therewith). The length of said survival can be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of disease recurrence.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

An "underexpression" or "significantly lower level of expression or copy number" of a marker refers to an expression level or copy number in a test sample that is greater than the standard error of the assay employed to assess expression or copy number, but is preferably at least twice, and more preferably three, four, five or ten or more times less than the expression level or copy number of the marker in a control sample (e.g., sample from a healthy subject not afflicted with PIV-related infection or disease) and preferably, the average expression level or copy number of the marker in several control samples.

The term "virally infected" refers to the introduction of viral genetic information into a target cell, such as by fusion of the target cell membrane with the virus or infected cell. The target can be a cell of a subject. In some embodiments, the target cell is a cell in a human subject.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet can be employed (illustrated above). Therefore, a number of different nucleotide sequences can code for a given amino acid sequence. Such nucleotide sequences are considered functionally equivalent since they result in the production of the same amino acid sequence in all organisms (although certain organisms can translate some sequences more efficiently than they do others). Moreover, occasionally, a methylated variant of a purine or pyrimidine can be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence.

Similarly, description and/or disclosure of a fusion protein or polypeptide amino acid sequence herein should be considered to also include description and/or disclosure of all possible nucleotide sequences that can encode the amino acid sequence.

Before the present invention is further described, it will be appreciated that specific sequence identifiers (SEQ ID NOs) have been referenced throughout the specification for purposes of illustration and should therefore not be construed to be limiting. Any marker of the invention, including, but not limited to, the markers described in the specification and markers described herein are well known in the art and can be used in the embodiments of the invention.

It is further to be understood that this invention is not limited to particular embodiments described, as such can, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an envelope glycoprotein trimer complex" includes a plurality of such complexes and reference to "the active agent" includes reference to one or more active agents and equivalents thereof known to those skilled in the art, and so forth. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which can need to be independently confirmed.

I. Isolated Nucleic Acids

One aspect of the invention pertains to isolated nucleic acid molecules that encode PIV envelope polypeptides having the ability to enhance the stability of envelop glycoprotein trimers in an immunologic conformation that enhances broadly neutralizing anti-PIV responses. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated envelope nucleic acid molecule can contain less than about 5 kb, 4 kb, 3 kb, 2 kb, 1 kb, 0.5 kb or 0.1 kb of nucleotide sequences which naturally flank the nucleic acid molecule in viral DNA. Moreover, an "isolated" nucleic acid molecule, such as a cDNA molecule, can be substantially free of other cellular material, or culture medium when produced by recombinant techniques, or chemical precursors or other chemicals when chemically synthesized.

A PIV envelope nucleic acid molecule of the present invention, e.g., a nucleic acid molecule having the nucleotide sequence of an envelope polypeptide-encoding nucleic acid sequence shown in Table 4 that further encodes one or more mutated residues listed in Tables 6-9, or a nucleotide sequence which is at least about 50%, preferably at least about 60%, more preferably at least about 70%, yet more preferably at least about 80%, still more preferably at least about 90%, and most preferably at least about 95%, 96%, 97%, 98%, 99% or more identical to such nucleotide sequences, can be engineered and isolated using standard molecular biology techniques and the sequence information provided herein (i.e., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989). Moreover, such nucleic acids can be isolated by the polymerase chain reaction using oligonucleotide primers designed based upon envelope sequences (e.g., the sequence of an envelope polypeptide-encoding nucleic acid sequence shown in Table 4 that further encodes one or more mutated residues listed in Tables 6-9, or fragment thereof, or the homologous nucleotide sequence). For example, RNA or DNA can be isolated from PIV nucleic acid (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed. A nucleic acid of the present invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an envelope nucleotide sequence of the present invention can be prepared by standard synthetic techniques, i.e., using an automated DNA synthesizer.

Probes based on the envelope nucleotide sequences of the present invention can be used to detect homologs in related PIVs. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express an envelope protein, such as by measuring a level of an envelope-encoding nucleic acid in a sample of cells from a subject, i.e., detecting envelope RNA levels.

Nucleic acid molecules encoding other envelope members and thus which have a nucleotide sequence which differs from the envelope sequences of an envelope polypeptide-encoding nucleic acid sequence shown in Table 4 that further encodes one or more mutated residues listed in Tables 6-9, or fragment thereof, are contemplated. In one embodiment, the nucleic acid molecule(s) of the invention encodes a protein or portion thereof which includes an amino acid sequence which is sufficiently homologous to an envelope polypeptide amino acid sequence shown in Table 4 that further encodes one or more mutated residues listed in Tables 6-9, or fragment thereof, such that the protein or portion thereof forms a stable trimer complex that maintains or enhances one or more of the following biological activities: a) the conformation of the native trimer complex in the absence of the one or more mutated residues; b) the conformation of a trimer complex shown in any one of FIGS. 1-17; c) epitopes bound by broadly neutralizing antibodies, (b) resistance to antibody neutralization by CD4, (c) amino acid inter-residue interactions predicted for the mutated residues, (d) complex binding to ligands CD4, CCR5 or CXCR4, (e) reduction in complex lability, (f) prevention of dissociation of complex protomers and/or (g) resistance to cold inactivation.

In another embodiment, the nucleic acid encodes an envelope protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of an envelope polypeptide amino acid sequence shown in Table 4 that further encodes one or more mutated residues listed in Tables 6-9, or a fragment thereof.

The invention further encompasses envelope nucleic acid molecules that differ from the nucleotide sequences shown in an envelope polypeptide-encoding nucleic acid sequence shown in Table 4 that further encode one or more mutated residues listed in Tables 6-9. In another embodiment, an isolated nucleic acid molecule of the invention has a nucleotide sequence encoding a protein having an envelope polypeptide amino acid sequence shown in Table 4 that further has one or more mutated residues listed in Tables 6-9, or fragment thereof, or a protein having an amino acid sequence which is at least about 70%, 75%, 80%, 85%, 90%, 91%, 92%, 93%, 94%, 95%, 96%, 97%, 98%, 99% or more homologous to an envelope polypeptide amino acid sequence shown in Table 4 that further has one or more mutated residues listed in Tables 6-9, or fragment thereof.

It will be appreciated by those skilled in the art that DNA sequence polymorphisms that lead to changes in the amino acid sequences of envelope can exist within a population (e.g., a mammalian and/or human population). Such genetic polymorphism in the envelope gene can exist among individuals within a population due to natural allelic variation. As used herein, the terms "gene" and "recombinant gene" refer to nucleic acid molecules comprising an open reading frame encoding an envelope protein, preferably a mammalian, e.g., human, envelope protein. Such natural allelic variations can typically result in 1-5% variance in the nucleotide sequence of the envelope gene. Any and all such nucleotide variations and resulting amino acid polymorphisms in envelope that are the result of natural allelic variation and that do not alter the functional activity of envelope are intended to be within the scope of the invention. Nucleic acid molecules corresponding to natural allelic variants and homologues within PV strains, clades, species, etc. can be isolated.

In addition to naturally-occurring allelic variants of the envelope sequence that can exist in the population, the skilled artisan will further appreciate that changes can be introduced by mutation into the nucleotide sequence of an envelope polypeptide-encoding nucleic acid sequence shown in Table 4 that further encodes one or more mutated residues listed in Tables 6-9, or fragment thereof, thereby leading to changes in the amino acid sequence of the encoded envelope protein, without altering the functional ability of the envelope protein. For example, nucleotide substitutions leading to amino acid substitutions at "non-essential" amino acid residues can be made in the sequences. A "non-essential" amino acid residue is a residue that can be altered from the wild-type sequence of an envelope polypeptide (e.g., an envelope polypeptide amino acid sequence shown in Table 4, or fragment thereof) without substantially altering the immunogenic conformation of envelope trimers, whereas an "essential" amino acid residue is affects the immunogenic conformation of the envelope trimer. Other amino acid residues, however, (e.g., those that are not conserved or only semi-conserved between mouse and human) cannot be essential for activity and thus are likely to be amenable to alteration without altering envelope activity.

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (J. Mol. Biol. (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding an envelope protein homologous to an envelope polypeptide amino acid sequence shown in Table 4 that further has one or more mutated residues listed in Tables 6-9, or fragment thereof, can be created by introducing one or more nucleotide substitutions, additions or deletions into the nucleotide sequence of an envelope polypeptide-encoding nucleic acid sequence shown in Table 4, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in envelope is preferably replaced with another amino acid residue from the same side chain family. Alternatively, in another embodiment, mutations can be introduced randomly along all or part of an envelope coding sequence, such as by saturation mutagenesis, and the resultant mutants can be screened for an envelope activity described herein to identify mutants that retain envelope activity. Following mutagenesis, the encoded protein can be expressed recombinantly (as described herein) and the activity of the protein can be determined using, for example, assays described herein.

Envelope protein levels can be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In some embodiments, PIV envelope expression levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In other embodiments, the envelope mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays.

As an alternative to making determinations based on the absolute envelope expression level, determinations can be based on the normalized envelope expression level. Expression levels are normalized by correcting the absolute envelope expression level by comparing its expression to the expression of a non-envelope gene, e.g., a housekeeping or other reference gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of an envelope protein can also be detected and/or quantified by detecting or quantifying the expressed polypeptide. The envelope polypeptide can be detected and quantified by any of a number of means well known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express envelope.

II. Recombinant Expression Vectors and Host Cells

Another aspect of the invention pertains to the use of vectors, preferably expression vectors, containing a nucleic acid encoding envelope (or a portion or complex thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising an envelope nucleic acid molecule are used.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of envelope in prokaryotic or eukaryotic cells. For example, envelope can be expressed in bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence is cloned into a pGEX expression vector to create a vector encoding a fusion protein comprising, from the N-terminus to the C-terminus, and/or GST-thrombin cleavage site. The fusion protein can be purified by affinity chromatography using glutathione-agarose resin. Recombinant envelope unfused to GST can be recovered by cleavage of the fusion protein with thrombin.

Examples of suitable inducible non-fusion E. coli expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the envelope expression vector is a yeast expression vector. Examples of vectors for expression in yeast S. cerivisae include pYepSec1 (Baldari, et al., (1987) EMBO J. 6:229-234), pMFa (Kurjan and Herskowitz, (1982) Cell 30:933-943), pJRY88 (Schultz et al., (1987) Gene 54:113-123), and pYES2 (Invitrogen Corporation, San Diego, Calif.).

Alternatively, envelope can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the α-fetoprotein promoter (Campes and Tilghman (1989) Genes Dev. 3:537-546).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications can occur in succeeding generations due to either mutation or environmental influences, such progeny cannot, in fact, be identical to the parent cell, but are still included within the scope of the term as used herein.

A host cell can be any prokaryotic or eukaryotic cell. For example, envelope protein can be expressed in bacterial cells such as E. coli, insect cells, yeast or mammalian cells (such as Fao hepatoma cells, primary hepatocytes, Chinese hamster ovary cells (CHO) or COS cells). Other suitable host cells are known to those skilled in the art. In some embodiments, the host cell choice is determined according to the desire for glycosylation and, if so, the desired pattern of glycosylation. For example, trimers or polypeptides of the present invention can be produced using mammalian cell lines to produce polypeptides having mammalian patterns of glycosylation. Mammalian cell lines include, for example, monkey kidney CV1 line transformed by SV40 (COS-7); human embryonic kidney line 293; baby hamster kidney cells (BHK); Chinese hamster ovary-cells-DHFR$^+$ (CHO); Chinese hamster ovary-cells DHFR-(DXB11); monkey kidney cells (CV1); African green monkey kidney cells (VERO-76); human cervical carcinoma cells (HELA); canine kidney cells (MDCK); human lung cells (W138); human liver cells (Hep G2); mouse mammary tumor (MMT 060562); mouse cell line (C127); and myeloma cell lines.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

A cell culture includes host cells, media and other byproducts. Suitable media for cell culture are well known in the art. An envelope polypeptide or fragment thereof, can be secreted and isolated from a mixture of cells and medium containing the polypeptide.

Alternatively, an envelope polypeptide or fragment thereof, can be retained cytoplasmically and the cells harvested, lysed and the protein or protein complex isolated. An envelope polypeptide or fragment thereof, can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of envelope or a fragment thereof. In other embodiments, heterologous tags can be used for purification purposes (e.g., epitope tags and FC fusion tags), according to standards methods known in the art.

Thus, a nucleotide sequence encoding all or a selected portion of an envelope polypeptide can be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, can be employed to prepare recombinant envelope polypeptides, or fragments thereof, by microbial means or tissue-culture technology in accord with the subject invention.

In another variation, protein production can be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system can be used. Such systems typically comprise at least an RNA polymerase holoenzyme, ribonucleotides and any necessary transcription initiation, elongation and termination factors. In vitro transcription and translation can be coupled in a one-pot reaction to produce proteins from one or more isolated DNAs.

In certain embodiments, the envelope polypeptide, or fragment thereof, can be synthesized chemically, ribosomally in a cell free system, or ribosomally within a cell. Chemical synthesis can be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full-length ligation products are chemically identical to proteins produced by cell free synthesis. Full length ligation products can be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

For stable transfection of mammalian cells, it is known that, depending upon the expression vector and transfection technique used, only a small fraction of cells can integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding envelope or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) envelope protein. Accordingly, the invention further provides methods for producing envelope protein using the host cells of the invention. In one embodiment, the method comprises culturing the host cell of invention (into which a recombinant expression vector encoding envelope has been introduced) in a suitable medium until envelope is produced. In another embodiment, the method further comprises isolating envelope from the medium or the host cell.

III. Isolated Envelope Polypeptides and Anti-Envelope Polypeptide/Trimer Antibodies The present invention further provides isolated envelope polypeptides, or fragments thereof. In one aspect, an envelope polypeptide can comprise a full-length envelope amino acid sequence or a full-length envelope amino acid sequence with 1, 2, 3, 4, 5, 6, 7, 8, 9, 10, 11, 12, 13, 14, 15, 16, 17, 18, 19, or 20 or more 20 conservative amino acid substitutions. In one embodiment, the envelope polypeptides have an envelope polypeptide amino acid sequence shown in Table 4 that further has one or more mutated residues listed in Tables 6-9, or a fragment thereof. In another embodiment, the envelope polypeptides have an amino acid sequence that is at least 50, 55, 60, 65, 70, 75, 80, 85, 90, 91, 92, 93, 94, 95, 96, 97, 98, 99, or 99.5% identical to the entire amino acid sequence of an envelope polypeptide amino acid sequence shown in Table 4 that further has one or more mutated residues listed in Tables 6-9, or a fragment thereof. In addition, any envelope polypeptide of the present invention, or fragment thereof, forms a stable trimer complex that maintains or enhances one or more of the following biological activities: a) the conformation of the native trimer complex in the absence of the one or more mutated residues; b) the conformation of a trimer complex shown in any one of FIGS. 1-17; c) epitopes bound by broadly neutralizing antibodies, (b) resistance to antibody neutralization by CD4, (c) amino acid inter-residue interactions predicted for the mutated residues, (d) complex binding to ligands CD4, CCR5 or CXCR4, (e) reduction in complex lability, (f) prevention of dissociation of complex protomers and/or (g) complex tensegrity. In another aspect, the present invention contemplates a composition comprising an isolated envelope polypeptide and less than about 25%, or alternatively 15%, or alternatively 5%, contaminating biological macromolecules or polypeptides.

In certain embodiments, an envelope polypeptide of the invention can be a fusion protein containing a domain which increases its solubility and bioavailability and/or facilitates its purification, identification, detection, and/or structural characterization. In such embodiments, the heterologous portions should not substantially alter the immunogenic conformation of envelope trimers. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, an envelope polypeptide of the invention can comprise one or more heterologous fusions. Polypeptides can contain multiple copies of the same fusion domain or can contain fusions to two or more different domains. The fusions can occur within the polypeptide as an in-frame insertion, at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In another embodiment, the polypeptide can be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, envelope polypeptides, or fragments thereof, are fused to an antibody fragment (e.g., Fc polypeptides). Techniques for preparing these fusion proteins are known, and are described, for example, in WO 99/31241 and in Cosman et. al., 2001 Immunity 14:123 133. Fusion to an Fc polypeptide offers the additional advantage of facilitating purification by affinity chromatography over Protein A or Protein G columns.

In still another embodiment, an envelope polypeptide can be labeled with a fluorescent label to facilitate their detection, purification, or structural characterization. In an exemplary embodiment, an envelope polypeptide of the invention can be fused to a heterologous polypeptide sequence which produces a detectable fluorescent signal, including, for example, green fluorescent protein (GFP), enhanced green fluorescent protein (EGFP), *Renilla reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Fragments or biologically active portions of the envelope proteins can include polypeptides comprising amino acid sequences derived from the amino acid sequence of the envelope protein, e.g., an envelope polypeptide amino acid sequence shown in Table 4 that further has one or more mutated residues listed in Tables 6-9, or fragment thereof, which include fewer amino acids than the full-length envelope protein, and exhibit at least one activity of the envelope protein, or complex thereof. In one embodiment, an envelope protein can have 1, 2, 3, 4, 5, 6, 7, 8, 9, 10, 11, 12, 13, 14, 15, 16, 17, 18, 19, 20 or more fewer amino acids, whether contiguous or not contiguous. For example, deletion or replacement of certain sequences (e.g., the proteolytic cleavage site, signal sequence, and the like) that do not substantially affect the immunogenic conformation of native envelope trimers are contemplated.

Envelope proteins described herein can be produced by recombinant DNA techniques. For example, a nucleic acid molecule encoding the protein is cloned into an expression vector (as described above), the expression vector is introduced into a host cell (as described above) and the envelope protein is expressed in the host cell. The envelope protein can then be isolated from the cells by an appropriate purification scheme using standard protein purification techniques. Alternative to recombinant expression, an envelope protein, polypeptide, or peptide can be synthesized chemically using standard peptide synthesis techniques. Moreover, native envelope protein can be isolated from cells (e.g., lymphoma cells), for example, using an anti-envelope antibody (described further below).

The present invention further provides envelope trimer complexes formed by the envelope polypeptides of the present invention. In one embodiment, either envelope proteins or trimer complexes thereof (e.g., envelope glycoprotein trimer complexes), can be used as immunogens to generate neutralizing agents (e.g., antibodies, aptamers, and the like) that bind envelope polypeptides or trimer complexes thereof, using standard techniques for polyclonal and monoclonal antibody preparation. The full-length envelope protein can be used or, alternatively, antigenic peptide fragments of envelope, or peptides in complex, can be used as immunogens. An envelope polypeptide or trimer thereof of the present invention can be used to prepare antibodies by immunizing a suitable subject, (e.g., human, monkey, rabbit, goat, mouse or other mammal) with the immunogen as further described herein. An appropriate immunogenic preparation can contain, for example, recombinantly expressed envelope protein or a chemically synthesized envelope polypeptide or trimer thereof. The preparation can further include an adjuvant, such as Freund's complete or incomplete adjuvant, or similar immunostimulatory agent. Immunization of a suitable subject with an immunogenic envelope polypeptide or trimer thereof that induces a polyclonal anti-envelope antibody response.

Accordingly, another aspect of the invention pertains to the use of anti-envelope antibodies. The term "antibody" as used herein refers to immunoglobulin molecules and immunologically active portions of immunoglobulin molecules, i.e., molecules that contain an antigen binding site which specifically binds (immunoreacts with) an antigen, such as envelope. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind envelope. The term "monoclonal antibody" or "monoclonal antibody composition", as used herein, refers to a population of antibody molecules that contain only one species of an antigen binding site capable of immunoreacting with a particular epitope of envelope. A monoclonal antibody composition thus typically displays a single binding affinity for a particular envelope protein with which it immunoreacts.

Polyclonal anti-envelope antibodies can be prepared as described above by immunizing a suitable subject with an envelope immunogen, or fragment thereof. The anti-envelope antibody titer in the immunized subject can be monitored over time by standard techniques, such as with an enzyme linked immunosorbent assay (ELISA) using immobilized envelope. If desired, the antibody molecules directed against envelope can be isolated from the mammal (e.g., from the blood) and further purified by well-known techniques, such as protein A chromatography to obtain the IgG fraction. At an appropriate time after immunization, i.e., when the anti-envelope antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with an envelope immunogen as described above, and the culture supernatants of the resulting hybridoma cells are screened to identify a hybridoma producing a monoclonal antibody that binds envelope.

Any of the many well-known protocols used for fusing lymphocytes and immortalized cell lines can be applied for the purpose of generating an anti-envelope monoclonal antibody (see, i.e., G. Galfre et al. (1977) *Nature* 266:550-52; Gefter et al. *Somatic Cell Genet.*, cited supra; Lerner, *Yale J. Biol. Med.*, cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypo- xanthine, aminopterin and thymidine ("HAT medium"). Any of a number of myeloma cell lines can be used as a fusion partner according to standard techniques, i.e., the P3-NS1/1Ag4-1, P3-x63Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind envelope, i.e., using a standard ELISA assay.

Additionally, recombinant anti-envelope polypeptide and/or anti-envelope trimer antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-envelope polypeptide and/or anti-envelope trimer antibody (e.g., monoclonal antibody) can be used to isolate and/or detect (e.g., in diagnostic assays) envelope polypeptides by standard techniques, such as affinity chromatography or immunoprecipitation. An anti-envelope polypeptide and/or anti-envelope trimer antibody can facilitate the purification of natural envelope polypeptides from cells and of recombinantly produced envelope expressed in host cells. Moreover, an anti-envelope polypeptide and/or anti-envelope trimer antibody can be used to detect envelope proteins or trimers thereof (e.g., in a cellular lysate or cell supernatant) in order to evaluate the abundance and pattern of expression of the envelope protein. In some embodiments, for example, such antibodies can be used in quantitative immunohistochemical assays to determine PIV viral loads. Thus, anti-envelope antibodies can be used to monitor protein levels in a cell or tissue, e.g., cells or tissues infected with a PIV, as part of a clinical testing procedure, e.g., in order to monitor the efficacy of an anti-PIV therapy. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In vivo techniques for detection of envelope protein include introducing into a subject a labeled antibody directed against the protein. For example, the antibody can be labeled with a radioactive marker whose presence and location in a subject can be detected by standard imaging techniques.

IV. Identification of Agents that Modulate Envelope Polypeptides and Trimers Thereof The envelope nucleic acid and polypeptide molecules described herein can be used to design modulators of one or more of biological activities of the complex or complex polypeptides. In particular, information useful for the design of therapeutic and diagnostic molecules, including, for example, the protein domain, structural information, and the like for polypeptides of the present invention is described herein.

In one aspect, modulators, inhibitors, or antagonists directed against the envelope polypeptides of the present invention and trimers thereof and biological complexes containing them (e.g., natural or synthetic lipid membranes containing envelope trimers) can be used for therapeutic, prognostic, and diagnostic purposes. In certain exemplary embodiments, screening assays for identifying modulators, i.e., candidate or test compounds or agents (e.g., antibodies, peptides, cyclic peptides, peptidomimetics, small molecules, small organic molecules, or other drugs) which have an inhibitory effect on envelope polypeptides or trimers thereof and/or one or more PIV-mediated activities described herein are provided.

Modulators of envelope polypeptides and trimers thereof can be identified and developed as described herein using techniques and methods known to those of skill in the art. The modulators of the invention can be employed, for instance, to inhibit and treat PIV infections or PIV-mediated disorders. The modulators of the invention can elicit a change in one or more of the following activities: (a) a change in the level and/or rate of formation of an envelope trimer complex, (b) a change in the activity of an envelope nucleic acid and/or polypeptide, (c) a change in the stability of an envelope nucleic acid or polypeptide/trimer, (d) a change in the conformation of an envelope nucleic acid or polypeptide/trimer, or (e) a change in the activity of at least one polypeptide contained in an envelope trimer complex. A number of methods for identifying a molecule which modulates an envelope nucleic acid and/or polypeptide are known in the art. For example, in one such method, an envelope nucleic acid or polypeptide/trimer is contacted with a test compound and the activity of the envelope nucleic acid or polypeptide/trimer is determined in the presence of the test compound, wherein a change in the activity of the envelope nucleic acid and/or polypeptide in the presence of the compound as compared to the activity in the absence of the compound (or in the presence of a control compound) indicates that the test compound modulates the activity of the envelope nucleic acid and/or polypeptide.

Compounds to be tested for their ability to act as modulators of envelope nucleic acids or polypeptide/trimer, can be produced, for example, by bacteria, yeast or other organisms (e.g. natural products), produced chemically (e.g. small molecules, including peptidomimetics), or produced recombinantly. Compounds for use with the above-described methods can be selected from the group of compounds consisting of lipids, carbohydrates, polypeptides, peptidomimetics, peptide-nucleic acids (PNAs), small molecules, natural products, aptamers and polynucleotides. In certain embodiments, the compound is a polynucleotide. In certain embodiments, the compound comprises a biologically active fragment of an envelope polypeptide (e.g., a dominant negative form that binds to, but does not activate, envelope).

A variety of assay formats will suffice and, in light of the present disclosure, those not expressly described herein can nevertheless be comprehended by one of ordinary skill in the art based on the teachings herein. Assay formats for analyzing envelope trimer complex formation and/or activity of an envelope nucleic acid and/or polypeptide can be generated in many different forms and include assays based on cell-free systems, e.g. purified proteins or cell lysates, as well as cell-based assays which utilize intact cells. Simple binding assays can also be used to detect agents which modulate an envelope nucleic acid or polypeptide/trimer, for example, by enhancing the formation of an envelope trimer complex and/or by enhancing the binding of an envelope polypeptide to trimer complex to a substrate. Another example of an assay useful for identifying a modulator of an envelope is a competitive assay that combines one or more envelope polypeptides with a potential modulator, such as, for example, polypeptides, nucleic acids, natural substrates or ligands, antibodies, or substrate or ligand mimetics, under appropriate conditions for a competitive inhibition assay. Envelope polypeptides/trimers can be labeled, such as by radioactivity or a colorimetric compound, such that envelope complex formation and/or activity can be determined accurately to assess the effectiveness of the potential modulator.

Assays can employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof. Assays can also employ any of the methods for isolating, preparing and detecting envelopes polypeptides or complexes, as described above.

Complex formation between an envelope polypeptide, or fragment thereof, and a binding partner (e.g., CD4, CCR5, or CXCR) can be detected by a variety of methods. Modulation of the complex's formation can be quantified using, for example, detectably labeled proteins such as radiolabeled, fluorescently labeled, or enzymatically labeled polypeptides or binding partners, by immunoassay, or by chromatographic detection. Methods of isolating and identifying envelop trimer complexes described above can be incorporated into the detection methods.

In certain embodiments, it can be desirable to immobilize an envelope polypeptide to facilitate separation of envelope trimer complexes from uncomplexed enveloped polypeptides, as well as to accommodate automation of the assay. In any case, binding of an envelope polypeptide or a trimer complex thereof to a binding partner can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/polypeptide (GST/polypeptide) fusion proteins can be adsorbed onto glutathione sepharose beads (Sigma Chemical, St. Louis, Mo.) or glutathione derivatized microtitre plates, which are then combined with the binding partner, e.g. an $^{35}$S-labeled binding partner, and the test compound, and the mixture incubated under conditions conducive to complex formation, e.g. at physiological conditions for salt and pH, though slightly more stringent conditions can be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of envelope polypeptides found in the bead fraction quantified from the gel using standard electrophoretic techniques such as described in the appended examples.

Other techniques for immobilizing proteins on matrices are also available for use in the subject assay. For instance, an envelope polypeptide or trimer thereof can be immobilized utilizing conjugation of biotin and streptavidin. For instance, biotinylated polypeptide molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the polypeptide can be derivatized to the wells of the plate, and polypeptide trapped in the wells by antibody conjugation. As above, preparations of a binding partner and a test compound are incubated in the polypeptide presenting wells of the plate, and the amount of complex trapped in the well can be quantified. Exemplary methods for detecting such complexes, in addition to those described above for the GST-immobilized complexes, include immunodetection of complexes using antibodies reactive with the binding partner, or which are reactive with the envelope polypeptide and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the binding partner.

Antibodies against the envelope polypeptide can be used for immunodetection purposes. Alternatively, the envelope polypeptide to be detected can be "epitope-tagged" in the form of a fusion protein that includes, in addition to the polypeptide sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150-21157) which includes a 10-residue sequence from c-myc, as well as the pFLAG system (International Biotechnologies, Inc.) or the pEZZ-protein A system (Pharmacia, N.J.).

In certain in vitro embodiments of the present assay, the protein or the set of proteins engaged in a protein-protein, protein-substrate, or protein-nucleic acid interaction comprises a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-substrate, protein-protein or nucleic acid-protein interaction are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-substrate, protein-protein interaction, or nucleic acid-protein interaction.

In one embodiment, the use of reconstituted protein mixtures allows more careful control of the protein-substrate, protein-protein, or nucleic acid-protein interaction conditions. Moreover, the system can be derived to favor discovery of modulators of particular intermediate states of the protein-protein interaction. For instance, a reconstituted protein assay can be carried out both in the presence and absence of a candidate agent, thereby allowing detection of a modulator of a given protein-substrate, protein-protein, or nucleic acid-protein interaction.

Assaying biological activity resulting from a given protein-substrate, protein-protein or nucleic acid-protein interaction, in the presence and absence of a candidate modulator, can be accomplished in any vessel suitable for containing the reactants. Examples include microtitre plates, test tubes, and micro-centrifuge tubes.

In still further embodiments, the envelope polypeptide or trimer complex thereof can be generated in whole cells, taking advantage of cell culture techniques to support the subject assay. For example, the envelope polypeptide or trimer complex thereof, can be constituted in a prokaryotic or eukaryotic cell culture system. This allows for an environment more closely approximating that which therapeutic use of the modulator would require, including the ability of the agent to gain entry into the cell. Furthermore, certain of the in vivo embodiments of the assay are amenable to high through-put analysis of candidate agents.

Some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high through-put analysis in that proliferation of the cell can provide a simple measure of the protein-protein interaction.

The amount of transcription from the reporter gene can be measured using any method known to those of skill in the art to be suitable. For example, specific mRNA expression can be detected using Northern blots or specific protein product can be identified by a characteristic stain, western blots or an intrinsic activity. In certain embodiments, the product of the reporter gene is detected by an intrinsic activity associated with that product. For instance, the reporter gene can encode a gene product that, by enzymatic activity, gives rise to a detection signal based on color, fluorescence, or luminescence.

In many drug screening programs which test libraries of compounds and natural extracts, high throughput assays are desirable in order to maximize the number of compounds surveyed in a given period of time. Assays of the present invention which are performed in cell-free systems, such as can be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as can be manifest in an alteration of binding affinity with other proteins or changes in enzymatic properties of the molecular target. Accordingly, potential modulators of envelope can be detected in a cell-free assay generated by constitution of a functional envelope polypeptide or trimer complex thereof in a cell lysate. In an alternate format, the assay can be derived as a reconstituted protein mixture which, as described below, offers a number of benefits over lysate-based assays.

The activity of an envelope polypeptide or trimer complex thereof can be identified and/or assayed using a variety of methods well known to the skilled artisan. For example, the activity of an envelope nucleic acid and/or polypeptide can be determined by assaying for the level of expression of RNA and/or protein molecules. Transcription levels can be determined, for example, using Northern blots, hybridization to an oligonucleotide array or by assaying for the level of a resulting protein product. Translation levels can be determined, for example, using Western blotting or by identifying a detectable signal produced by a protein product (e.g., fluorescence, luminescence, enzymatic activity, etc.). Depending on the particular situation, it can be desirable to detect the level of transcription and/or translation of a single gene or of multiple genes. Similarly, it can be desirable to determine the status of stability-enhancing modifications made to the envelope polypeptides of the present invention (e.g., analyzing the production of disulfide bonds in Cys-Cys modifications and the like).

In other embodiments, the biological activity of an envelope nucleic acid and/or polypeptide can be assessed by monitoring changes in the phenotype of a targeted cell. For example, the detection means can include a reporter gene construct which includes a transcriptional regulatory element that is dependent in some form on the level and/or activity of an envelope nucleic acid and/or polypeptide. The envelope nucleic acid and/or polypeptide can be provided as a fusion protein with a domain that binds to a DNA element of a reporter gene construct. The added domain of the fusion protein can be one which, through its DNA binding ability, increases or decreases transcription of the reporter gene. Whichever the case can be, its presence in the fusion protein renders it responsive to an envelope nucleic acid and/or polypeptide. Accordingly, the level of expression of the reporter gene will vary with the level of expression of an envelope nucleic acid and/or polypeptide.

Moreover, in the whole cell embodiments of the subject assay, the reporter gene construct can provide, upon expression, a selectable marker. A reporter gene includes any gene that expresses a detectable gene product, which can be RNA or protein. Preferred reporter genes are those that are readily detectable. The reporter gene can also be included in the construct in the form of a fusion gene with a gene that includes desired transcriptional regulatory sequences or exhibits other desirable properties. For instance, the product of the reporter gene can be an enzyme which confers resistance to an antibiotic or other drug, or an enzyme which complements a deficiency in the host cell (i.e. thymidine kinase or dihydrofolate reductase). To illustrate, the aminoglycoside phosphotransferase encoded by the bacterial transposon gene Tn5 neo can be placed under transcriptional control of a promoter element responsive to the level of an envelope nucleic acid and/or polypeptide present in the cell. Such embodiments of the subject assay are particularly amenable to high through-put analysis in that proliferation of the cell can provide a simple measure of inhibition of the envelope nucleic acid and/or polypeptide.

V. Methods of the Invention a. Methods of using immunogens

In one aspect, the present invention provides compositions useful as immunogens (e.g., trimeric complexes, polypeptides, nucleic acids, vectors, host cells, immunogenic compositions, and the like described herein). Such immunogens can be administered in any of a number of routes known in the art (e.g., to be compatible with eliciting strong antibody responses). Administration can be by injection, infusion, aerosol, oral, transdermal, transmucosal, intrapleural, intrathecal, or other suitable routes. Preferably, the composition is administered by intravenous, subcutaneous, intradermal, or intramuscular routes, or any combination thereof. The immunization protocol can include at least one priming dose, followed by one or multiple boosting doses administered over time. An exemplary range for an immunogenically effective amount of the present immunogenic polypeptides is about 5 to about 500 μg/kg body weight. A preferred range is about 10-100 μg/kg.

In one embodiment, one or more unit doses of the immunogen are given at one, two or three time points. The optimal number and timing of boosts can readily be determined using routine experimentation. Exemplary "prime-boost" regimens are described in U.S. Pat. No. 6,210,663 and WO 00/44410. In one embodiment, a priming composition is a replication-competent or replication-defective recombinant virus containing a nucleic acid molecule encoding the antigen, or a viral-like particle. In one particular embodiment, the priming composition is a non-replicating recombinant virus or viral-like particle derived from a PIV.

One method according to the present invention involves "priming" a mammalian subject by administration of a priming composition. "Priming," as used herein, means any method whereby a first immunization using an antigen permits the generation of an immune response to the antigen upon a second immunization with the same antigen, wherein the second immune response is greater than that achieved where the first immunization is not provided.

Preferably, a boosting composition is administered about 2 to 27 weeks after administering the priming composition to a mammalian subject. The administration of the boosting composition is accomplished using an effective amount of a boosting composition containing or capable of delivering the same antigen as administered by the priming composition. As used herein, the term "boosting composition" includes, as one embodiment, a composition containing the same antigen as in the priming composition or precursor thereof, but in a different form, in which the boosting composition induces an immune response in the host. In one particular embodiment, the boosting composition comprises a recombinant soluble protein.

In one embodiment, a boosting composition is a replication-competent or replication-defective recombinant virus containing the DNA sequence encoding the protein antigen. In another embodiment, the boosting composition is a non-replicating alphavirus comprising a nucleic acid molecule encoding the protein antigen or a non-replicating vaccine replicon particle derived from an alphavirus. Adenoviruses, which naturally invade their host through the airways, infect cells of the airways readily upon intranasal application and induce a strong immune response without the need for adjuvants. In another embodiment, the boosting composition comprises a replication-defective recombinant adenovirus. Another example of a boosting composition is a bacterial recombinant vector containing the DNA sequence encoding the antigen in operable association with regulatory sequences directing expression of the antigen in tissues of the mammal. One example is a recombinant BCG vector.

Other examples include recombinant bacterial vectors based on *Salmonella, Shigella*, and *Listeria*, among others. Still another example of a boosting composition is a naked DNA sequence encoding the antigen in operable association with regulatory sequences directing expression of the antigen in tissues of the mammal but containing no additional vector sequences. These vaccines can further contain pharmaceutically suitable or physiologically acceptable carriers. In still additional embodiments, the boosting compositions can include proteins or peptides (intact and denatured), heat-killed recombinant vaccines, inactivated whole microorganisms, antigen-presenting cells pulsed with the instant proteins or infected/transfected with a nucleic acid molecule encoding same, and the like, all with or without adjuvants, chemokines and/or cytokines.

Representative forms of antigenic immunogens include a "naked" DNA plasmid, a "naked" RNA molecule, a DNA molecule packaged into a replicating or nonreplicating viral vector, an RNA molecule packaged into a replicating or nonreplicating viral vector, a DNA molecule packaged into a bacterial vector, or proteinaceous forms of the antigen alone or present in virus-like particles, or combinations thereof.

In one embodiment, recombinant envelope polypeptides and trimers thereof, can be administered to subjects. In some embodiments, fusion proteins can be constructed and administered which have enhanced biological properties. In addition, the polypeptides can be modified according to well-known pharmacological methods in the art (e.g., pegylation, glycosylation, oligomerization, etc.) in order to further enhance desirable biological activities, such as increased immunogenicity, bioavailability, and/or decreased proteolytic degradation.

In one embodiment, "virus-like particles" or "VLPs" can be used, which are non-infectious particles in any host and do not contain all of the protein components of live virus particles. In one embodiment, VLPs contain the stabilized envelope glycoprotein trimers or polypeptides described herein and form membrane-enveloped virus-like particles. The advantages of using VLPs include (1) their particulate and multivalent nature, which is immunostimulatory, and (2) their ability to present the disulfide-stabilized envelope glycoproteins in a near-native, membrane-associated form. VLPs are produced by co-expressing the viral proteins (e.g., stabilized envelope glycoprotein trimers or polypeptides described herein) in the same cell. This can be achieved by any of several means of heterologous gene expression that are well-known to those skilled in the art, such as transfection of appropriate expression vector(s) encoding the viral proteins, infection of cells with one or more recombinant viruses (e.g., vaccinia) that encode the VLP proteins, or retroviral transduction of the cells. A combination of such approaches can also be used. The VLPs can be produced either in vitro or in vivo. VLPs can be produced in purified form by methods that are well-known to the skilled artisan, including centrifugation, as on sucrose or other layering substance, and by chromatography.

For embodiments using instant nucleic acid delivery, any means for the introduction of a polynucleotide into a subject, such as a human or non-human mammal, or cells thereof can be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs can first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, can then be effected using known methods and materials and delivered to the recipient mammal. See, e.g., Canonico et al., Am J Respir Cell Mol Biol 10:24-29, 1994; Tsan et al., Am J Physiol 268; Alton et al., Nat Genet. 5:135-142, 1993; and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system can be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest can be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter can be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences, such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued Can 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxvirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

Immunogens can be administered together with an adjuvant or other immunostimulant. Thus, the immunogens can further comprise one or more adjuvants or immunostimulating agents, which are preferably added to the fusion protein immunogens using for boosting the immune response. An adjuvant is any substance that can be added to an immunogen or to a vaccine formulation to enhance the immune-stimulating properties of the immunogenic moiety, such as a protein or polypeptide. Liposomes are also considered to be adjuvants. See, for example, Gregoriades, G. et al., Immunological Adjuvants and Vaccines, Plenum Press, New York, 1989; Michalek, S. M. et al., Liposomes as Oral Adjuvants, Curr. Top. Microbiol. Immunol. 146:51-58 (1989). Examples of adjuvants or agents that can add to the effectiveness of immunogens include aluminum hydroxide, aluminum phosphate, aluminum potassium sulfate (alum), beryllium sulfate, silica, kaolin, carbon, water-in-oil emulsions, and oil-in-water emulsions. Other adjuvants are muramyl dipeptide (MDP) and various MDP derivatives and formulations, e.g., N-acetyl-D-glucosaminyl-($\beta$,1-4)-N-acetylmuramyl-L-alanyl-D-isoglutamine (GMDP) (Hornung, R L et al., Ther Immunol 1995 2:7-14) or ISAF-1 (5% squalene, 2.5% pluronic L121, 0.2% Tween 80 in phosphate-buffered solution with 0.4 mg of threonyl-muramyl dipeptide; see Kwak, L W et al., (1992) N. Engl. J. Med., 327: 1209-1238) and monophosphoryl lipid A adjuvant solubilized in 0.02% triethanolamine. Other useful adjuvants are, or are based on, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives such as QS21 (White, A. C. et al. (1991) Adv. Exp. Med. Biol., 303:207-210) which is now in use in the clinic (Helling, F et al. (1995) Cancer Res., 55:2783-2788; Davis, T A et al. (1997) Blood, 90: 509A (abstr.)), levamisole, DEAE-dextran, blocked copolymers or other synthetic adjuvants. Examples of commercially available adjuvants include (a) Amphigen®, which is an oil-in-water adjuvant made of de-oiled lecithin dissolved in oil (see for example, U.S. Pat. No. 5,084,269 and US Pat Publication 20050058667A1 and (b) Alhydrogel®, which is an aluminum hydroxide gel. Aluminum is approved for human use. Adjuvants are available commercially from various sources, for example, Merck Adjuvant 65@ (Merck and Company, Inc., Rahway, N.J.). The immunogenic material can be adsorbed to or conjugated to beads such as latex or gold beads, ISCOMs, and the like. There is evidence that traditional formulations, such as Freund's adjuvant (both complete and incomplete) and Alum gel at least partially denature antigen resulting in the destruction or under-representation of conformational epitopes. The Ribi adjuvant system (RAS), which belongs to the monophosphoryl-lipid A (MPL) containing-adjuvants, can be used to overcome this problem. Results from several studies indicate that antigen formulated using MPL-containing adjuvants elicited antibodies that preferentially bound native rather than denatured antigen (Earl, P. L., et al., J. Virol 68:3015-3026 (1994); VanCott T. C., et al., J. Virol 71:4319-4330 (1997)).

Immunogens can also be supplemented with an immunostimulatory cytokine, lymphokine or chemokine. Exemplary cytokines include, without limitation, GM-CSF (granulocyte-macrophage colony stimulating factor), interleukin 1, interleukin 2, interleukin 12, interleukin 18 or interferon-gamma.

General methods to prepare immunogenic pharmaceutical compositions and vaccines are well known in the art (see, for example, Remington's Pharmaceutical Science; Mack Publishing Company Easton, Pa.).

b. Evaluating Immunogen-Elicited Responses

In one aspect, the present invention provides immunogens that can be used to raise antiviral neutralizing agents (e.g., antibodies and aptamers) by methods known to those of ordinary skill in the art. The antibodies raised can then be administered to a PIV-infected or non-PIV-infected subject for a variety of uses. In one embodiment involving hybridoma production, samples can be screened by a number of techniques to characterize binding to immunogens described herein. One approach involves ELISA binding to the inventive immunogens. Animals with sera samples which test positive for binding to one or more immunogens are candidates for use in MAb production. The criteria for selection of animals to be used in MAb production is based on the evidence of neutralizing antibody in the animals' sera or in the absence of neutralization, appropriate binding patterns against the desired immunogens.

Hybridoma supernatants derived from MAb production can be screened for ELISA, lysate and surface immunoprecipitation assays for binding to the desired immunogen. Samples which are positive in any of the binding assays can be screened for their ability to neutralize PIVs of interest. For example, PIV species, strains, or isolates can include lab adapted and primary virus strains, syncytium- and non-syncytium-inducing isolates, virus representing various geographic subtypes, and viral isolates which make use of the range of second receptors during virus entry. The neutralization assays employ either primary cell or cell line targets as required.

Advances in the field of immunology have allowed more thorough and sensitive evaluations of cellular responses to candidate immunogens and immunogenic compositions (e.g., vaccines) against PIVs. Such assays as intracellular staining (e.g., flow cytometry) and ELISPOT (an enzyme-linked immunosorbent assay format) allow for the detection and counting of cells producing molecules, such as antibodies and cytokines, indicative of a response to stimulation by an antigen. For example, isolation of splenocytes or peripheral blood monocyte cells (PBMCs) from an animal or human followed by in vitro challenge with an appropriately presented PIV epitope, and finally testing by ELISPOT and/or intracellular cytokine staining (ICS), can determine the potential for a cell-mediated immune response in recipients having been administered an immunogen.

In one embodiment, ELISA and Western blots are used to assess the antibody response. These methods can assess antibody binding, antibody neutralizing capability, antibody-mediated fusion inhibition, and antibody-dependent cytotoxicity. Such methods are well known in the art. For example, an MT-2 assay can be performed to measure neutralizing antibody responses. Antibody-mediated neutralization of a selected strains or isolates of a PIV can be measured in an MT-2 cell-killing assay (D. Montefiori et al., 1988, J. Clin. Microbial., 26:231-7). The inhibition of the formation of syncytia by the sera shows the activity of neutralizing antibodies present within the sera, induced by vaccination. Immunized test and control sera can be exposed to virus-infected cells (e.g., cells of the MT-2 cell line). Neutralization can be measured by any method that determines viable cells, such as staining, e.g., with Finter's neutral red. The percentage of protected cells can be determined by calculating the difference in absorption ($A_{540}$) between test wells (cells and virus) and dividing this result by the difference in absorption between cell control wells (cells only) and virus control wells (virus only). Neutralizing titers can be expressed, for example, as the reciprocal of the plasma dilution required to protect at least 50% of cells from virus-induced killing.

In another embodiment, antiviral activity of neutralizing antibodies generated by the immunization with vaccine immunogens can be evaluated in both cell-cell fusion and neutralization assays. In the latter assay, a representative sample of lab adapted and primary virus isolates is used. Both assays are carried out according to known protocols as described in, for example, Wild et al. (1992) PNAS USA 89:10537-10541; Wild et al. (1994) PNAS USA 91:12676-12680; and Wild et al. (1994) PNAS USA 91:9770-9774. For example, in the neutralization assay, test sera can be incubated at a 1:10 dilution with virus for 1 hour at 37° C. At the end of this time, target cells can be added and the experiment returned to the incubator. On days 1, 3 and 5, post-infection complete media changes can be carried out. On day 7, PI culture supernatant can be harvested. Levels of virus replication can then be determined by p24 antigen capture. Levels of replication in test wells can be normalized against virus-only controls.

In still another embodiment, an assay can be used that determines an agent's ability to inhibit infectivity of PIV particles. For example, HeLa cells stably expressing human CD4 and CCR5 receptors and harboring a beta-galactosidase reporter gene driven by a tat-responsive fragment of a PIV long terminal repeat (LTR, such as HIV-2 LTR) can be infected with a PIV of various strains in the presence of a candidate neutralizing agent at varying concentrations. After incubating said cells for a specific period of time, the cells are lysed and beta-galactosidase activity is quantified. A lower beta-galactosidase activity recording indicates that the agent has an increased ability to inhibit PIV infectivity.

For any assay described herein, results from test agents can be compared against titration or positive controls (e.g., known broadly neutralizing antibodies) for normalization purposes.

c. Diagnostic, Prognostic and Therapeutic Methods

In one aspect, the present invention provides a method of preventing a subject from becoming infected with a primate immunodeficiency virus comprising administering to the subject a prophylactically effective amount of an immune response-eliciting agent described herein to thereby prevent the subject from becoming infected with the primate immunodeficiency virus.

In another aspect, the present invention provides a method for reducing the likelihood of a subject's becoming infected with a primate immunodeficiency virus comprising administering to the subject a prophylactically effective amount of an immune response-eliciting agent described herein to thereby reducing the likelihood of the subject's becoming infected with the primate immunodeficiency virus.

In still another aspect, the present invention provides a method for preventing or delaying the onset of, or slowing the rate of progression of, a primate immunodeficiency virus-related disease in a subject infected with a primate immunodeficiency virus, comprising administering to the subject a therapeutically effective amount of an immune response-eliciting agent described herein to thereby prevent or delay the onset of, or slowing the rate of progression of, the primate immunodeficiency virus-related disease in the subject.

Thus, in some embodiments, the immunogens described herein can be used to immunize a PIV-infected subject such that levels of PIV will be reduced in the subject. In other embodiments, the immunogens described herein can be employed to immunize a non-PIV-infected subject so that, following a subsequent exposure to a PIV that would normally result in a PIV infection, the level of PIV will be reduced or non-detectable using current diagnostic tests. In some embodiments, the immune response is a B cell response, a T cell response, or a combination thereof.

It will be appreciated that individual dosages can be varied depending upon the requirements of the subject in the judgment of the attending clinician, the severity of the condition being treated and the particular compound being employed. In determining the therapeutically effective amount or dose, a number of additional factors can be considered by the attending clinician, including, but not limited to: the pharmacodynamic characteristics of the particular agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage can be divided and administered in portions during the day if desired.

The duration and/or dose of treatment with antiviral therapies can vary according to the particular agent or combination thereof. An appropriate treatment time for a particular antiviral therapeutic agent will be appreciated by the skilled artisan. The invention contemplates the continued assessment of optimal treatment schedules for each antiviral therapeutic agent, where the phenotype of the PIV infection of the subject as determined by the methods of the invention is a factor in determining optimal treatment doses and schedules.

In general, it is preferable to obtain a first sample from the subject prior to beginning therapy and one or more samples during treatment. In such a use, a baseline of expression of cells from subjects with a PIV infection or related disorders prior to therapy is determined and then changes in the baseline state of expression of cells from subjects with a PIV infection or related disorders is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with a PIV infection or related disorders is increasing or decreasing.

It may further be advantageous to administer the immunogenic compositions disclosed herein with other agents, such as proteins, peptides, antibodies, and other anti-PIV agents. Examples of such anti-PIV therapeutic agents include nucleoside reverse transcriptase inhibitors, such as abacavir, AZT, didanosine, emtricitabine, lamivudine, stavudine, tenofovir, zalcitabine, zidovudine, and the like, non-nucleoside reverse transcriptase inhibitors, such as delavirdine, efavirenz, nevirapine, protease inhibitors such as amprenavir, atazanavir, indinavir, lopinavir, nelfinavir osamprenavir, ritonavir, saquinavir, tipranavir, and the like, and fusion protein inhibitors such as enfuvirtide and the like. In certain embodiments, immunonogenic compositions are administered concurrently with other anti-PIV therapeutic agents. In certain embodiments, the immunonogenic compositions are administered sequentially with other anti-PIV therapeutic agents, such as before or after the other agent. One of ordinary skill in the art would know that sequential administration can mean immediately following or after an appropriate period of time, such as hours days, weeks, months, or even years later.

VI. Pharmaceutical Compositions

In another aspect, the present invention provides pharmaceutically acceptable compositions which comprise a therapeutically-effective amount of a composition described herein, formulated together with one or more pharmaceutically acceptable carriers (additives) and/or diluents and with or without additional antiviral agents and/or immunogens. As described in detail below, the pharmaceutical compositions of the present invention can be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., enhances) envelope expression and/or activity, or expression and/or activity of the complex encompassed by the invention. These salts can be prepared in situ during the final isolation and purification of the agents, or by separately reacting a purified agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention can contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., enhances) envelope expression and/or activity, or expression and/or activity of the complex. These salts can likewise be prepared in situ during the final isolation and purification of the agents, or by separately reacting the purified agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations can conveniently be presented in unit dosage form and can be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., increases or decreases) envelope expression and/or activity, with the carrier and, optionally, one or more accessory ingredients. In general, the formulations are prepared by uniformly and intimately bringing into association an agent with liquid carriers, or finely divided solid carriers, or both, and then, if necessary, shaping the product.

Formulations suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. A compound can also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered peptide or peptidomimetic moistened with an inert liquid diluent.

Tablets, and other solid dosage forms, such as dragees, capsules, pills and granules, can optionally be scored or prepared with coatings and shells, such as enteric coatings and other coatings well known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions, which can be dissolved in sterile water, or some other sterile injectable medium immediately before use. These compositions can also optionally contain opacifying agents and can be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration can be presented as a suppository, which can be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., increases or decreases) envelope expression and/or activity include powders, sprays, ointments, pastes, creams, lotions, gels, solutions, patches and inhalants. The active component can be mixed under sterile conditions with a pharmaceutically-acceptable carrier, and with any preservatives, buffers, or propellants which can be required.

The ointments, pastes, creams and gels can contain, in addition to an agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., increases or decreases) envelope expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., increases or decreases) envelope expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of an agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more agents in combination with one or more pharmaceutically-acceptable sterile isotonic aqueous or nonaqueous solutions, dispersions, suspensions or emulsions, or sterile powders which can be reconstituted into sterile injectable solutions or dispersions just prior to use, which can contain antioxidants, buffers, bacteriostats, solutes which render the formulation isotonic with the blood of the intended recipient or suspending or thickening agents.

Examples of suitable aqueous and nonaqueous carriers which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

In some cases, in order to prolong the effect of a drug, it is desirable to slow the absorption of the drug from subcutaneous or intramuscular injection. This can be accomplished by the use of a liquid suspension of crystalline or amorphous material having poor water solubility. The rate of absorption of the drug then depends upon its rate of dissolution, which, in turn, can depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., increases or decreases) envelope expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

Actual dosage levels of the active ingredients in the pharmaceutical compositions of this invention can be determined by the methods of the present invention so as to obtain an amount of the active ingredient, which is effective to achieve the desired therapeutic response for a particular subject, composition, and mode of administration, without being toxic to the subject.

Nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

EXEMPLIFICATION

This invention is further illustrated by the following examples, which should not be construed as limiting.

Example 1: Materials and Methods for Examples 2-11

A. Protein Engineering, Expression, and Purification

The env cDNA was codon-optimised and subcloned into the pcDNA3.1(−) expression plasmid (Invitrogen). The Env (−)ΔCT glycoprotein contains a heterologous signal sequence from CD5 in place of the wild-type HIV-1 Env signal peptide. Site-directed mutagenesis was used to change the proteolytic cleavage site between gp120 and gp41, substituting Ser for Arg508 and Arg511. The Env cytoplasmic tail was truncated by introduction of a stop codon at Tyr712; a sequence encoding a $(Gly)_2(His)_6$ tag was inserted immediately before the stop codon. The plasmid expressing the Env(−)ΔCT glycoprotein was transfected into the 293F cells. After 36 h, cells expressing the envelope glycoproteins were harvested and washed with phosphate-buffered saline (PBS) at 4° C. The cell pellets were homogenized in a homogenization buffer (250 mM sucrose, 10 mM Tris-HCl [pH 7.4]) and a cocktail of protease inhibitors [Roche Complete tablets]). The plasma membranes were then extracted from the homogenates by ultracentrifugation and sucrose gradient separation. The extracted crude plasma membrane pellet was collected and solubilized in a solubilization buffer containing 100 mM $(NH_4)_2SO_4$, 20 mM Tris-HCl (pH 8), 300 mM NaCl, 20 mM imidazole, 1% (wt/vol) Cymal-5 (Affymatrix) and a cocktail of protease inhibitors (Roche Complete tablets). The membranes were solubilized by incubation at 4° C. for 30 min on a rocking platform. The suspension was ultracentrifuged for 30 min at 200,000×g at 4° C. The supernatant was collected and mixed with a small volume of pre-equilibrated Ni-NTA beads (QIAGEN) for 8-12 h on a rocking platform at 4° C. The mixture was then injected into a small column and washed with a buffer containing 100 mM $(NH_4)_2SO_4$, 20 mM Tris-HCl (pH 8), 1 M NaCl, 30 mM imidazole and 0.5% Cymal-5. The bead-filled column was eluted with a buffer containing 100 mM $(NH_4)_2SO_4$, 20 mM Tris-HCl (pH 7.4), 250 mM NaCl, 250 mM imidazole and 0.5% Cymal-5. The eluted Env glycoprotein solution was concentrated, diluted in a buffer containing 20 mM Tris-HCl, pH 7.4, 300 mM NaCl and 0.01% Cymal-6, and reconcentrated to ~2.5 mg ml-1 prior to cryo-sample preparation. The recognition of the purified Env glycoproteins by a number of conformation-dependent antibodies, including VRC01, b12 and 2G12, as well as CD4-Ig, was measured in an enzyme-linked immunosorbent assay (ELISA) (see below). The VRC01 and b12 antibodies recognize conformation-dependent epitopes near the CD4-binding site of gp120 (Zhou et al. (2007) Nature 445:732-737; Wu et al. (2010) Science 329:856-861; Zhou et al. (2010) Science 329:811-817). The 2G12 antibody recognizes a high-mannose glycan array on the gp120 outer domain (Trkola et al. (1996) J. Virol. 70:1100-1108). CD4-Ig consists of the two N-terminal domains of CD4 fused to the Fc portion of the immunoglobulin heavy chain (Finzi et al. (2010) Mol. Cell 37:656-667). Whether the Env solubilization and purification approach affected the integrity of an epitope that is recognized by the PG16 antibody and that is sensitive to changes in the quaternary structure of the HIV-1 Env trimer (Walker et al. (2009) Science 326, 285-289) was also analyzed. To this end, PG16 binding to the Env(−)ΔCT E168K glycoprotein was analyzed. The wild-type HIV-$1_{JR-FL}$ isolate is highly resistant to neutralization by the PG16 antibody, but the E168K change renders the HIV-$1_{JR-FL}$ Env sensitive to PG16. PG16 binding to the purified Env(−)ΔCT E168K glycoprotein was tested in the ELISA.

B. ELISA

A white, high-binding microtiter plate (Corning) was coated by incubating 0.5 μg of mouse anti-histidine antibody (sc-53073, Santa Cruz Biotechnology) in 100 μl PBS in each well overnight. Wells were blocked with blocking buffer (5% non-fat dry milk (Bio-Rad) in 20 mM Tris-HCl, pH 7.4 and 300 mM NaCl) for 2 hours and then washed twice with wash buffer (20 mM Tris-HCl, pH 7.4 and 300 mM NaCl). Approximately 0.5 μg of purified Env trimer in blocking buffer was added to each well, the plate was incubated for 60 minutes and washed thrice with wash buffer. Different concentrations of specific Env ligands (conformation dependent antibodies and the CD4-Ig fusion protein) in blocking buffer were added to the wells and the plate was incubated for another 45 minutes. After three washes, peroxidase-conjugated F(ab')2 fragment donkey anti-human IgG (1:3600 dilution; Jackson ImmunoResearch Laboratories) in blocking buffer was added to each well. The plate was incubated for 30 minutes, washed six times, and 80 μl of SuperSignal chemiluminescent substrate (Pierce) was added to each well. The relative light units in each well were measured for two seconds with a Centro LB 960 luminometer (Berthold Technologies, TN). All procedures were performed at room temperature.

C. Flow Cytometry

HEK293T cells were transfected, by either calcium phosphate coprecipitation or by using the Effectene transfection reagent (Qiagen), with a plasmid encoding the Env(−)ΔCT E168K glycoproteins. After 48 hours, approximately half a million cells were analyzed by flow cytometry as previously described in Herschhorn et al. (2010) J. Immunol. 185:7623-7632, but with primary antibody incubation for 30 minutes, and secondary antibody (Allophycocyanin conjugated F(ab')2 fragment donkey anti-human IgG antibody, Jackson ImmunoResearch Laboratories) incubation for 15 minutes, both at room temperature. Cells were analyzed with a BD FACSCanto II flow cytometer (BD Biosciences).

D. Cryo-EM Reconstruction and Model Analysis

To prepare the cryo-sample for single-particle imaging, 2.5 μl of 2.5 mg/ml Env(−)ΔCT solution was spread on a C-flat holey carbon grid (Electron Microscopy Sciences) in a chamber of 100% humidity, held for 2 seconds, blotted by filter papers for 2 seconds at 4° C., and then flash-plunged into liquid ethane by Vitrobot (FEI). The prepared cryo-grids were transferred into the CT3500 cryo-transfer system (Gatan) in liquid nitrogen and were used for single-particle image data collection at −183° C. Focus pairs of micrographs were recorded on a Tecnai F20 TEM (FEI) with a field-emission gun at 200 kV and a calibrated magnification of 200,835× on a 4 k×4 k slow-scan CCD camera (Gatan). The electron dose of each exposure was 10.0 electrons Å$^{-2}$. The defocus of the second set of micrographs differed from that of the first set by 1.0 μm.

Micrographs were screened for drift, astigmatism and visibility of Thon rings in the power spectra. Parameters of the contrast transfer function (CTF) of each micrograph were determined with the CTFFind3 program (Huang et al. (2003) *J. Struct. Biol.* 144:79-94; Mindell & Grigorieff (2003) *J. Struct. Biol.* 142:334-347). A total of 90,306 single-particle images (in a dimension of 320×320 pixels and a pixel size of 0.747 Å) selected from the closer-to-focus micrographs were used for reconstruction. Each single-particle image was decimated by 4 times to a dimension of 80×80 pixels prior to further image analysis, resulting in a pixel size of 2.99 Å. The images were CTF-corrected by the phase flipping method. These single-particle images were then subjected to multivariate data analysis and classification. Images in each class were aligned in a reference-free manner and the class averages were refined by a maximum-likelihood approach (Sigworth et al. (1998) *J. Struct. Biol.* 122:328-339; Scheres et al. (2005) *J. Mol. Biol.* 348:139-149). These class averages were used to perform angular reconstitution to yield an initial model. The initial model was further refined by the projection-matching algorithm with C3 symmetry imposed. The angular increment was progressively decreased from 10° to 1° in the refinement. For the last round of refinement, the new classes of images were re-aligned by a maximum-likelihood approach (Sigworth et al. (1998) *J. Struct. Biol.* 122:328-339; Scheres et al. (2005) *J. Mol. Biol.* 348:139-149). The final reconstruction at ~10.8 Å, measured by FSC-0.5 cutoff, was not corrected for its temperature factor.

A total of 582,914 single-particle images (with dimensions of 320×320 pixels and a pixel size of 0.747 Å) selected from the closer-to-focus micrographs (3347 in total) were used for higher resolution reconstruction. The defocus ranged from 350 to 2000 nm. The quality of these particle images was evaluated and verified comprehensively by unsupervised classification using multivariate data analysis and K-means clustering as previously described (Shaikh, et al. (2008). *J. Struct. Biol.* 164:41). Each single-particle image was decimated by 4 times to a dimension of 80×80 pixels, was CTF-corrected by the phase flipping method, and was low-pass filtered at 12 Å prior to particle verification and initial alignment. The initial alignment for projection Euler angles and in-plane shift was generated by a projection-matching algorithm using the previously determined 10.8-Å map described above as a reference (EMDB accession code: EMD-5418). The particles images were grouped into 57 defocus groups, with a defocus width of 20 nm in each group prior to model refinement. The refinement progressed from 4-fold decimated images, to 2-fold decimated images, and finally to non-decimated images. For the refinement with non-decimated images, the particle images were re-windowed and the dimensions reduced to 256×256 pixels without changing the pixel size (0.747 Å) in order to speed up the calculations. C3 symmetry was imposed in the refinement only with non-decimated images. The back-projection reconstruction at each iteration of the refinement was CTF-corrected by Wiener filtering (Penczek. P. A. (2010) *Meth. Enzymol.* 482:35 and Frank, J. *Three-dimensional electron microscopy of macromolecular assemblies: visualization of biological molecules in their native state.* (Oxford Univ. Press, 2006). The angular increment was progressively decreased from 10° to 0.5° in the refinement. The above image analysis was implemented in customized computational procedures and workflows, combining the functions of SPDER, XMIPP and custom-made FORTRAN programs (Shaikh et al. (2008) *Nat. Protoc.* 3:1941-1974; Scheres et al. (2008) *Nat. Protoc.* 3:977-990). The final map was deconvoluted and amplitude-corrected by a B-factor of 250 Å$^2$ and was low-pass filtered at 5.6 Å with a cosine edge of an 8-Fourier-pixel width (Rosenthal & Henderson (2003) *J. Mol. Biol.* 333:721 and Fernandez, et al. (2008). *J. Struct. Biol.* 164:170). The resolution of the refined cryo-EM map, measured by FSC-0.5 cutoff, is 6 Å without masking the background noise in the map and is 5.66 Å with masking the background noise (Liao & Frank (2010) *Structure* 18:768).

E. Structure Analysis

Segmentation of the cryo-EM density was done in UCSF Chimera (Pettersen et al. (2004) *J. Comput. Chem.* 25:1605-1612). Flexible fitting of the crystal structure was performed by manual adjustment in O (Jones, T. A. (2004) *Acta Crystallog. D* 60:2115) and Coot (Emsley, et al. (2010) *Acta Crystallog. D* 66:486) and simulated annealing and energetic optimization in CNS (Brunger, A. T. (2007) *Nat. Protoc.* 2:2728) and Modeller (Marti-Renom, et al. (2000) *Annu. Rev. Biophys. Biomol. Struct.* 29:291). Analysis of CD4BS antibody interaction with the Env trimer was done by the structure fitting and alignment features in Coot and UCSF Chimera. Graphics were done in PyMOL (Schrodinger) and UCSF Chimera.

F. Backbone Model Building

A reference model, obtained by filtering the ~6-Å reconstruction to 8-Å, was used to align a larger dataset of about 1-million single-particle images by projection matching. Tens of iterations of angular refinement yielded a reconstruction with an estimated resolution of ~4 Å by Fourier Shell Correlation 0.5-cutoff. The density map allowed an initial Cα model to be traced manually in the program O (Jones, T. A. (2004) *Acta Crystallogr. D* 60:2115-2125). Interpretation of the Cα model was initially assisted by comparisons with crystal structures of the CD4-bound HIV-1 gp120 core, primary sequence information, secondary structure predictions by I-TASSER (Roy et al. (2010) *Nat. Protoc.* 5:725-738) and PHYRE (Kelley & Sternberg (2009) *Nat. Protoc.* 4:363-371), and known patterns of Env variation, glycosylation and disulfide bond formation. Improvement and validation of the ~4-Å reconstruction, transformation of the Cα model into a full atomic model, and refinement of the atomic model is in progress.

Example 2: HIV-1 Membrane Envelope Glycoprotein Trimer Structure Determination

Figure 2:
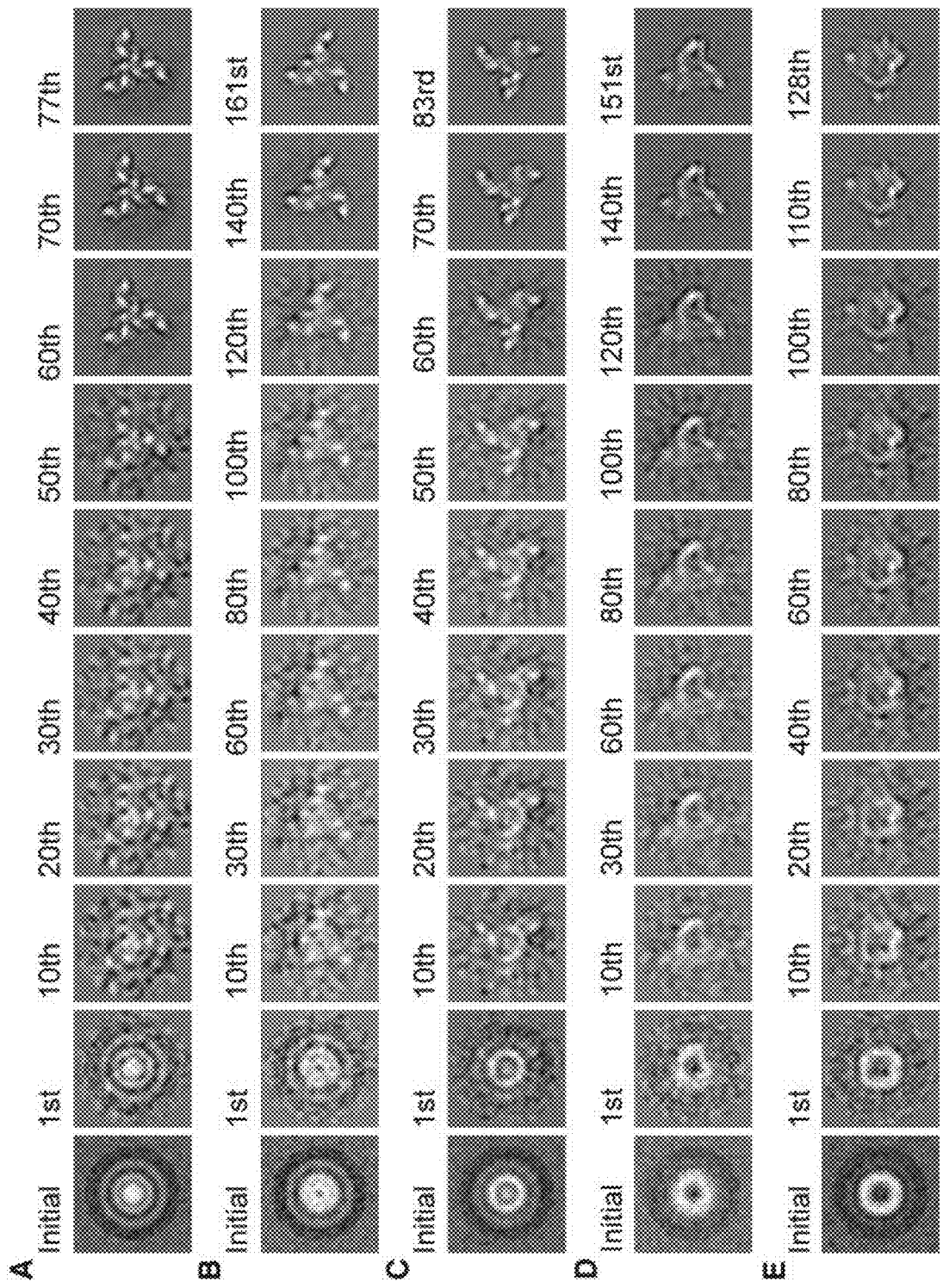
FIGS. 2A-2E show the reference-free maximum-likelihood (ML) 2D refinement of class averages. (A-E) Five typical cases are shown of reference-free ML 2D refinement of projection averages, each of which displays a different view of the Env trimer. Each row shows a sequence of average images from the same projection class, progressing from the initial average to the converged average. The ML 2D refinements started without any external or prior reference images and did not assume any symmetry. The first (leftmost) image is an average of a randomly selected subset of the raw single-particle images in the same class without any alignment against in-plane rotation and x/y shift. This un-aligned average was then used as an initial template for subsequent iterative ML optimization calculations to search for the best alignment parameters (in-plane rotational angle and x/y shift) of the single-particle images. The last (rightmost) image is the class average of the converged iteration where the alignment parameters show no further improvement over those in the previous refinement cycle. Therefore, the last class average in each row demonstrates the greatest contrast of the projection structure. The images in between show the gradual improvement of both the image contrast and the clarity of structural features, with the corresponding number of iterations indicated above each image. These ML-refined 2D class averages were used to perform angular reconstitution of the 3D structure. The numbers of single-particle images in the projection classes of A, B, C, D and E are 4420, 3164, 3556, 2171 and 2529, respectively.
Figure 3:
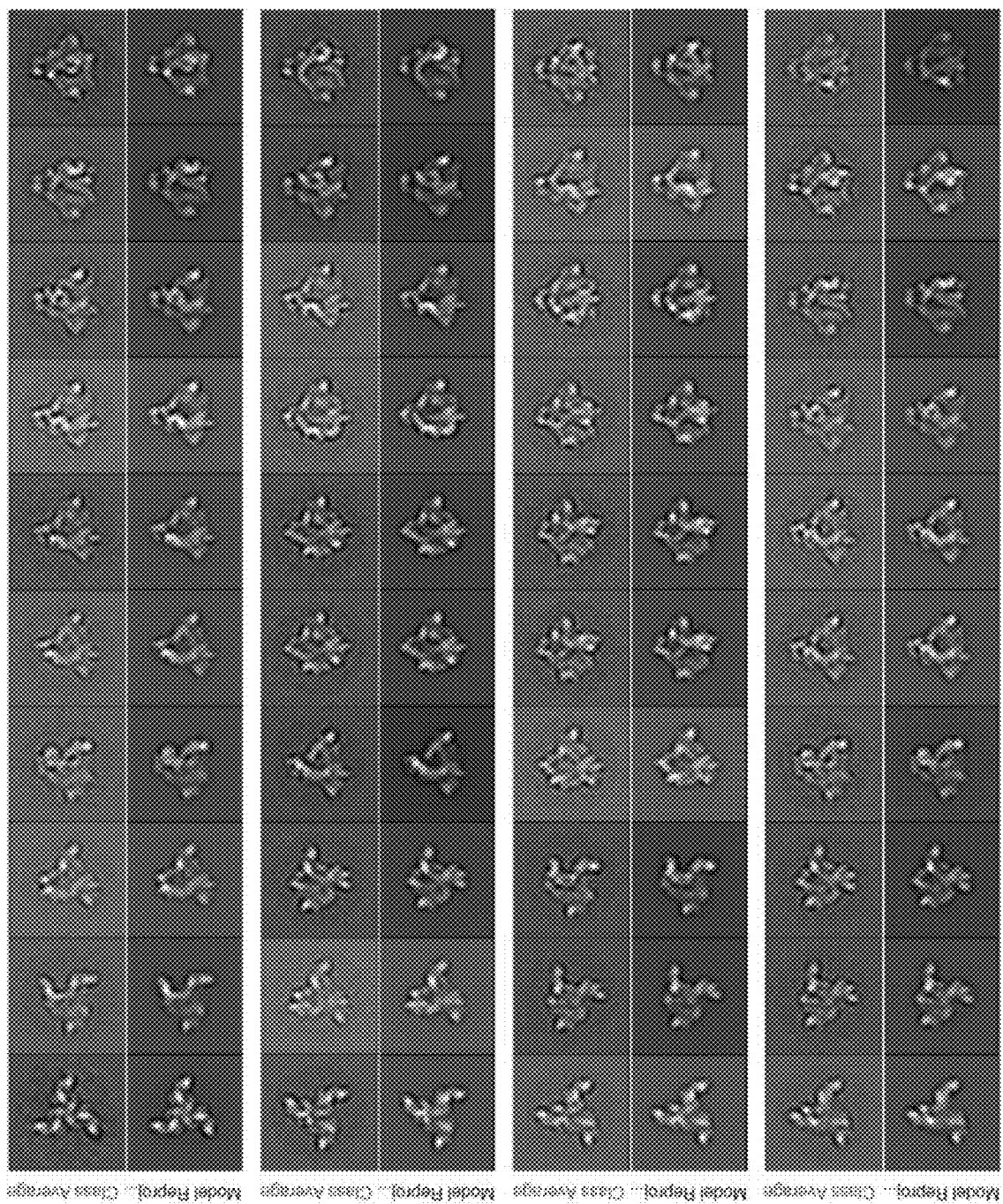
FIG. 3 shows the comparison of the class averages refined by a maximum-likelihood (ML) approach and the re-projection of the reconstructed 3D model. The ML-aligned 2D class averages are shown in the $1^{st}$, $3^{rd}$, $5^{th}$ and $7^{th}$ rows. The corresponding model re-projections are shown in the $2^{nd}$, $4^{th}$, $6^{th}$, and $8^{th}$ rows. The good agreement of the class averages and the model re-projections supports the validity of the 3D reconstruction.
Figure 4:
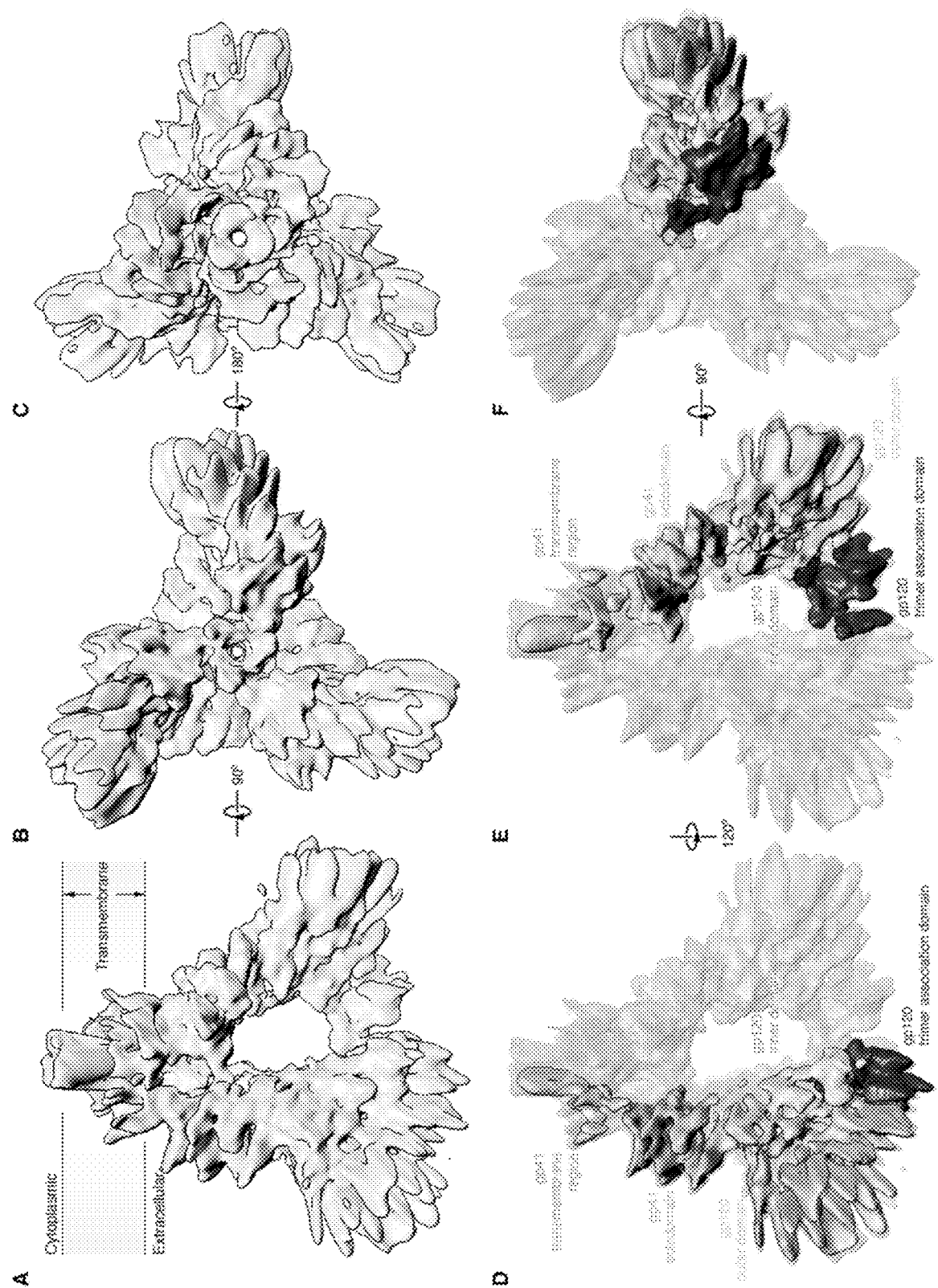
FIGS. 4A-4F show the architecture of the HIV-1 Env trimer. (A) The cryo-EM map of the HIV-1$_{JR-FL}$ Env trimer in a surface representation, viewed from a perspective parallel to the viral membrane. (B) The cryo-EM map of the HIV-1$_{JR-FL}$ Env trimer, viewed from the perspective of the target cell. (C) The cryo-EM map of the HIV-1$_{JR-FL}$ Env trimer, viewed from the perspective of the virus. (D-F) The domain organization of the Env protomer. In (D) and (E), two views from a perspective parallel to the viral membrane are shown. In (F), the view is from the perspective of the target cell.
Figure 5:
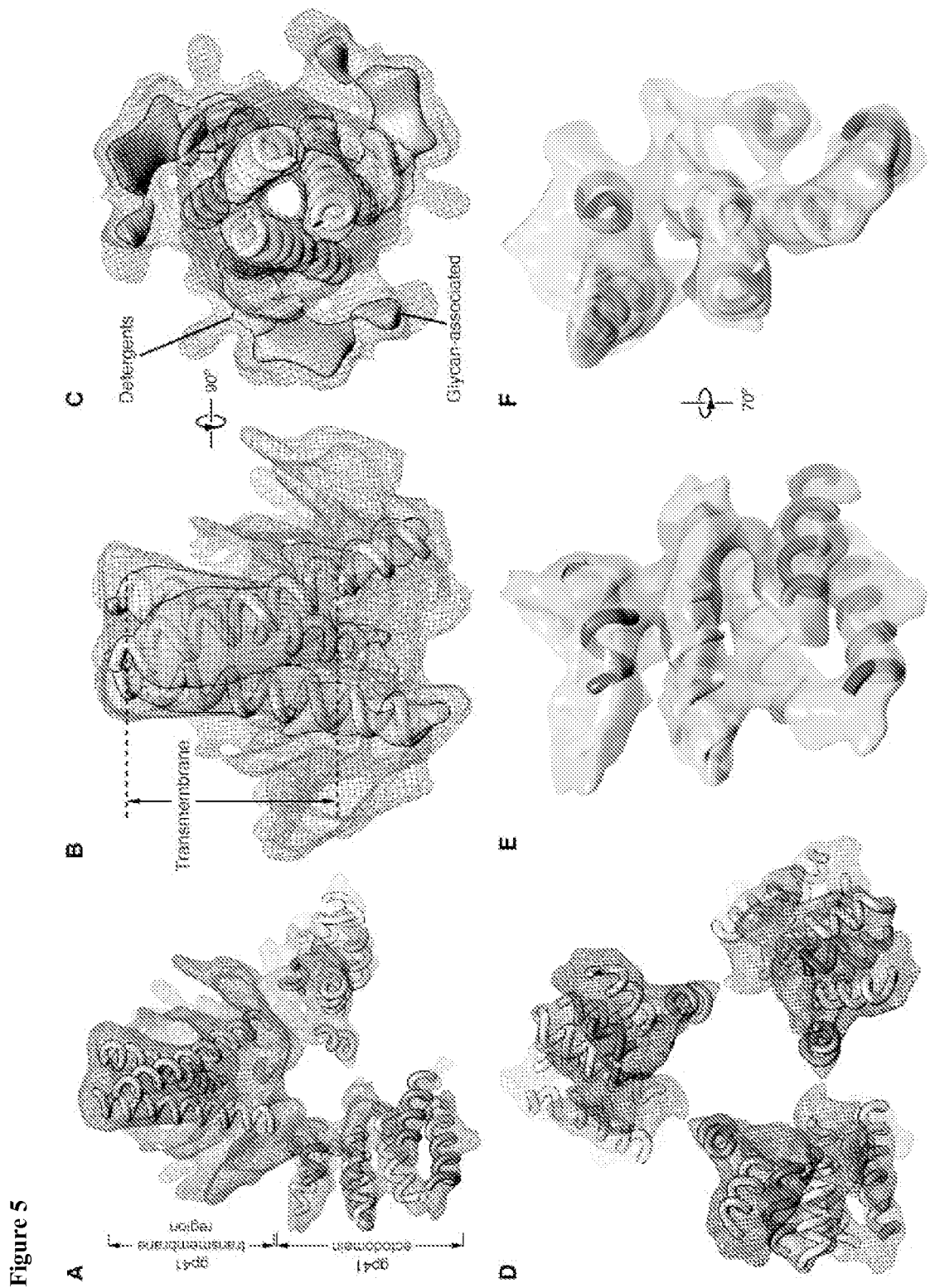
FIGS. 5A-5F show the gp41 trimer structure. (A) The cryo-EM map of the three gp41 subunits in the Env trimer, viewed from an angle of ~30° with respect to the viral membrane. (B) The gp41 transmembrane region viewed from a perspective parallel to the viral membrane. (C) The segmentation of the gp41 transmembrane region, viewed from the perspective of the virus. (D) The gp41 ectodomain viewed from the perspective of the virus. (E and F) Two views of the ectodomain of a single gp41 subunit, from perspectives parallel to the viral membrane. The potential $\alpha$-helical elements are schematically illustrated and are not intended to represent definitive backbone traces.
Figure 10:
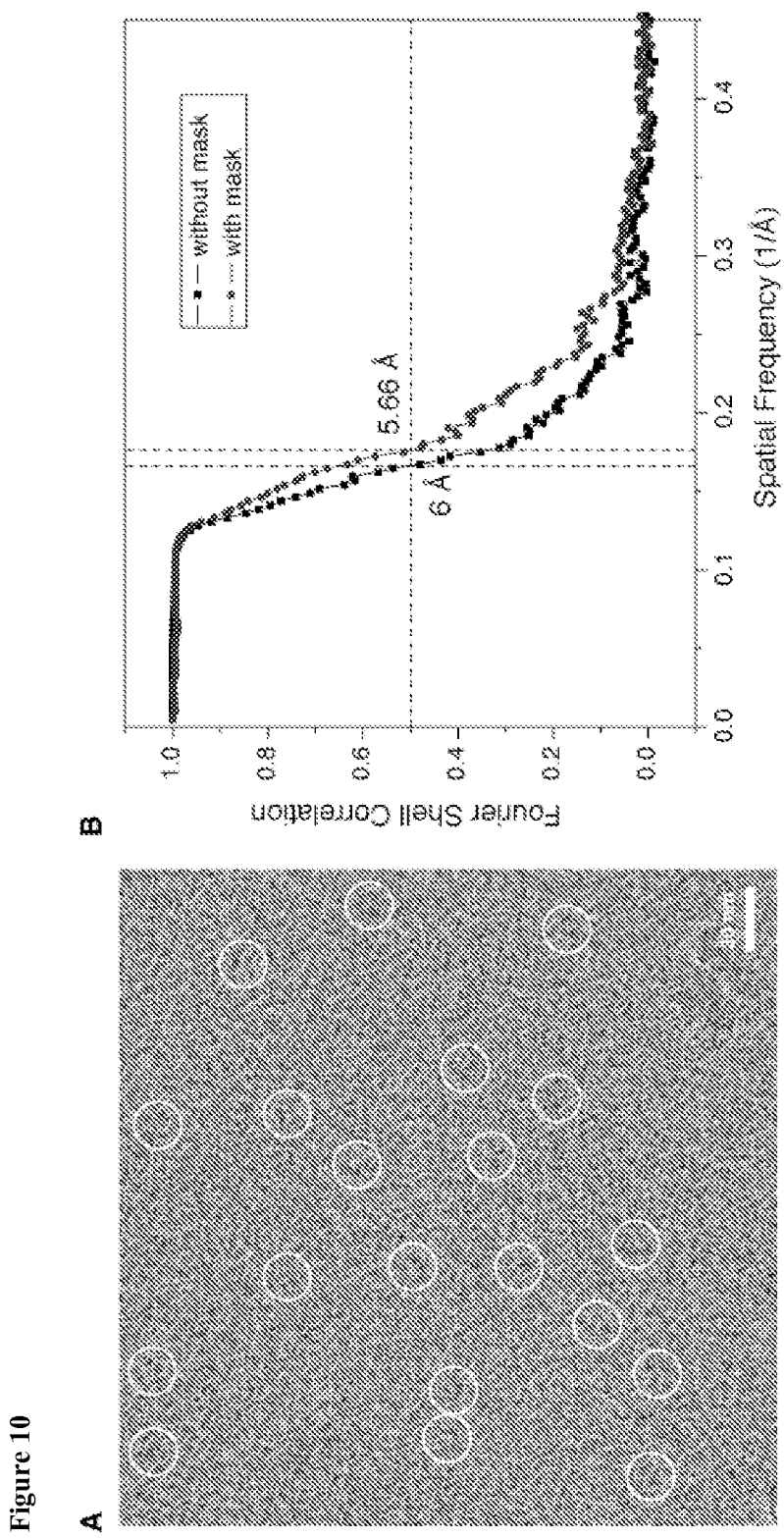
FIGS. 10A-10B show the cryo-EM imaging and resolution assessment. (A) A typical 4 k-by-4 k micrograph of the purified HIV-1$_{JR-FL}$ Env(-)ΔCT trimers protected by the Cymal-6 detergent and embedded in a vitreous ice film. The micrograph shown is low-pass filtered at 1.0 nm. A number of candidate single-particle projections of the Env trimer are highlighted by white circles. Defocus of the micrograph is ~2 μm. Scale bar, 30 nm. (B) Resolution measurement of the cryo-EM structure of the HIV-1JR-FL Env(-)ΔCT trimer, using the Fourier shell correlation (FSC) approach and the FSC-0.5 criterion. The FSC was calculated between two separate reconstructions, each generated from a randomly divided half of the entire dataset. The black curve represents the FSC calculated without masking the background noise in the 3D reconstruction. The red curve represents the FSC calculated with masking the background noise in the 3D reconstruction, which has been suggested to provide a more authentic estimation of the resolution.
Figure 11:
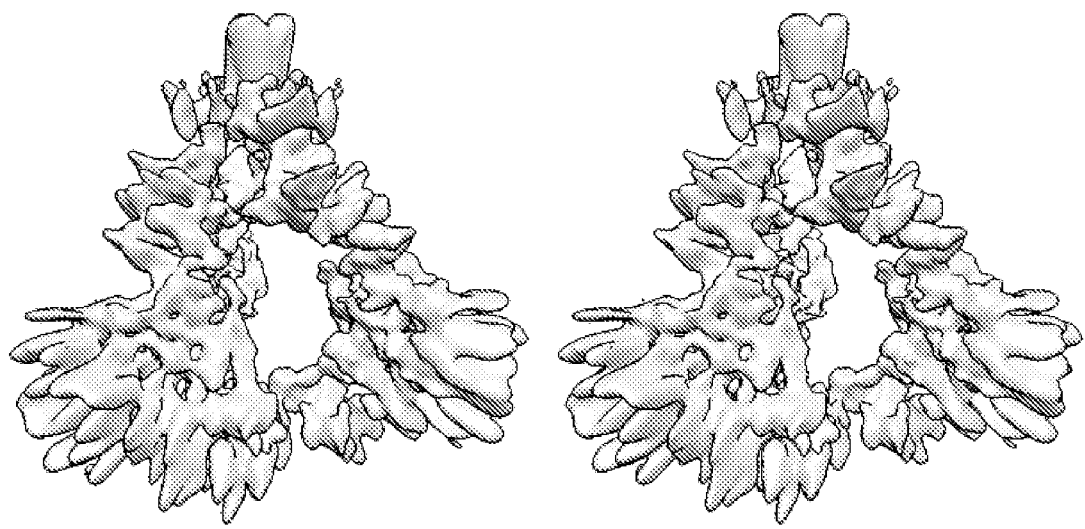
FIGS. 11A-11B show stereo views of the overall cryo-EM structure of the HIV-1$_{JR-FL}$ Env trimer. (A) The stereo view of the cryo-EM map in an isosurface representation, viewed from a perspective parallel to the viral membrane. (B) The stereo view of the same isosurface, viewed from the perspective of the target cell.
Figure 11:
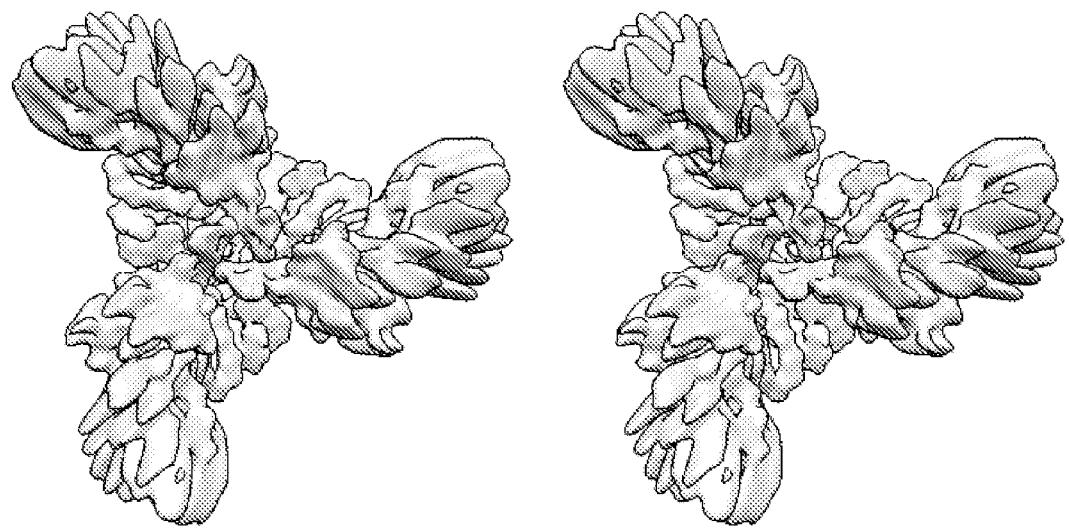
Figure 17:
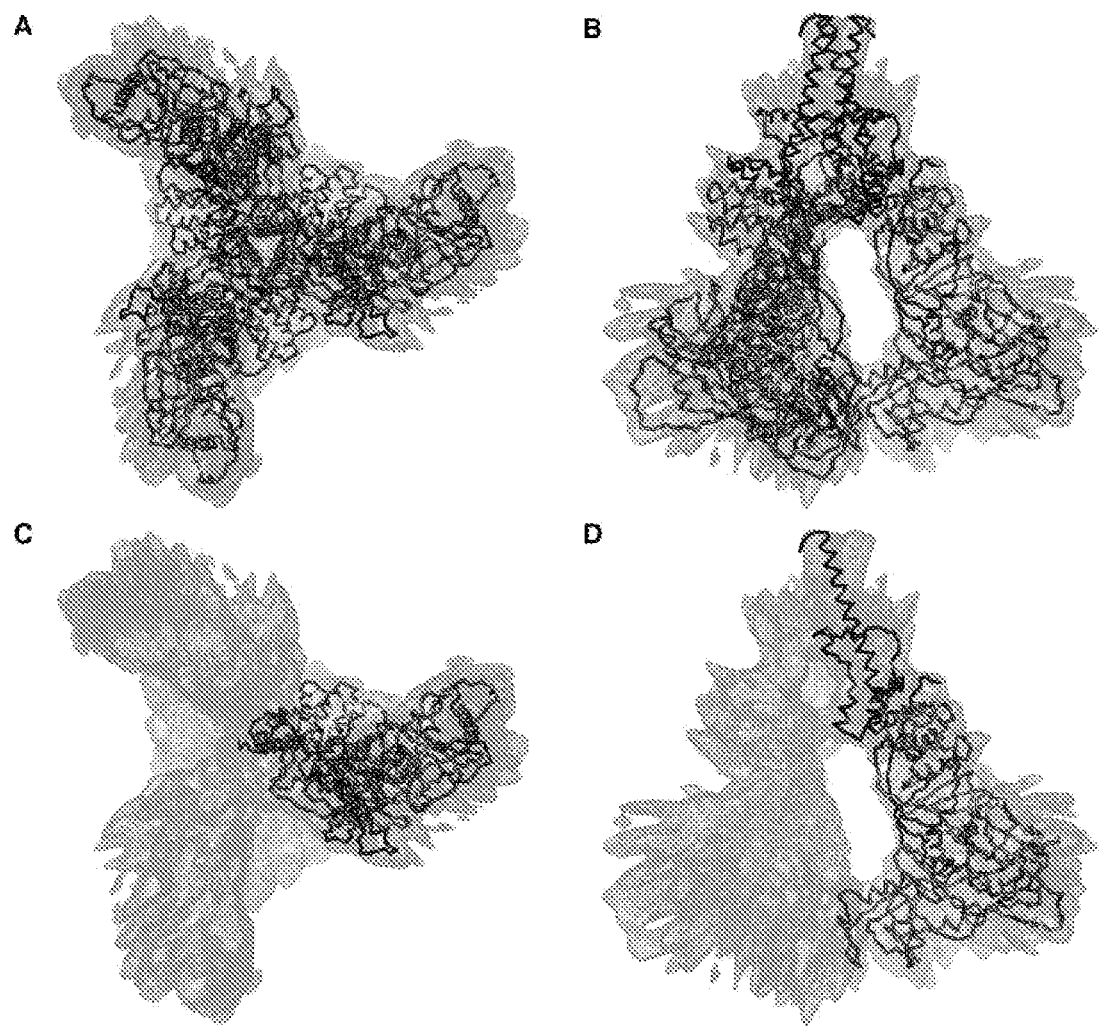
FIGS. 17A-17D show the draft Calpha trace of the unliganded HIV-1JR-FL Env trimer. The Calpha trace is shown as a backbone worm. All three protomers are shown in (A) and (B), and one protomer is shown in (C) and (D). In (A) and (C), the Env trimer is viewed from the perspective of the target cell. In (B) and (D), the trimer is viewed from a perspective parallel to the viral membrane. The density map is shown as a mesh.

The Env glycoprotein derived from a primary, neutralization-resistant (Tier 2) clade B isolate, HIV-1$_{JR-FL}$, was chosen for structural analysis. The gp120-gp41 proteolytic cleavage site in the HIV-1$_{JR-FL}$ Env was eliminated by two single-residue changes (R508S and R511S in standard HXB2 numbering). To improve the expression level on the cell surface, the gp41 cytoplasmic tail was truncated starting from Tyr712. The modified Env, designated Env(−)ΔCT, thus contains the complete ectodomain and transmembrane regions, and was purified from the plasma membrane of Env-expressing cells after solubilization in Cymal-5 detergent (see Example 1). This procedure ensured that the purified Env(−)ΔCT trimers derived from membrane-bound Env complexes that are glycosylated and have passed the quality-control checkpoints of the secretory pathway (Moulard & Decroly (2000) *Biochim. Biophys. Acta* 1469:121-132; Wyatt and Sodroski (1998) *Science* 280:1884-1888). Importantly, HIV-1 Env(−)ΔCT complexes purified in this manner retain epitopes that are dependent upon conformation, glycosylation and quaternary structure (FIG. 10). The detergent Cymal-5 was exchanged to Cymal-6 before preparation for cryo-EM imaging. The membrane glycoprotein, under the protection of Cymal-6, was flash-frozen on holey carbon film-coated EM grids and cryo-EM image data were collected at liquid nitrogen temperature. The imaging quality was found to be critically affected by the choice of the detergent and its concentration in the vitrified cryo-EM samples. A dataset of 90,306 single-particle images was assembled and subjected to multivariate data analysis, maximum-likelihood alignment and classification (Frank, J. *Three-dimensional electron microscopy of macromolecular assemblies: visualization of biological molecules in their native state*. (Oxford Univ. Press, 2006); Sigworth (1998) *J. Struct. Biol.* 122:328-229; Scheres, et al. (2005) *J. Mol. Biol.* 348:139-149). An initial model was generated by angular reconstitution from two-dimensional class averages refined by a maximum-likelihood approach (Sigworth et al. (1998) *J. Struct. Biol.* 122:328-339; Scheres et al. (2005) *J. Mol. Biol.* 348:139-149). The model was then further refined by a projection-matching algorithm to a final resolution of 10.8 Å, measured by Fourier shell correlation (FSC) with a 0.5-cutoff criterion (Liao & Frank (2010) *Structure* 18:768-775; FIGS. 1-3). Using the 10.8-Angstrom model as a reference, by analyzing a large dataset of 582,914 individual Env trimer images (equivalent to 1,748,742 protomers), a cryo-EM map was obtained that was estimated to be at ~6-Å resolution based on the 0.5-cutoff of Fourier shell correlation (FIGS. 4, 10 and 11). A cryo-EM map at ~4-Å resolution was reconstructed from a larger dataset of nearly a million images. The cryo-EM maps allowed the construction of a Ca model for the fully glycosylated Env complex (FIG. 17).

Example 3: Overview of Env Molecular Architecture

The HIV-1$_{JR-FL}$ Env(−)ΔCT complex resembles a triangular pyramid, with the transmembrane helices at the apex (FIG. 4A). Seen from the target cell, the protomer arms of the trimer exhibit a slight counterclockwise chirality (FIG. 4B). The gp120 and gp41 subunits and their intersubunit interfaces were discernable and approximately defined by segmentation analysis (FIGS. 4D-4F). The gp120 subunit demonstrates three domains, i.e., the outer domain, inner domain and trimer association domain. The gp41 subunit is composed of the ectodomain, with its helical bundles, and the transmembrane region, which includes a long membrane-spanning helix. The gp120 inner domain and the membrane-distal end of the gp41 ectodomain mediate the gp120-gp41 interactions within each protomer. The interprotomer interactions that potentially stabilize the unliganded Env trimer are limited to three regions: (1) the gp41 transmembrane region is involved in a trimeric interface within the viral membrane; (2) the gp41 ectodomain forms dimeric contacts between adjacent protomers, creating a torus-like topology; and (3) the gp120 trimer association domain mediates interactions among the gp120 subunits at the membrane-distal end of the trimer. Remarkably, this arrangement of inter-protomer contacts leaves a large empty space surrounding most of the trimer axis.

Example 4: The Transmembrane Region

Figure 12:
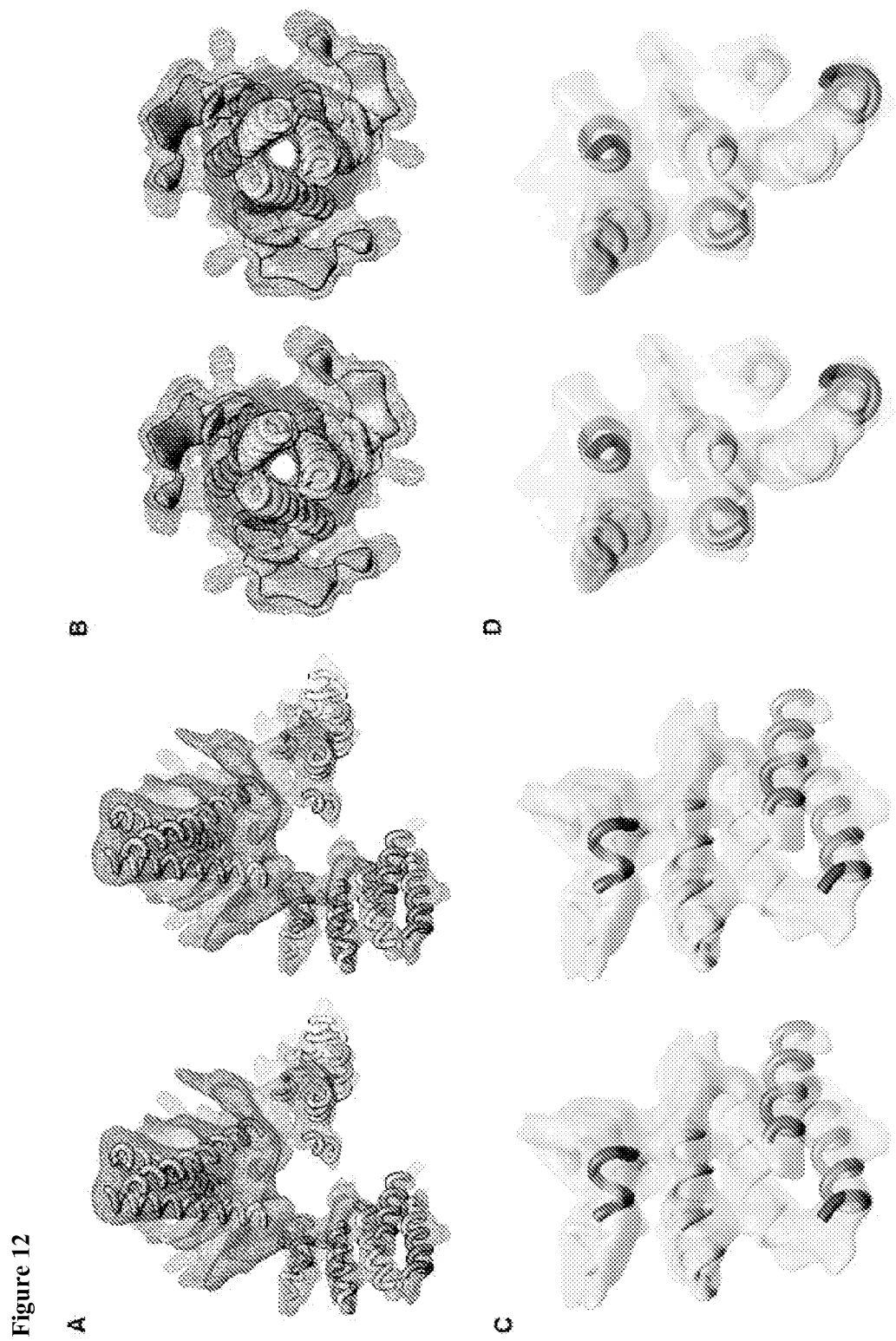
FIGS. 12A-12D show stereo views of the gp41 structure. (A) The stereo view of the density associated with the three gp41 subunits in the Env trimer, viewed from an angle of 30° with respect to the viral membrane. (B) The stereo view of the segmented density of the gp41 transmembrane region, viewed from the perspective of the virus. (C) The stereo view of the density associated with the gp41 ectodomain, viewed from a perspective parallel to the viral membrane. (D) The same density shown in (C), rotated about ~70° around the vertical axis.

The gp41 transmembrane region anchors the Env spike to the viral membrane and, as a pivot point for the three protomeric arms, contributes to trimer-stabilizing interactions. The membrane-spanning segment of each protomer is consistent with an α-helix. The three α-helices form a left-handed coiled coil, with a crossing angle of ~35° (FIGS. 5A-5B and FIG. 12). The chirality of the transmembrane helical bundle is compatible with that of the gp41 ectodomain core structure in the post-fusion state (Weissenhorn, et al. (1997) *Nature* 387:426; Chan, et al. (1997) *Cell* 89:263 and Buzon, V. (2010) *PLoS Pathog.* 6:e100088012).

Three layers of thin curved sheets in the cryo-EM density encircle the transmembrane helices (FIGS. 5A-5C). These densities are weaker in amplitude than the rest of the map, exhibit no features expected for proteins, and may arise from the localized aggregation of detergent molecules surrounding the hydrophobic surface of the transmembrane region (FIG. 5C).

The transmembrane α-helical coiled coil extends beyond the boundary of the viral membrane into the membrane-proximal external region (MPER). Near the surface of the viral membrane, transverse segments of structure, likely composed of short α-helices and loops emanating from and returning to the gp41 ectodomain, wedge into the transmembrane helical bundle close to the trimer axis. Some of the density in this region exhibits features typical of glycans (see below), and may represent gp41 carbohydrate chains (FIG. 5C).

The resulting structure not only stabilizes the transmembrane helical bundle, but also creates a sufficiently wide pitch and appropriate crossing angle between the three interacting α-helices so that the gp41 ectodomain can be built upon the transmembrane helices and achieve its torus-like topology (Mao, et al. (2012) *Nat. Struct. Mol. Biol.* in press).

Example 5: Ectodomain of the Gp41 Subunit

With an overall globular shape, the gp41 ectodomain from each protomer comprises at least seven major α-helical elements (FIGS. 5D-5F and FIG. 12). An eighth α-helix packed into this helical bundle is derived from the gp120 C terminus. The interprotomer interactions between the gp41 ectodomains incorporate the three membrane-proximal α-helical elements into a tri-lobed torus (FIGS. 5A and 5D). From this torus-like substructure, the four membrane-distal α-helical elements spread away from the trimer axis and compose the interface with gp120 (FIG. 5A).

The organization of secondary structure elements in the gp41 ectodomain in this unliganded and uncleaved state of Env differs dramatically from that of the six-helix bundle structure seen in the post-fusion state (Weissenhorn, et al. (1997) *Nature* 387:426; Chan, et al. (1997) *Cell* 89:263 and Buzon, V. (2010) *PLoS Pathog.* 6:e100088012). In the six-helix bundle, three heptad repeat 1 (HR1) regions (residues ~546-581) assemble into a trimeric coiled coil and three HR2 regions (residues ~628-661) form long α-helices that pack in an antiparallel fashion into the hydrophobic grooves of the coiled coil (Pancera, et al. (2010) *Proc. Natl. Acad. Sci. U.S.A.* 107:1166; Kwon, et al. (2012) *Proc. Natl. Acad. Sci. U.S.A.* 109:5663 and Weissenhorn, et al. (1997) *Nature* 387:426). In the unliganded state of Env, the long HR1 and HR2 α-helices in the six-helix bundle appear to be broken into short helices, consistent with previous studies suggesting that the trimeric coiled coil is not formed prior to CD4 engagement (Mische, et al. (2005) *Virology* 338:133 and Dimitrov, et al. (2005) *Biochemistry* 44:12471). The available evidence supports a model in which: 1) α-helical elements from the HR1 region locate at the membrane-distal end of the ectodomain and interact with the gp120 subunit; and 2) α-helical elements from the HR2 region locate around the membrane-proximal end of the ectodomain, contribute to the gp41 trimeric interactions and constitute the torus-shaped structure. Consistent with this model, mutagenesis experiments implicate the HR1 region in the noncovalent association with gp120 (Sen, et al. (2010) *Biochemistry* 49:5057) and the HR2 region in trimerization of the Env ectodomain (Helseth, et al. (1991) *J. Virol.* 65:2119).

Example 6: Conformational Change in Gp120 Upon CD4 Binding

Figure 6:
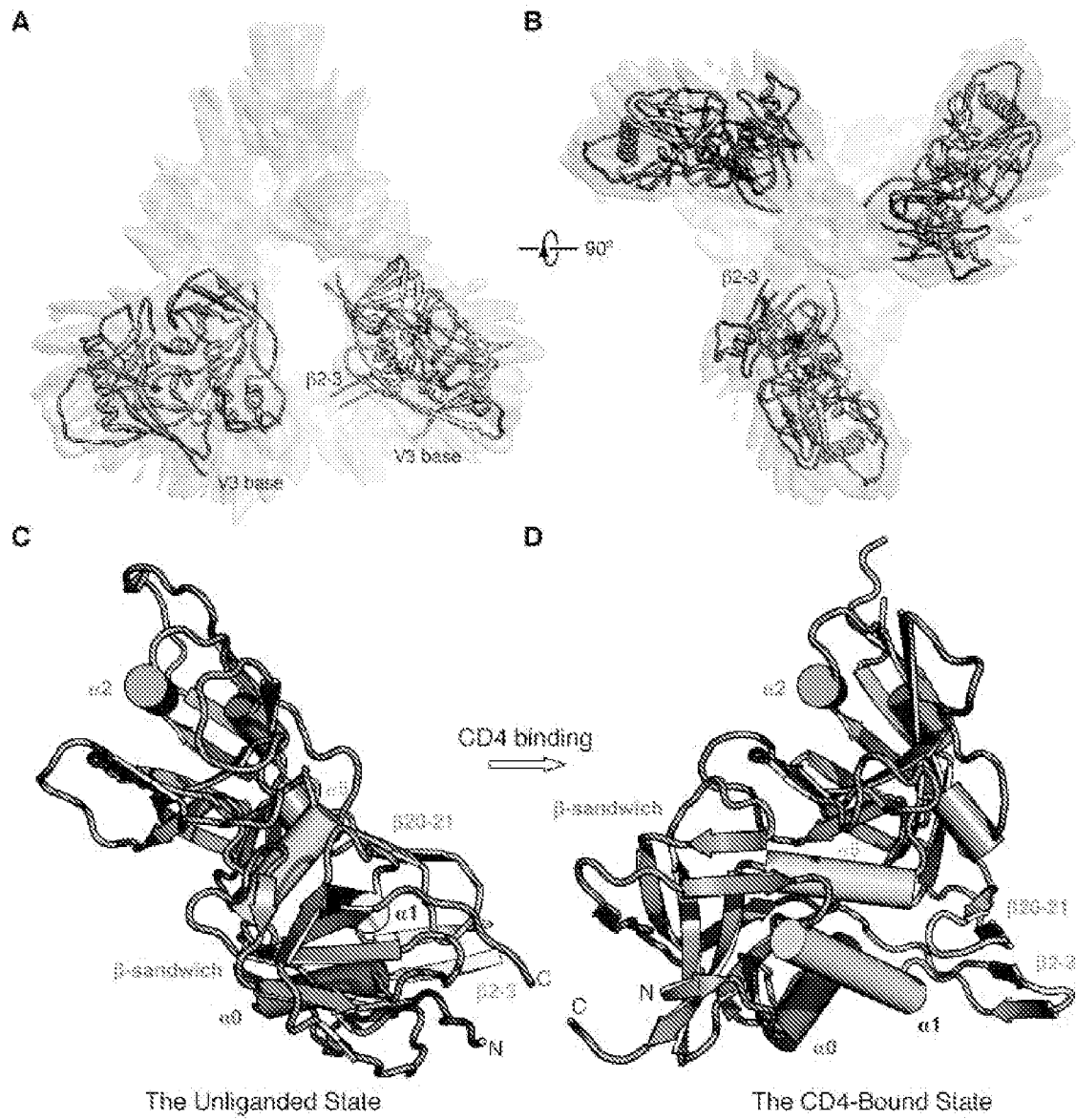
FIGS. 6A-6D show the unliganded gp120. (A) The flexible fitting of the crystal structure of the CD4-bound gp120 core into the cryo-EM map of the unliganded Env trimer, viewed from a perspective parallel to the viral membrane. (B) The flexibly fitted gp120 core structure in the unliganded Env trimer, viewed from the perspective of the virus. (C) A ribbon representation of the flexibly fitted gp120 core in the unliganded state. (D) A ribbon representation of the CD4-bound gp120 core (PDB ID: 3JWD). For comparison of the unliganded state shown in (C) and the CD4-bound state shown in (D), the gp120 outer domains are aligned to the same orientation.
Figure 7:
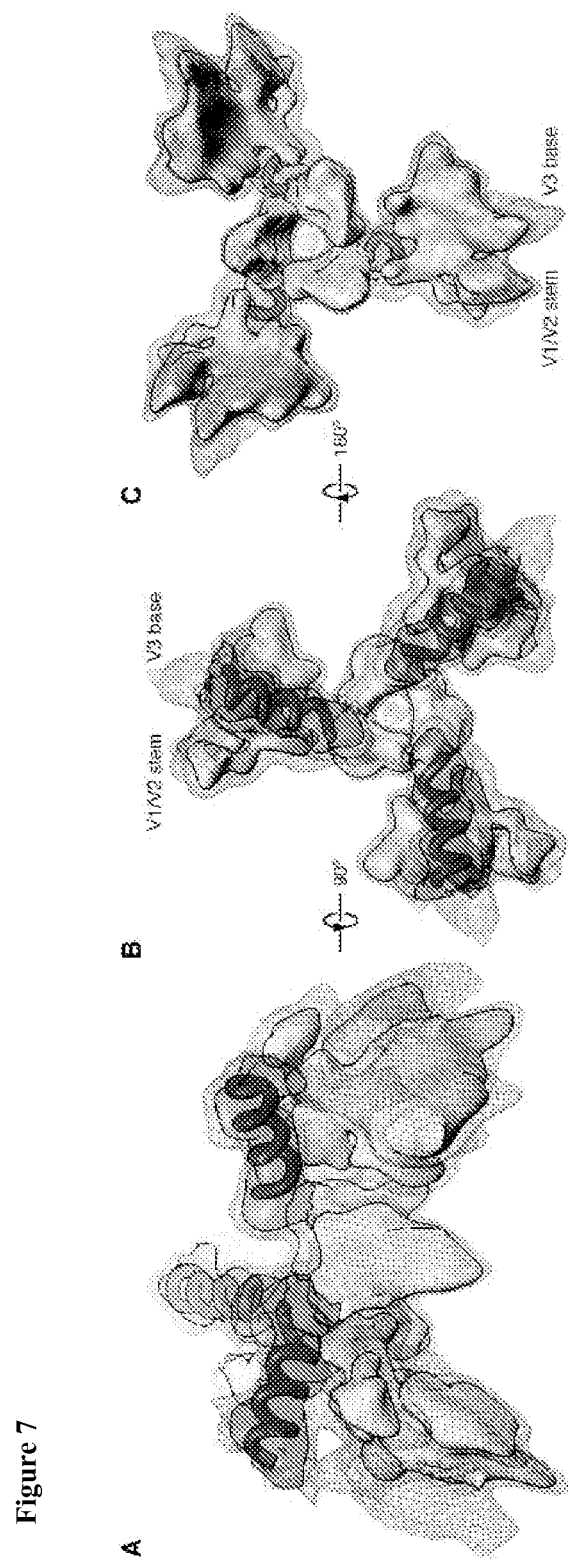
FIGS. 7A-7C show the architecture of the gp120 TAD. (A) The secondary structure elements in the gp120 TAD, viewed from a perspective parallel to the viral membrane. The TAD comprises an $\alpha$-helix, a mini-barrel structure, and a $\beta$-sheet-like element. (B) The three helical elements pointing towards the central mini-barrel structure, viewed from the center of mass of the trimer. (C) The TAD, viewed from the perspective of the target cell. The points at which the V1/V2 stem and V3 loop enter the TAD from the gp120 inner domain and outer domain, respectively, are indicated.
Figure 13:
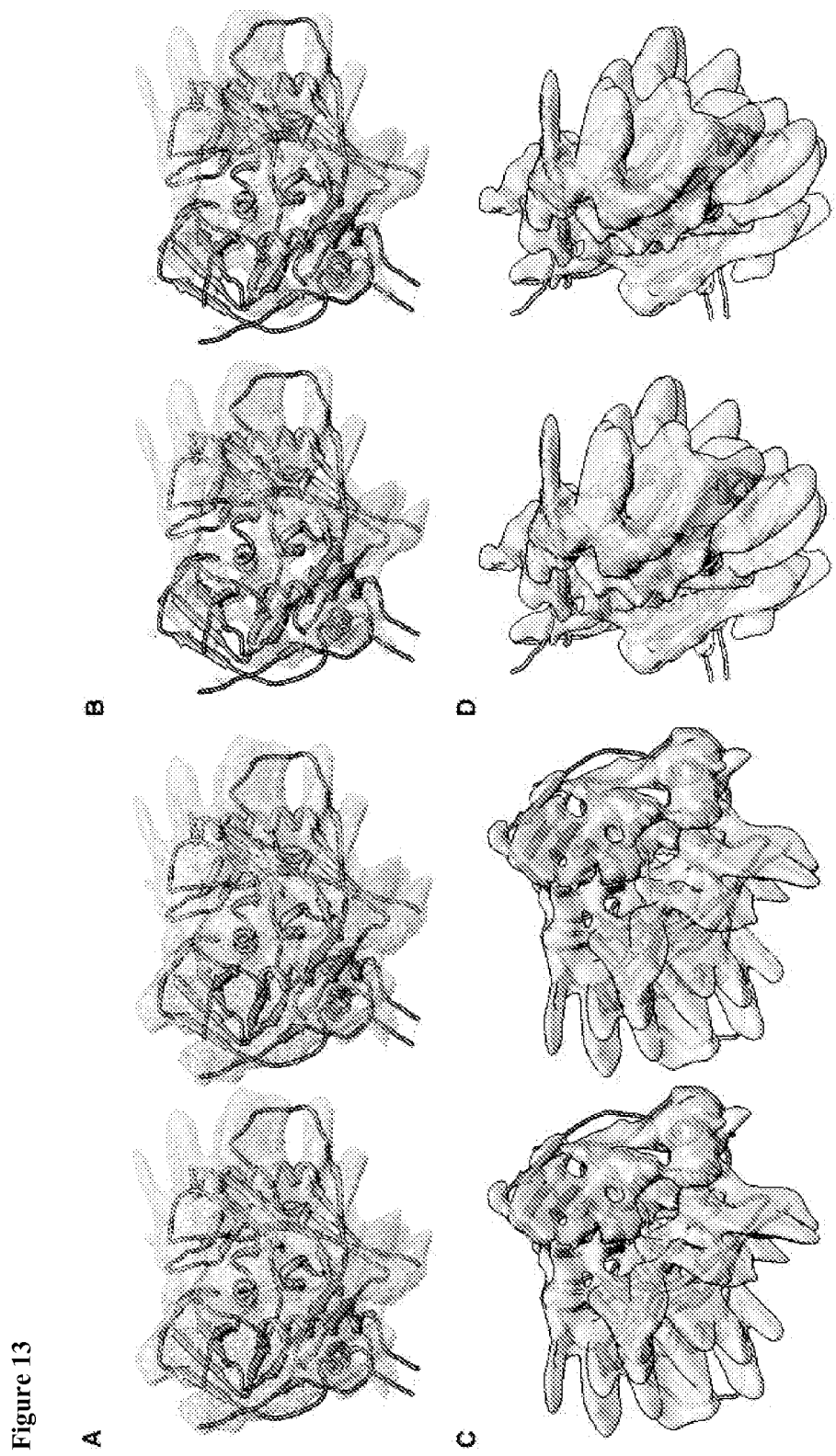
FIGS. 13A-13D show stereo views of the unliganded gp120 core structure fitted in the cryo-EM map. (A) The cryo-EM density segmentation of the gp120 core, not including the density assigned to the V1/V2/V3 regions, is shown as a meshwork that represents the isosurface at about the 3σ level. The flexibly fitted gp120 core structure is shown in ribbon representation. (B) The same view as shown in (A), but with the isosurface of the cryo-EM density set at about the 4σ level. At this higher level of contour, the densities corresponding to secondary structures are retained, whereas those corresponding to less-ordered loops tend to disappear. (C) The stereo view of the same density as in (A) fitted with the gp120 core structure, rotated ~180° around the vertical axis. (D) The viewing orientation is rotated ~100° around the vertical axis from the perspective shown in (C).
Figure 14:
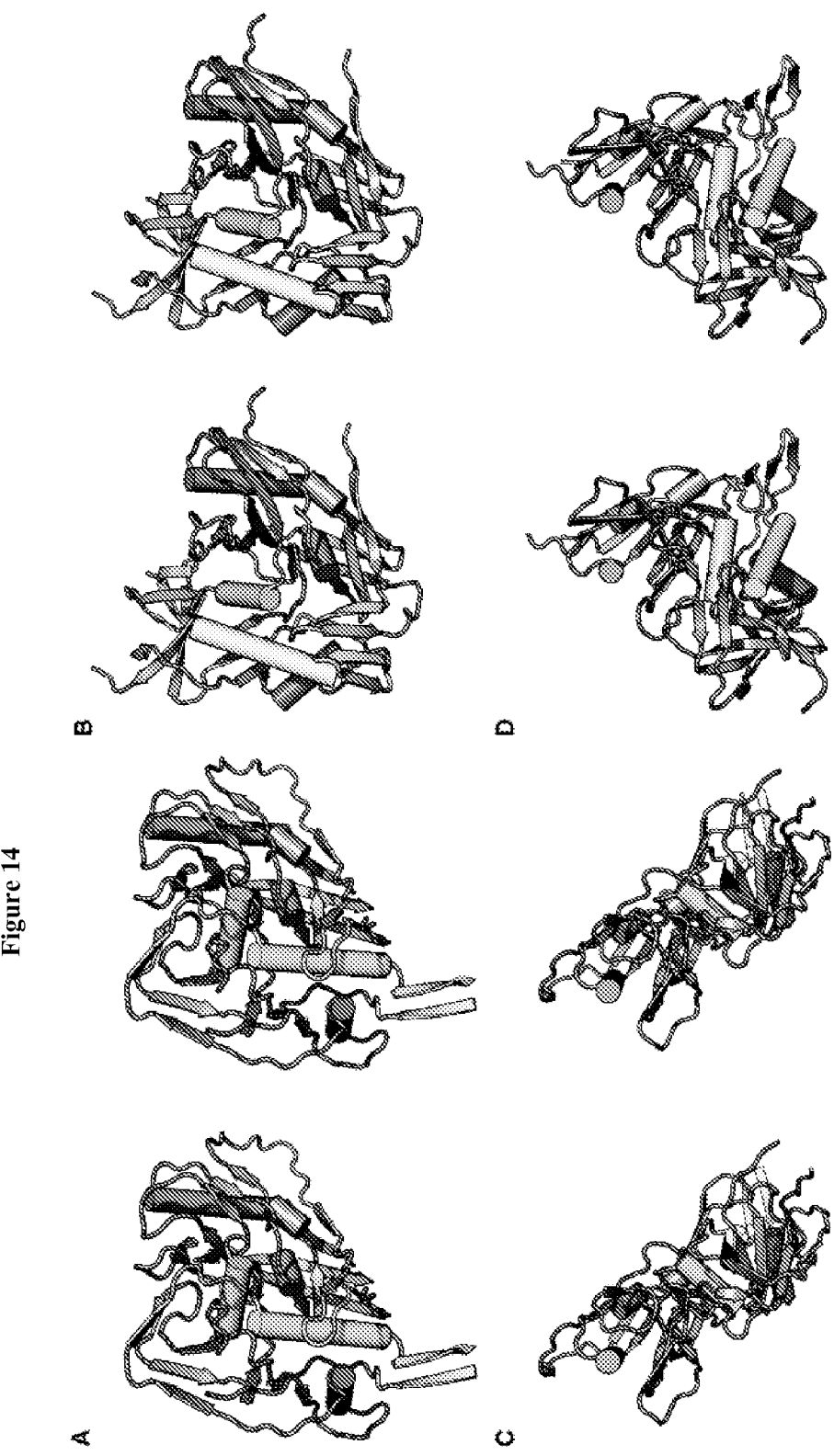
FIGS. 14A-14D show stereo views of the unliganded gp120 core structure in comparison with the CD4-bound conformation. (A and C) Stereo views of a ribbon representation of the flexibly fitted gp120 core in the unliganded state. (B and D) Stereo views of a ribbon representation of the CD4-bound gp120 core (PDB ID: 3JWD). For comparison between the unliganded state and the CD4-bound state, the gp120 outer domains (boe) are aligned to the same orientation between (A) and (B), and between (C) and (D).

The CD4-bound gp120 core consists of an inner and outer domain, as well as a bridging sheet (Kwong, et al. (1998) *Nature* 393:648; Zhou, et al. (2007) *Nature* 445:732; Pancera, et al. (2010) *Proc. Natl. Acad. Sci. U.S.A.* 107:1166 and Kwon, et al. (2012) *Proc. Natl. Acad. Sci. U.S.A.* 109:5663). The full-length unliganded gp120 subunit shown in our cryo-EM map exhibits a conformation different from that observed in the CD4-bound gp120 core (Kwong, et al. (1998) *Nature* 393:648; Zhou, et al. (2007) *Nature* 445:732; Pancera, et al. (2010) *Proc. Natl. Acad. Sci. U.S.A.* 107:1166 and Kwon, et al. (2012) *Proc. Natl. Acad. Sci. U.S.A.* 109:5663). Such a difference was already apparent in the previous 11-Å Env(−)ΔCT map (Mische, et al. (2005) *Virology* 338:133). However, the improved resolution of the current map allows positioning of the secondary structural elements in gp120 and a detailed assessment of the CD4-induced conformational change (Sattentau & Moore (1991) *J. Exp. Med.* 174:407; Myszka, et al. (2000) *Proc. Natl. Acad. Sci. U.S.A.* 97:9026; Xiang, et al. (2002) *J. Virol.* 76:9888 and Kong, et al. (2010) *J. Virol.* 84:10311). The crystal structure of the monomeric gp120 core was flexibly fitted in the CD4-bound state to the cryo-EM map. Most of the secondary structures in the CD4-bound gp120 core were able to be retained in our cryo-EM structure of the unliganded trimer. Notably, the majority of the gp120 outer domain structure fit into the cryo-EM density as a rigid-body, requiring little conformational change (FIGS. 6A-6B). By contrast, flexible fitting of the inner domain necessitated marked tertiary rearrangements in its secondary structure elements (FIGS. 6, 13 and 14). Relative to the gp120 outer domain, the β-sandwich in the gp120 inner domain is rotated by 60° in the unliganded state compared to the CD4-bound state (FIGS. 6C-6D). The α0, α1 and α5 helices are rotated approximately 110°, 40 and 60° relative to their orientations in the CD4-bound conformation, respectively. These observations are consistent with previous studies suggesting that layered movement occurs in the gp120 inner domain upon CD4 binding (Pancera, et al. (2010) *Proc. Natl. Acad. Sci. U.S.A.* 107:1166 and Finzi, et al. (2010) *Mol. Cell* 37:656).

Studies on monomeric gp120 suggested that the bridging sheet forms from two elements (β2/β3 and β20/β21) only after CD4 binding (Guttman, et al. (2012) *J. Virol.* 10.1128/JVI.07224-11 and other references). Indeed, flexible fitting of the CD4-bound gp120 core structure to the unliganded Env trimer map failed to maintain the bridging sheet in its CD4-bound conformation (Kwong, et al. (1998) *Nature* 393:648; Zhou, et al. (2007) *Nature* 445:732; Pancera, et al. (2010) *Proc. Natl. Acad. Sci. U.S.A.* 107:1166 and Kwon, et al. (2012) *Proc. Natl. Acad. Sci. U.S.A.* 109:5663; FIG. 6C). Instead, the β2/β motif, from which the gp120 V1/V2 region emanates, must extend from the inner domain towards the trimer axis to accommodate the folding of the V1/V2 and V3 regions (see Example 7). The map density associated with β20/β21 suggests that it projects from the outer domain towards the inner domain, oriented nearly orthogonally to β2/β3. Thus, both the bridging sheet and the inner domain represent dynamic elements of the gp120 subunit, undergoing significant changes in conformation in response to CD4 binding.

The conformations of the gp120 inner domain and bridging sheet, but not that of the outer domain, in the crystal structure of an unliganded simian immunodeficiency virus (SIV) gp120 core (Chen, et al. (2005) *Nature* 433:834) are incompatible with our HIV-1 Env trimer map and with the results of previous studies (Liu, et al. (2008) *Nature* 455:109; White, et al. (2010) *PLoS Pathog.* 6:e1001249; Wu, et al. (2010) *Proc. Natl. Acad. Sci. U.S.A.* 107:18844; Hu, et al. (2011) *J. Virol.* 85:2741; Mao, et al. (2012) *Nat. Struct. Mol. Biol.* in press and Guttman, et al. (2012) *J. Virol.* 10.1128/JVL.07224-11). These observations make it unlikely that the unliganded SIV gp120 core structure (Chen, et al. (2005) *Nature* 433:834) represents the actual gp120 conformation in the unliganded HIV-1 Env trimer.

Example 7: Architecture of Gp120 Trimer Association

Previous studies have suggested that the gp120 V1/V2 and V3 regions (Hu, et al. (2011) *Proc. Natl. Acad. Sci. U.S.A.* 107:18844 and Mao, et al. (2012) *Nat. Struct. Mol. Biol.* in press) are located at the membrane-distal apex of the Env spike and contribute to the association of gp120 with the trimer (Xiang, et al. (2010) *J. Virol.* 84:3147; Musich, et al. (2011) *J. Virol.* 85:2397 and Kolchinsky, et al. (2001) *J. Virol.* 75:3435). The flexible fitting of the gp120 core structure in our cryo-EM map demarcates the boundary of the gp120 trimer association domain (TAD) that comprises the V1/V2 and V3 regions (Mao, et al. (2012) *Nat. Struct. Mol. Biol.* in press). The TAD in each protomer exhibits a β-α-β architecture and extends transversely from the gp120 inner domain to the trimer axis (FIG. 7A). Occupying this span is an α-helix approximately 2 nm long stacked against a tilted β-sheet-like motif; the stem of the V1/V2 stem-loop and the V3 loop enter this β-sheet from the inner and outer gp120 domains, respectively (FIGS. 7B-7C). This transverse α-β structure supports a β-sheet-like leaf, which joins its counterparts from the other protomers to form a barrel-like structure at the trimer center (FIGS. 7B-7C). The TAD architecture and, by inference, gp120 association with the trimer apparently depend upon multiple interactions among secondary structural elements formed by the V1V2 and V3 regions.

Broadly neutralizing antibodies like PG9 and PG16 that recognize glycan-dependent TAD epitopes exhibit a strong preference for Env trimers (Walker, et al. (2009) *Science* 326:285), consistent with the complex architecture of this region. When removed from the context of the Env trimer, significant portions of the V1/V2 and V3 regions become disordered (Guttman, et al. (2012) *J. Virol.* 10.1128/JVI.07224-11) and recognition by the PG9 and PG16 antibodies is markedly diminished (Walker, et al. (2009) *Science* 326:285). By expressing the V1/V2 region fused with a heterologous scaffold protein and using an elegant strategy to select complexes with PG9, a crystal structure was obtained (McLellan, et al. (2011) *Nature* 480:336). Although we can fit the two V1/V2 β-strands in immediate contact with the PG9 antibody into the Env trimer map, the complete V1/V2 region from this crystal structure cannot be accommodated in either the 6-Å or the 11-Å trimer map (Mao, et al. (2012) *Nat. Struct. Mol. Biol.* in press). A considerable portion of the V1/V2 region remains disordered and is not resolved in the crystal structure. These regions may fold into distinct structures in the presence of other elements of the TAD, interprotomer interactions on the trimer, or contacts with the inner domain.

Example 8: Env Glycosylation

Figure 8:
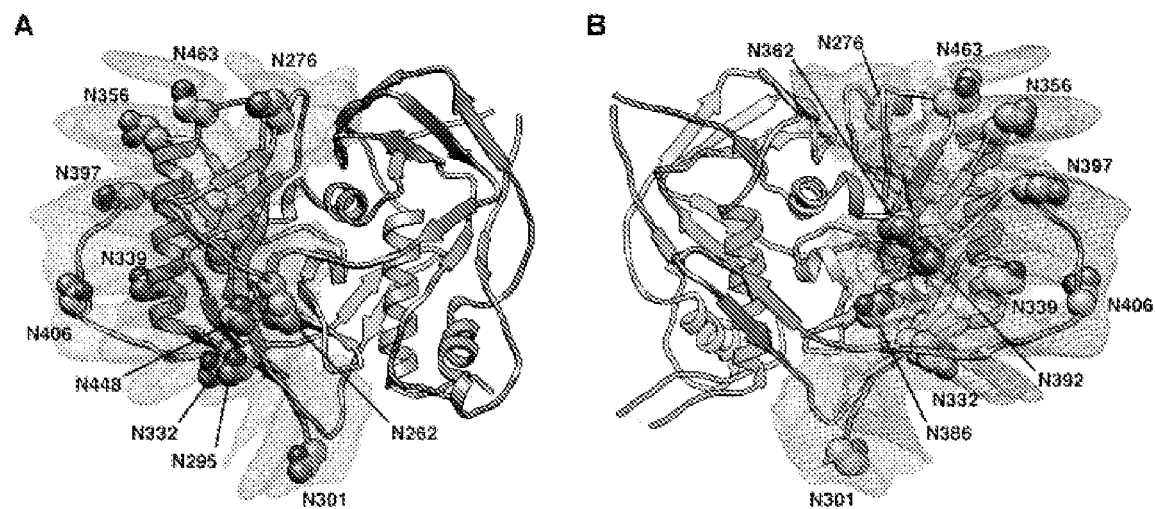
FIGS. 8A-8B show Env glycosylation. (A) The glycan-associated densities on the gp120 surface, viewed from a perspective parallel to the viral membrane. The gp120 outer domain is shown, the inner domain is shown, and the asparagine residues associated with potential N-linked glycosylation sites are labeled. (B) The glycan-associated densities on the gp120 surface. The perspective is approximately 180° from that of (A).
Figure 15:
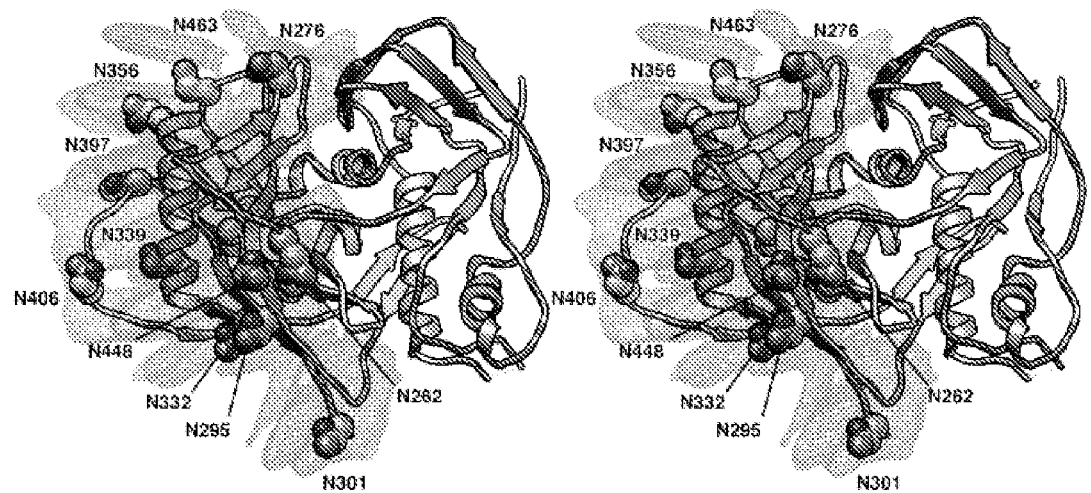
FIGS. 15A-15B show stereo views of gp120 glycan density. (A) Stereo view of the glycan-associated densities on the gp120 surface, viewed from a perspective parallel to the viral membrane. The gp120 outer domain is colored blue, the inner domain is colored orange, and the asparagine residues associated with potential N-linked glycosylation sites are labeled. (B) Stereo view of the glycan-associated densities on the gp120 surface. The perspective is approximately 1800 from that of (A).
Figure 15:
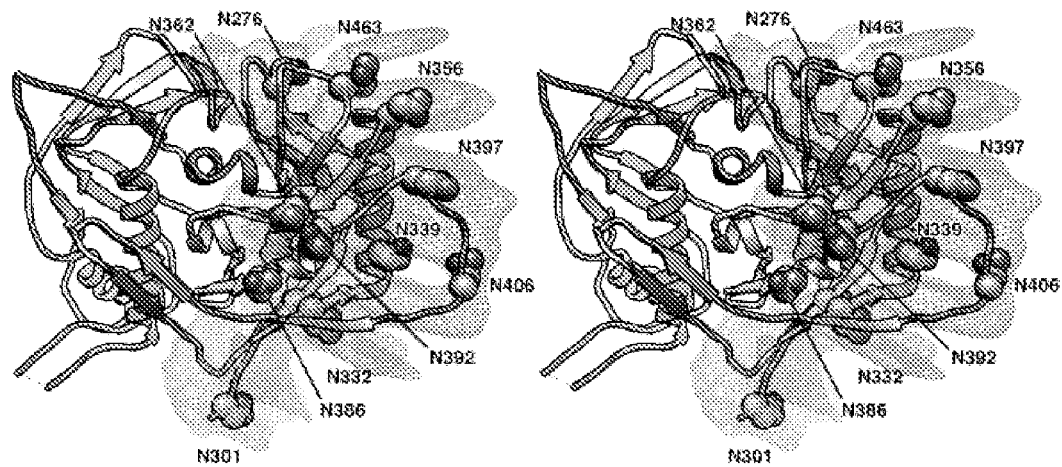
Figure 16:
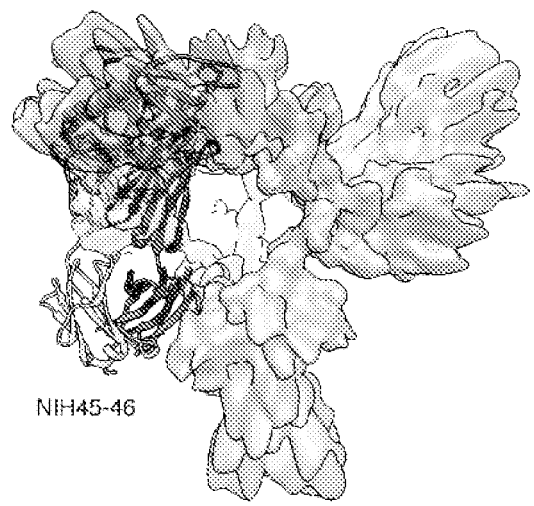
FIGS. 16A-16B show additional CD4BS antibody interactions with the Env trimer. Crystal structures of the gp120 core in complex with the CD4BS antibodies, NIH45-46 (A) and VRC-PG04 (B), were superposed on the unliganded Env trimer map as follows: the conformationally rigid gp120 outer domain was fitted to the Env trimer density map, and the outer domains in the crystal structures were aligned with the fitted outer domain (represented as a ribbon). These figures are an extension of FIG. 6 in the main paper, with the complexes viewed from the perspective shown in that figure. The PDB IDs of the antibodies in complex with gp120 core structures are 3U7Y (A) and 3SE9 (B).
Figure 16:
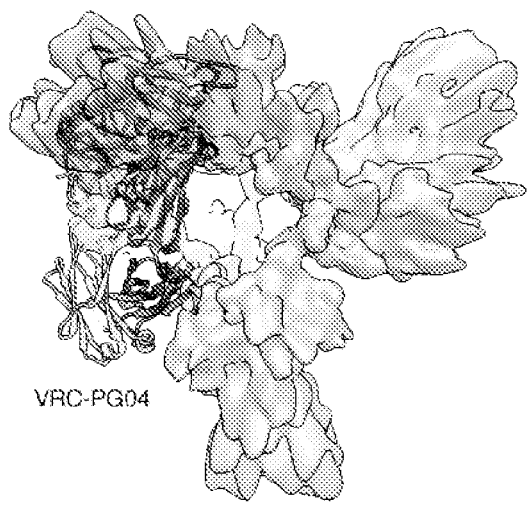

Flexible fitting of the gp120 core structure into the cryo-EM map revealed a number of outward-protruding densities on the surface of the gp120 outer domain that cannot be attributed to protein (FIGS. 6A-6B). These protuberances were found to correspond to the potential N-linked glycosylation sites (PNGS) on the protein surface (FIGS. 8 and 15). Importantly, these densities share some common features expected for less-ordered glycan structures. First, their resolution is relatively lower than that of the protein components and thus they appear featureless with blurred termini. Second, they tend to spread into flattened fan-like sheets in many cases. Third, the glycan densities are relatively stronger when the corresponding PNGS are densely packed on the protein surface. Densely packed glycans may encounter greater steric hindrance and exhibit a lower degree of freedom in sampling different conformations, thus giving rise to relatively stronger amplitude in the cryo-EM density map. Of interest, the most prominent signals ascribed to glycans arise from the gp120 outer domain and TAD. The higher degree of glycan order in these regions may contribute to the induction of broadly neutralizing antibodies directed against these glycans in some HIV-1-infected individuals (Walker, et al. (2009) *Science* 326:285 and Pejchal, et al. (2011) *Science* 334:1097).

Example 9: Role of Env Trimer Structure in Antibody Evasion

Figure 9:
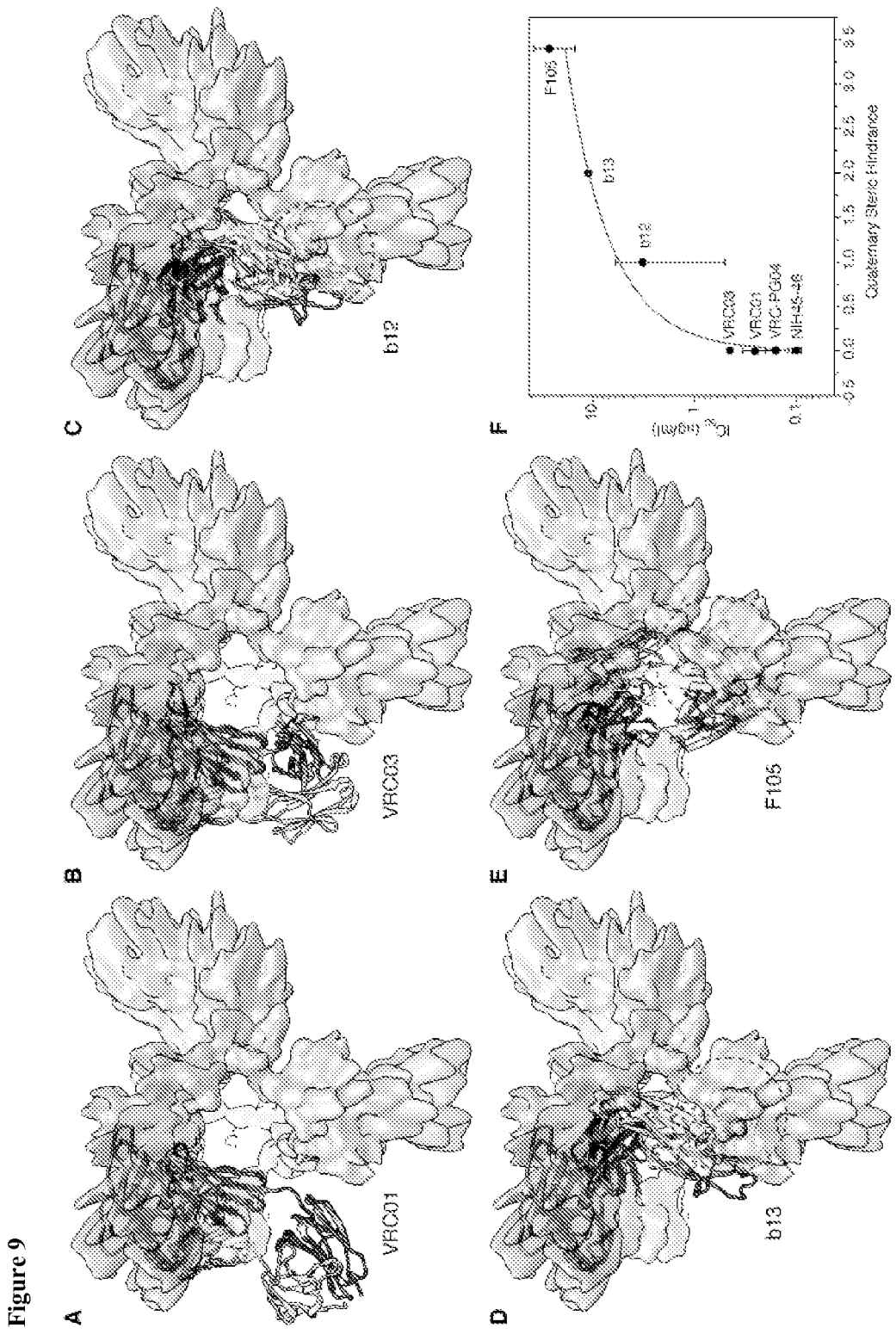
FIGS. 9A-9F show the effect of quaternary structure on virus neutralization by CD4BS antibodies. Crystal structures of the gp120 core in complex with the CD4BS antibodies, VRC01 (A), VRC03 (B), b12 (C), b13 (D), and F105 (E) were superposed on the unliganded Env trimer map as follows: the conformationally rigid gp120 outer domain was fitted to the Env trimer density map, and the outer domains in the crystal structures were aligned with the fitted outer domain. The heavy and light chains of the CD4BS antibodies are shown. The dashed circle in C-E marks the approximate diameter of the space in the neighboring gp120 subunit that is overlapped by the antibodies, highlighting the quaternary steric hindrance that the antibodies experience when approaching their binding site on the gp120 outer domain. (F) Using the volume of the quaternary clash in the case of b12 as a normalization metric, the degree of quaternary steric hindrance encountered by each antibody as it accesses the Env trimer was quantified and was plotted against the geometric mean $IC_{50}$ of the neutralization of multiple HIV-1 strains by the antibody. The PDB IDs of the antibodies in complex with gp120 core structures are 3NGB (A), 3SE8 (B), 2NY7 (C), 3IDX (D) and 3HI1 (E).

The CD4-binding site (CD4BS) antibodies are directed against the conserved gp120 surface that engages CD4, are elicited in some HIV-1-infected individuals and exhibit a range of potencies of HIV-1 neutralization (Chen, et al. (2009) *Science* 326:1123-1127). What accounts for these differences in potency? Crystal structures of several CD4BS antibodies complexed with the HIV-1 gp120 core are available (Zhou et al. (2010) *Science* 329:811-815; Chen, et al. (2009) *Science* 326:1123-1127). The overall conformation of the gp120 outer domain in the unliganded HIV-1 Env trimer does not significantly differ from that in the crystal structures of gp120 cores complexed with CD4 or CD4BS antibodies. As all CD4BS antibodies include the gp120 outer domain elements in their epitopes, we could superpose the crystal structures of the antibody-bound gp120 core onto our Env trimer structure by aligning the outer domains. This allows an assessment of the angle-of-approach taken by the CD4BS antibodies and CD4 as they initially engage the unliganded Env trimer, and reveals remarkable differences among CD4BS antibodies (FIG. 9). Potently neutralizing antibodies like VRC01, VRC03, VRC-PG04 and NIH45-46 experience nearly no quaternary steric hindrance from the neighboring Env subunit (FIGS. 9A-9E and 16). By contrast, the neighboring Env subunit creates substantial quaternary steric hindrance for the b12, b13 and F105 antibodies, suggesting that an induced conformational change in the Env trimer is necessary for these less potently neutralizing antibodies to achieve optimal binding. FIG. 9F shows that the degree of quaternary steric hindrance encountered by the CD4BS antibodies as they engage the unliganded Env trimer, using b12 binding as a normalization metric, is inversely related to HIV-1 neutralization potency. The results presented herein provide a structural explanation for experimental observations suggesting that the ability to bind the Env trimer in its unliganded state represents the major factor in determining the neutralization potency of CD4BS antibodies (Pancera & Wyatt (2005) *Virology* 330:145-159).

Example 10: Backbone Trace of the HIV-1 Env Trimer

The Calpha model of the HIV-1$_{JR-FL}$ Env(−)ΔCT trimer is shown in FIG. 17. The Calpha trace shows that the gp120 N and C termini, along with the inner domain β-sandwich, form a clasp-like structure that keeps the membrane-distal part of the gp41 ectodomain from assuming the HR1 coiled coil conformation. The TAD is shown to form a β-sheet that includes strands from the V1/V2 stem, the V3 loop and the V1 region. A glycosylated strand (residues 155-166) and the α-helix in the TAD form the epitopes for the PG9 and PG16 neutralizing antibodies. The gp120 subunits in the trimer are associated through interactions involving the β-hairpins (residues 179-194) that form a mini-β-barrel at the trimer axis. Other interactions that stabilize the trimer include those among the gp41 ectodomains in the torus-like structure, and among the membrane-spanning helices (residues 683-700).

Example 11: Implications of Env Trimer Structure for Virus Entry

Enveloped viruses employ conformational changes in their envelope proteins to mediate the fusion of viral and target cell membranes. Environmental triggers such as endocytosis/pH decrease or receptor binding drive the envelope proteins to energetically favorable, fusion-ready conformations. Influenza virus uses low pH, which globally alters the conformation of the hemagglutinin (HA) protein, as a trigger. A spring-loaded mechanism has been suggested to explain the HA conformational change that mediates virus entry (Wilson, et al. (1981) *Nature* 289:366 and Carr & Kim (1993) *Cell* 73:823). The long α-helix in the fusion-ready HA$_2$ protein is broken into several shorter pieces in the prefusion state, resembling a "loaded spring". When triggered by a pH decrease, the HA$_2$ short helices and linking loops refold into a longer helix of lower free energy. This allosteric change delivers the fusion peptide at the HA$_2$ N-terminus to the target membrane and promotes virus entry.

Instead of a decrease in pH, HIV-1 utilizes sequential binding to the CD4 and CCR5 receptors as triggers for entry-related conformational changes in Env. The unliganded Env trimer is prestressed, storing all of the energy needed for membrane fusion in its unique architecture. Spring-loading appears to be used twice in the unliganded gp41 subunit, i.e., the HR1 and HR2 helices of the post-fusion six-helix bundle are each broken into smaller helices and other structural elements in the membrane-distal gp120-gp41 interaction interface and in the membrane-proximal torus, respectively. This dual spring-loaded mechanism likely reflects the unique requirements of triggering by dual receptor engagement, so that binding to each receptor frees only one "spring" at a time. Consistent with this model, experimental observations suggest that CD4 binding induces the formation/exposure of the HR1 coiled coil, but subsequent events such as CCR5 binding are required for formation of HR2 and the six-helix bundle (Futura et al. (1998) *Nat. Struct. Biol.* 5:276-281).

Achieving a prestressed structure that implements a dual spring-loaded mechanism imposes significant challenges to folding; indeed, HIV-1 Env synthesis and assembly is relatively slow and inefficient. Once synthesized, functional Env spikes must avoid premature triggering. Synthesis and maintenance of a competent, spring-loaded Env trimer requires multiple interactions between and within the protomers. The elegant torus-like architecture of gp41 takes advantage of the high stability and pivot potential of the transmembrane three-helix bundle. Truncations of the gp41 transmembrane region to produce "soluble gp140" trimers (Binley, et al. (2000) *J. Virol.* 74:627) typically disrupt the native Env structure, as indicated by loss of PG9 and PG16 epitopes (McLellan, et al. (2011) *Nature* 480:336). Packing of the short gp41 helices and interactions with the gp120 inner domain and N/C termini likely maintain the spring-loaded conformation of the membrane-distal gp41 ectodomain. Interactions between the TAD and the gp120 inner domain layers and bridging sheet components explain the ability of the V1/V2 and V3 regions to prevent gp120 from assuming the energetically favored CD4-bound state (Kwon, et al. (2012) *Proc. Natl. Acad. Sci. U.S.A.* 109:5663). Conversely, CD4 binding necessitates TAD restructuring, thus decreasing gp120 trimerization and allowing an open conformation of the trimer (Liu, et al. (2008) *Nature* 455:109). The "spring-loaded" architecture of the HIV-1 Env is well adapted to respond to the relatively subtle perturbation of initial receptor engagement with dramatic, programmed conformational changes. Sensitive adjustment of local features allows HIV-1 variants to adapt to differing levels of receptors and to escape antibody neutralization. The ability of the HIV-1 Env to fuse membranes at neutral pH contributes to cytopathic events in infected lymphocytes and to loss of immunocompetence in the infected host (Etemad-Moghadam, et al. (2001) *J. Virol.* 75:5646). Thus, the unique architecture of Env trimer offers multiple fitness advantages to a persistent virus like HIV-1.

TABLE 1

List of predicted interactions related to gp120-gp120 association and gp120 TAD stability

| Interaction type | Residues | Structural context | Phenotypes and functions | Comments |
| --- | --- | --- | --- | --- |
| Inter-subunit hydrophobic interaction | Val 182<br>Ile 184<br>Leu 193 | V2 | On-axis trimer association of gp120 V2 mini-β-barrel | The hydrophobicity of the three residues is highly conserved in HIV-1 and HIV-2/SIV. |
| Inter-subunit salt bridge | Asp 185<br>Arg 192 | V2<br>V2 | Part of trimer association of gp120 V2. Contribute to the stabilization of the V2 mini-β-barrel. | An extensive hydrogen bond network is also formed at this gp120-gp120 interface. These residues have a moderate variation across different strain. |
| Intra-subunit hydrophobic interaction | Leu 129<br>Val 127<br>Phe 176<br>Val 181<br>Pro 183<br>Ile 194<br>Leu 179 | Pre-V1<br>loop<br>V2 | This hydrophobic patch supports the gp120 V2 mini-β-barrel. It is important for keeping V2 β-hairpin in a conformation compatible with the structure of V2 mini-β-barrel. | The core residues of this hydrophobic patch is mostly well conserved in HIV-1, and largely conserved in PIVs. |
| Intra-subunit salt bridge | Lys 121<br>Glu 172 | β2<br>αV2 | Stabilization of gp120 TAD. Contribute to increase the conformational rigidity of TAD. | Moderate variation, not well conserved. |
| Intra-subunit salt bridge | Lys 178<br>Asp197 | αV2<br>β3 | Stabilization of gp120 TAD | In most of other HIV-1 strains, position 197 is a N-glycosylation site. This implies that JR-FL might get a more table TAD than other isolates. |
| Intra-subunit hydrophobic interaction | Ile 154<br>Val 134 | V1<br>V1 | Stabilization of TAD β-sheet | Moderate variation, not well conserved. |
| Intra-subunit hydrophobic interaction | Leu 122<br>Pro 124<br>Phe 317 | βV3a<br>β2<br>β2 | V3-β2 interaction. Contribute to the stabilization of V3 insertion in V1V2 pocket. | Well conserved in PIVs. |
| Intra-subunit hydrophobic interaction | Cys 131<br>Cys 157<br>Ile 309<br>Pro 313<br>Phe159<br>Ile 161 | βV1a<br>βV1b<br>βV3b<br>βV3b<br>V2<br>V2 | V1/V2/V3 association. Very important for native TAD conformation. Mutations in some of these residues affect PG9/PG16 neutralization sensitivity. | These residues are either highly conserved or conserved with respect to hydrophobicity. |
| Intra-subunit salt bridge | Glu 153<br>Arg 305 | V1<br>V3 | Stabilization of V3 insertion in V1V2 pocket. Mutations in these residues may modulate cellular tropism, the level CD4 usage, and PG9/PG16 neutralization sensitivity. | Moderate variation. Relatively higher conservation in HIV-1 than in HIV-2/SIV. |

TABLE 1-continued

List of predicted interactions related to gp120-gp120 association and gp120 TAD stability

| Interaction type | Residues | Structural context | Phenotypes and functions | Comments |
|---|---|---|---|---|
| Intra-subunit salt bridge | Glu 150<br>Arg 315 | V1<br>V3 | Contribute to the stabilization of V3 insertion in V1V2 pocket. | Not well conserved; the similar effect can be achieved by other interactions like hydrophobic interactions. |

TABLE 2

List of predicted interactions at the gp41-gp41 interface

| Interaction type | Residues | Structural context | Phenotypes and functions | Comments |
|---|---|---|---|---|
| Salt bridge | Lys 601<br>Glu 647 | Gp41 ℒH<br>Gp41 α13 | Contribute to the torus-like topology of gp41 MPDs. | An extensive hydrogen bond network is also formed at this gp41-gp41 interface |
| Hydrophobic interaction | Leu 602<br>Ile 603<br>Ile 646<br>Leu 645<br>Ile 642 | Gp41 ℒH<br><br>Gp41 α13 | The core hydrophobic interactions that keeps the torus-like topology of gp41 MPDs. Removal of this interface results in gp120 shedding and the loss of membrane-fusion activity or infectivity. | Leu 602, Ile 603, Ile 646, Leu 645 are in direct contact; Ile 642 only contacts Ile 646 and Leu 645. |
| Hydrogen bond | Ser 599<br>Glu 641 | Gp41 ℒH<br>Gp41 α13 | Contribute to the torus-like topology of gp41 MPDs. | |
| Salt bridge | Glu 632<br>Arg 633 | Gp41 α12 | Trimer association of gp41 around the axis of threefold symmetry on the viral membrane. Important for creating the appropriate crossing angle between three α16 helices by inserting α12 in between α16 exterior portions. | A circle of salt bridges is formed |
| Hydrophobic interaction | Trp 628<br>Met 629<br>Trp 631<br>Trp 678<br>Ile 682<br>Phe 685<br>Ile 686<br>Val 689 | Gp41 α12<br><br><br>Gp41 α16 | Inter-subunit interaction between α12 and α16. These interactions create the basis for the MPD torus-like topology. | |
| Hydrophobic interaction | Val 693 | Gp41 α16 | Trimer association of gp41 TMD in viral membrane. | The closest inter-subunit hydrophobic interaction in the viral membrane |
| Hydrogen bond | Arg 696<br>Thr 700 | Gp41 α16 | Trimer association of gp41 TMD in viral membrane | Arg 700 might be necessary to support the crossing angle between three α16 helices |
| Hydrogen bond | Ser 703<br>Arg 707 | Gp41 α16 | Trimer association of gp41 TMD in viral membrane | |

TABLE 3

List of predicted interactions at the gp120-gp41 interface

| Interaction type | Residues | Structural context | Phenotypes and functions | Comments |
|---|---|---|---|---|
| Salt bridge | Glu 91<br>Arg 557 | Gp120 β1<br>Gp41 α9 | β-sandwich-MDD association | Well conserved |
| Salt bridge | Arg 503<br>Glu 654 | Gp120 α6<br>Gp41 α14 | Protection and sequestration of gp41 fusion helix | Well conserved |
| Salt bridge network | Lys 510<br>Glu 659<br>Glu 622<br>Lys 655 | Gp120 α6<br>Gp41 α14 | Protection and sequestration of gp41 fusion helix | Conserved |

TABLE 3-continued

List of predicted interactions at the gp120-gp41 interface

| Interaction type | Residues | Structural context | Phenotypes and functions | Comments |
|---|---|---|---|---|
| Salt bridge | Glu 509<br>Arg 542 | Gp120 α6<br>Gp41 α8 | Protection and sequestration of gp41 fusion helix | Well conserved |
| Hydrogen bond | Lys 502<br>Thr 538 | Gp120 α6<br>Gp41 α8 | Protection and sequestration of gp41 fusion helix | Conserved in HIV-1 clade A/B/C |
| Hydrogen bond network | Glu 87<br>Gln 577<br>Lys 574 | Gp120 β-sandwich<br>Gp41 α10 | β-sandwich-MDD association | Less conserved |
| Hydrophobic interaction | Val 42<br>Val 44<br>Ile 573<br>Leu 576 | Gp120 N-terminal loop<br>Gp41 α10 | β-sandwich-MDD association | Well conserved |
| Hydrophobic interaction | Val 489<br>Ile 491<br>Pro 493<br>Trp 45<br>Ala 48<br>Pro 81<br>Met 95<br>Phe 93<br>Leu 568<br>Val 570<br>Trp 571<br>Met 565 | Gp120 β25<br>gp120 N-terminus<br>Next to gp120 β-sandwich<br>Gp41 α9 | β-sandwich-MDD association | Mostly conserved |
| Hydrophobic interaction | Leu 86<br>Val 84<br>Val 242<br>Val 580 | Gp120 β0c<br>Gp120 β7<br>Gp41 α10 | β-sandwich-MDD association | Some of these residues are highly conserved. |
| Hydrophobic interaction | Val 89<br>Pro 238<br>Leu 556<br>Ile 559 | Gp120 β1<br>Gp120 β6<br>Gp41 α9 | β-sandwich-MDD association | Well conserved |
| Hydrophobic interaction | Pro 43<br>Val 496<br>Pro 498<br>Met 530<br>Ala 532<br>Met 535 | Gp120 N-terminus<br>Gp120 C-terminus<br>Gp41 α8 | Protection and sequestration of gp41 fusion helix | Most of these residues are highly conserved. |
| Hydrophobic interaction | Val 31<br>Ile 515<br>Val 518<br>Phe 519 | Gp120 C1<br>Gp41 α7 | Protection and sequestration of gp41 fusion helix | Conserved |
| Hydrophobic interaction | Val 505<br>Val 506<br>Leu 520<br>Leu 523<br>Trp 666<br>Leu 669<br>Phe 673<br>Val 539<br>Leu 543 | Gp120 α6<br>Gp41 α7<br>Gp41 α15<br>Gp41 α8 | Protection and sequestration of gp41 fusion helix | Most of these residues are highly conserved. |
| Hydrophobic interaction | Val 36<br>Val 38<br>Ile 595 | Gp120 β0a<br>Gp41 β26 | Protection and sequestration of gp41 fusion helix | Next to the fusion helix |
| Hydrophobic interaction | Ile 34<br>Trp 610 | Gp120 C1<br>Gp41 ℒH | Protection and sequestration of gp41 fusion helix | Next to the fusion helix |
| Hydrophobic interaction; π-π interaction | Trp 35<br>Phe 522<br>Trp 596<br>Trp 672 | Gp120 C1<br>Gp41 α7<br>Gp41 β26<br>Gp41 α15 | Protection and sequestration of gp41 fusion helix | Trp 35 and Phe 522 assume π-π interaction |
| Hydrogen bond | Glu 32<br>Ser 668 | Gp120 C1<br>Gp41 α15 | Protection and sequestration of gp41 fusion helix | |
| Hydrogen bond network | Thr 90<br>Gln 563 | Gp120 β7<br>Gp41 α9 | β-sandwich-MDD association | Additional hydrogen bonds form between Thr 90 and β7 main-chain |
| Hydrogen bond network | His 92<br>Thr 90<br>Glu 560 | Gp120 β7<br>Gp41 α9 | β-sandwich-MDD association | |
| Hydrogen bond network | Thr 244<br>Glu 246<br>Gln 567 | Gp120 β7<br>Gp41 α9 | β-sandwich-MDD association | Extensive hydrogen bonds form between side-chain and main-chain |

TABLE 4

| PIV/Clade | Virus Isolate | Accession Number |
|---|---|---|
| HIV-1 B | B.US.HXB2 | K03455.1 (REGION: 6225..8795) and AAB50262.1 |

HIV-1 B (B.US.HXB2) cDNA Sequence (SEQ ID NO: 1)

```
   1  atgagagtga aggagaaata tcagcacttg tggagatggg ggtggagatg gggcaccatg
  61  ctccttggga tgttgatgat ctgtagtgct acagaaaaat tgtgggtcac agtctattat
 121  ggggtacctg tgtggaagga agcaaccacc actctatttt gtgcatcaga tgctaaagca
 181  tatgatacag aggtacataa tgtttgggcc acacatgcct gtgtacccac agaccccaac
 241  ccacaagaag tagtattggt aaatgtgaca gaaaatttta acatgtggaa aaatgacatg
 301  gtagaacaga tgcatgagga tataatcagt ttatgggatc aaagcctaaa gccatgtgta
 361  aaattaaccc cactctgtgt tagtttaaag tgcactgatt tgaagaatga tactaatacc
 421  aatagtagta gcgggagaat gataatggag aaaggagaga taaaaaactg ctctttcaat
 481  atcagcacaa gcataagagg taaggtgcag aaagaatatg cattttttta taaacttgat
 541  ataataccaa tagataatga tactaccagc tataagttga caagttgtaa cacctcagtc
 601  attacacagg cctgtccaaa ggtatccttt gagccaattc ccatacatta ttgtgccccg
 661  gctggttttg cgattctaaa atgtaataat aagacgttca atggaacagg accatgtaca
 721  aatgtcagca cagtacaatg tacacatgga attaggccag tagtatcaac tcaactgctg
 781  ttaaatggca gtctagcaga agaagaggta gtaattagat ctgtcaattt cacggacaat
 841  gctaaaacca taatagtaca gctgaacaca tctgtagaaa ttaattgtac aagacccaac
 901  aacaatacaa gaaaaagaat ccgtatccag agaggaccag ggagagcatt tgttacaata
 961  ggaaaaatag gaaatatgag acaagcacat tgtaacatta gtagagcaaa atggaataac
1021  actttaaaac agatagctag caaattaaga gaacaatttg gaaataataa aacaataatc
1081  tttaagcaat cctcaggagg ggacccagaa attgtaacgc acagttttaa ttgtggaggg
1141  gaattttttct actgtaattc aacacaactg tttaatagta cttggtttaa tagtacttgg
1201  agtactgaag ggtcaaataa cactgaagga agtgacacaa tcaccctccc atgcagaata
1261  aaacaaatta taaacatgtg gcagaaagta ggaaaagcaa tgtatgcccc tcccatcagt
1321  ggacaaatta gatgttcatc aaatattaca gggctgctat taacaagaga tggtggtaat
1381  agcaacaatg agtccgagat cttcagacct ggaggaggag atatgaggga caattggaga
1441  agtgaattat ataaatataa agtagtaaaa attgaaccat taggagtagc acccaccaag
1501  gcaaagagaa gagtggtgca gagagaaaaa agagcagtgg gaataggagc tttgttcctt
1561  gggttcttgg gagcagcagg aagcactatg ggcgcagcct caatgacgct gacggtacag
1621  gccagacaat tattgtctgg tatagtgcag cagcagaaca atttgctgag ggctattgag
1681  gcgcaacagc atctgttgca actcacagtc tggggcatca agcagctcca ggcaagaatc
1741  ctggctgtgg aaagatacct aaaggatcaa cagctcctgg gatttggggg ttgctctgga
1801  aaactcattt gcaccactgc tgtgccttgg aatgctagtt ggagtaataa atctctggaa
1861  cagatttgga atcacacgac ctggatggag tgggacagag aaattaacaa ttacacaagc
1921  ttaatacact ccttaattga agaatcgcaa aaccagcaag aaaagaatga acaagaatta
1981  ttggaattag ataaatgggc aagtttgtgg aattggttta cataacaaa ttggctgtgg
2041  tatataaaat tattcataat gatagtagga ggcttggtag gtttaagaat agttttgct
2101  gtactttcta tagtgaatag agttaggcag ggatattcac cattatcgtt tcagacccac
2161  ctcccaaccc cgaggggacc cgacaggccc gaaggaatag aagaagaagg tggagagaga
2221  gacagagaca gatccattcg attagtgaac ggatccttgg cacttatctg ggacgatctg
```

TABLE 4-continued

```
2281        cggagcctgt gcctcttcag ctaccaccgc ttgagagact tactcttgat tgtaacgagg
2341        attgtggaac ttctgggacg caggggggtgg aagccctca aatattggtg gaatctccta
2401        cagtattgga gtcaggaact aaagaatagt gctgttagct tgctcaatgc cacagccata
2461        gcagtagctg aggggacaga taggggttata aagtagtac aaggagcttg tagagctatt
2521        cgccacatac ctagaagaat aagacagggc ttggaaagga ttttgctata a
```

HIV-1 B (B.US.HXB2) Amino Acid Sequence (SEQ ID NO: 2)
```
  1         mrvkekyqhl wrwgwrwgtm llgmlmicsa teklwvtvyy gvpvwkeatt tlfcasdaka
 61         ydtevhnvwa thacvptdpn pqevvlvnvt enfnmwkndm veqmhediis lwdqslkpcv
121         kltplcvslk ctdlkndtnt nsssgrmime kgeikncsfn istsirgkvq keyaffykld
181         iipidndtts ykltscntsv itqacpkvsf epipihycap agfailkcnn ktfngtgpct
241         nvstvqcthg irpvvstqll lngslaeeev virsvnftdn aktiivqlnt sveinctrpn
301         nntrkririq rgpgrafvti gkignmrqah cnisrakwnn tlkqiasklr eqfgnnktii
361         fkqssggdpe ivthsfncgg effycnstql fnstwfnstw stegsnnteg sdtitlperi
421         kqiinmwqkv gkamyappis gqircssnit glllltrdggn snneseifrp gggdmrdnwr
481         selykykvvk ieplgvaptk akrrvvqrek ravgigalfl gflgaagstm gaasmtltvq
541         arqllsgivq qqnnllraie aqqhllqltv wgikqlqari laverylkdq qllgiwgcsg
601         klicttavpw naswsnksle qiwnhttwme wdreinnyts lihslieesq nqqekneqel
661         leldkwaslw nwfnitnwlw yiklfimivg glvglrivfa vlsivnrvrq gysplsfqth
721         lptprgpdrp egieeegger drdrsirlvn gslaliwddl rslclfsyhr lrdlllivtr
781         ivellgrrgw ealkywwnll qywsgelkns aysllnatai avaegtdrvi evvggacrai
841         rhiprrirqg lerill
```

| HIV-1 B | B.US.JR-FL | U63632.1 (REGION: 5541..8084) and AAB05604.1 |

HIV-1 B B.US.JR-FL cDNA Sequence (SEQ ID NO: 3)
```
  1         atgagagtga aggggatcag gaagagttat cagtacttgt ggaaggggg caccttgctc
 61         cttgggatat taatgatctg tagtgctgta gaaaagttgt gggtcacagt ctattatggg
121         gtacctgtgt ggaaagaagc aaccaccact ctattttgtg catcagatgc taaagcatat
181         gatacagagg tacataatgt ttgggccaca catgcctgtg tacccacaga ccccaaccca
241         caagaagtag tattggaaaa tgtaacagaa cattttaaca tgtggaaaaa taacatggta
301         gaacagatgc aggaggatat aatcagttta tgggatcaaa gcctaaagcc atgtgtaaaa
361         ttaaccccac tctgtgttac tttaaattgc aaggatgtga atgctactaa taccactaat
421         gatagcgagg gaacgatgga gaggagaa ataaaaaact gctctttcaa tatcaccaca
481         agcataagag atgaggtgca gaaagaatat gctctttttt ataaacttga tgtagtacca
541         atagataata ataataccag ctataggttg ataagttgta cacctcagt cattacacag
601         gcctgtccaa agatatcctt tgagccaatt cccatacatt attgtgcccc ggctggtttt
661         gcgattctaa gtgtaatga taagacgttc aatggaaaag gaccatgtaa aaatgtcagc
721         acagtacaat gtacacatgg aattaggcca gtagtatcaa ctcaactgct gctaaatggc
781         agtctagcag aagaagaggt agtaattaga tctgacaatt tcacgaacaa tgctaaaacc
841         ataatagtac agctgaaaga atctgtagaa attaattgta caagacccaa caacaataca
901         agaaaaagta tacatatagg accagggaga gcattttata ctacaggaga aataatagga
961         gatataagac aagcacattg taacattagt agagcaaaat ggaatgacac tttaaaacag
```

TABLE 4-continued

```
1021    atagttataa aattaagaga acaatttgag aataaaacaa tagtctttaa tcactcctca
1081    ggaggggacc cagaaattgt aatgcacagt tttaattgtg gaggagaatt tttctactgt
1141    aattcaacac aactgtttaa tagtacttgg aataataata ctgaagggtc aaataacact
1201    gaaggaaata ctatcacact cccatgcaga ataaaacaaa ttataaacat gtggcaggaa
1261    gtaggaaaag caatgtatgc ccctcccatc agaggacaaa ttagatgttc atcaaatatt
1321    acagggctgc tattaacaag atggtggt attaatgaga atgggaccga gatcttcaga
1381    cctggaggag agatatgag ggacaattgg agaagtgaat tatataaata taaagtagta
1441    aaaattgaac cattaggagt agcacccacc aaggcaaaga agagtggt gcaagagaa
1501    aaaagagcag tgggaatagg agctgtgttc cttgggttct gggagcagc aggaagcact
1561    atgggcgcag cgtcaatgac actgacggta caggccagac tattattgtc tggtatagtg
1621    caacagcaga acaatttgct gagggctatt gaggcgcaac agcgtatgtt gcaactcaca
1681    gtctggggca tcaagcagct ccaggcaaga gtcctggctg tggaaagata cctaggggat
1741    caacagctcc tggggatttg gggttgctct ggaaaactca tttgcaccac tgctgtgcct
1801    tggaatgcta gttggagtaa taaatctctg ataggatttt ggaataacat gacctggatg
1861    gagtgggaaa gagaaattga caattacaca agcgaaatat acaccctaat tgaagaatcg
1921    cagaaccaac aagaaaagaa tgaacaagaa ttattggaat tagataaatg gcaagtttg
1981    tggaattggt ttgacataac aaaatggctg tggtatataa aaatattcat aatgatagta
2041    ggaggcttag taggtttaag actagttttt actgtacttt ctatagtgaa tagagttagg
2101    cagggatact caccattatc gtttcagacc ctcctcccag ccccgagggg acccgacagg
2161    cccgaaggaa tcgaagaaga aggtggagag agagacagag acagatccgg acgattagtg
2221    aacggattct tagcacttat ctgggtcgac ctgcggagcc tgtgcctctt cagctaccac
2281    cgcttgagag acttactctt gactgtaacg aggattgtgg aacttctggg acgcaggggg
2341    tgggaagtcc tgaaatattg gtggaatctc ctacagtatt ggagtcagga actaaagaat
2401    agtgctgtta gcttgctcaa tgccacagcc atagcagtag ctgaggggac agataggatt
2461    atagaagcat tacaaagaac ttatagagct attctccaca tacctacaag aataagacag
2521    ggcttggaaa gggctttgct ataa
```

HIV-1 B B.US.JR-FL Amino Acid Sequence (SEQ ID NO: 4)

```
  1    mrvkgirksy qylwkggtll lgilmicsav eklwvtvyyg vpvwkeattt lfcasdakay
 61    dtevhnvwat hacvptdpnp qevvlenvte hfnmwknnmv eqmqediisl wdqslkpcvk
121    ltplcvtlnc kdvnatnttn dsegtmerge ikncsfnitt sirdevqkey alfykldvvp
181    idnnntsyrl iscdtsvitq acpkisfepi pihycapagf ailkcndktf ngkgpcknvs
241    tvqcthgirp vvstqlllng slaeeevvir sdnftnnakt iivqlkesve inctrpnnnt
301    rksihigpgr afyttgeiig dirqahcnis rakwndtlkq iviklreqfe nktivfnhss
361    ggdpeivmhs fncggeffyc nstqlfnstw nnntegsnnt egntitlper ikqiinmwqe
421    vgkamyappi rgqircssni tgllltrdgg inengteifr pgggdmrdnw rselykyvv
481    kieplgvapt kakrrvvqre kravgigavf lgflgaagst mgaasmtltv qarlllsgiv
541    qqqnnllrai eaqqrmlqlt vwgikqlqar vlaveryldg qqllgiwgcs gklicttavp
601    wnaswsnksl driwnnmtwm ewereidnyt seiytliees qnqqekneqe lleldkwasl
661    wnwfditkwl wyikifimiv gglvglrlvf tvlsivnrvr qgysplsfqt llpaprgpdr
```

TABLE 4-continued

| | |
|---|---|
| 721 | pegieeegge rdrdrsgrlv ngflaliwvd lrslclfsyh rlrdllltvt rivellgrrg |
| 781 | wevlkywwnl lqywsqelkn saysllnata iavaegtdri iealqrtyra ilhiptrirq |
| 841 | glerall |

HIV-1 A    A2.CD.97.97CDKS10    AF286241.1 (REGION: 2347..4932) and AAK67312.1

HIV-1 A A2.CD.97.97CDKS10 cDNA Sequence (SEQ ID NO: 5)

| | |
|---|---|
| 1 | atgagagtga tggggacaca gacgagttat cagcacttgt ggagatgggg aatcttaatt |
| 61 | ttgggatgc taataatttg taaagctaca gattggtggg tcacagtata ctatggagta |
| 121 | cctgtgtgga agatgcaga aaccaccta ttttgcgcat cagatgataa agcatatgag |
| 181 | acagaagcgc ataatgtctg ggccacacat gcctgtgtac ccacagaccc caacccacaa |
| 241 | gaagtaaacc taaaaaatgt gacagaagat tttaacatgt ggaaaaataa tatggtagag |
| 301 | cagatgcatg aagatataat cagtctatgg gatcaaagcc taaagccatg tgtaaaatta |
| 361 | acccctctct gtgtcacgtt aaactgtagc aatgccaaca ccaatagcac aatagcact |
| 421 | agcgcccta gcatgggccc tggagaaata aaaaactgtt cttttaatgt taccacagaa |
| 481 | gtaagagata agaaaagaa agtctatgca ctgttttata aacttgatgt agtacaaatt |
| 541 | aatgaaagtg acagtaatag tacaaaggat agtactcagt atagactaat aaattgtaat |
| 601 | acctcagcca tcacacaggc ttgtccaaag gtatcctttg agccaattcc tatacattat |
| 661 | tgtgccccag ctggttttgc gattctaaag tgtgaggatc cgagattcaa tggaacagga |
| 721 | ccatgcaata atgttagctc agtacaatgt acacatggaa ttatgccagt agcatcaact |
| 781 | caactgctgt tgaatggcag tctagcagaa aaagaggtga tgattagatc tgaaaatatt |
| 841 | acaaacaatg ccaaaaacat aatagtacag tttaatgaat cggtaccaat tacttgtatc |
| 901 | agacccaaca acaatacgag aaaaggtata cctattggac caggacaagt cttctataca |
| 961 | agtgacataa taggggatat aagacaagca tattgtagta tcaacaaaac aaaatgggat |
| 1021 | gcctctttac aaaaggtagc tgaacaatta agaaaacact ccctaataa aacaataaat |
| 1081 | tttaccaaac cctcaggagg ggatctagaa attacaacac atagttttaa ttgtggagga |
| 1141 | gaattttct attgtaatac aacaagcctg tttaatagca catggaagaa tggcgccacc |
| 1201 | atacaggaga atagcacgga gacaaatgga attatgactc tcccatgcag aataaaacaa |
| 1261 | attgtagaca tgtggcagga agtaggacaa gcaatgtatg cccctcccat tgcaggagta |
| 1321 | atatattgta catcaaacat tacaggaata atattgcaa gagatggtgg gagcagtaac |
| 1381 | accaatagtg agatctttag gcctggagga ggagatatga gggacaattg gagaagtgaa |
| 1441 | ttatataagt ataaagtagt aaaaattgaa ccactaggag tagcaccctc cagggcaaag |
| 1501 | agaagagtgg tggagagaga aaaaagagca gtgggaatag gagctgtttt ccttgggttc |
| 1561 | ttgggagctg caggaagcac tatgggcgcg gcgtcaataa cgctgacggt acaggccaga |
| 1621 | cagttattat ctggcatagt gcaacagcaa agcaatttgc tgaaggctat agaggctcaa |
| 1681 | cagcatctgt tgaaactcac agtctggggc attaaacagc tccaggcaag agtcctggct |
| 1741 | ctggagagat acctacaaga tcaacagctc ctgggaattt ggggttgctc tggaaaactc |
| 1801 | atctgcacca ctactgtgcc ctggaactct agttggagta ataagactta cgaggagatt |
| 1861 | tggaacaaca tgacctggtt gcaatgggat agagaaattg acaattacac aaatataata |
| 1921 | tacaatctac ttgaagaatc gcagaaccag caggaaaaga tgaacaaga cttactggca |
| 1981 | ttagataaat gggcaagttt gtggaattgg tttagcataa caaactggct gtggtatata |
| 2041 | agaatattca taatgatagt aggaggcttg ataggattaa gaatagttat ggctataatt |

TABLE 4-continued

```
2101    tctgtagtga atagagttag gcagggatac tcacctttgt catttcagat ccctacccca
2161    aacccagagg gtctcgacag gcacggaaga atcgaagaag gaggtggaga gcaagacaga
2221    accagatcga ttcgattagt gagcggattc ttgggacttg cctgggacga cctacggagc
2281    ctgtgcctct tcagctacca ccgattgaga gattgcatct tgattgtagc gaggactgtg
2341    gaacttctgg gacacagcag tctcaaggga ctgagactgg ggtgggaggg cctcaaatat
2401    ttggggaacc ttctactgta ttgggtcgg gaattgaaaa atagtgctat tagtttacta
2461    aattccacag caatagcagt agctgagtgg acagataggg ttatagaaat aggacaaaga
2521    gcttgcagag ctattctcaa catacctaga agaatcagac agggcttcga aagagcttta
2581    ctataa
```

HIV-1 A A2.CD.97.97CDKS10 Amino Acid Sequence (SEQ ID NO: 6)
```
1       mrvmgtqtsy qhlwrwgill lgmliickat dwwvtvyygv pvwkdaettl fcasddkaye
61      teahnvwath acvptdpnpq evnlknvted fnmwknnmve qmhedlislw dqslkpcvkl
121     tplcvtlncs nantnstnst sapsmgpgei kncsfnvtte vrdkekkvya lfykldvvql
181     nesdsnstkd stqyrlincn tsaitqacpk vsfepipihy capagfailk cedprfngtg
241     pcnnvssvqc thgimpvast qlllngslae kevmirseni tnnakniivq fnesvpitci
301     rpnnntrkgi pigpgqvfyt sdligdirqa ycsinktkwd aslqkvaeql rkhfpnktin
361     ftkpsggdle itthsfncgg effycnttsl fnstwkngat igenstetng imtlperikq
421     lvdmwqevgq amyappiagv iyctsnitgi iltrdggssn tnseifrpgg gdmrdnwrse
481     lykykvvkie plgvapsrak rrvverekra vgigavflgf lgaagstmga asitltvgar
541     qllsgivqqq snllkaleaq qhllkltvwg ikqlqarvla leryldqql lgiwgcsgkl
601     ictttvpwns swsnktyeei wnnmtwlqwd reidnytnii ynlleesqnq qekneqdlla
661     ldkwaslwnw fsitnwlwyi rifimivggl iglrivmaii svvnrvrqgy splsfqiptp
721     npeglrdhgr leegggeqdr trsirlvsgf lglawddlrs lclfsyhrlr dciliivartv
781     ellghsslkg lrlgweglky lgnllllywgr elknsaisll nstaiavaew tdrvielgqr
841     acrailnipr rirqgferal l
```

| HIV-1 C | C.ZM.02.02ZM109 | AY424138.2 and AAR09542.2 |
|---|---|---|

HIV-1 C C.ZM.02.02ZM109 cDNA Sequence (SEQ ID NO: 7)
```
1       atgagagtga agggatatt gaggaattgt caacaatggt ggatatgggg catcttaggc
61      ttttggatgc taatgatttg taatgtggtg ggaaacttgt gggtcacagt ctattatggg
121     gtacctgtgt ggaagaagc aaaaactact ctattctgtg catcagatgc taaatcatat
181     gagagagaag tgcataatgt atgggctaca catgcctgtg tacccacaga ccccgaccca
241     caagaactgg ttatggcaaa tgtaacagaa aattttaaca tgtggaaaaa tgacatggta
301     gatcagatgc atgaggatat aatcagttta tgggatcaaa gcctaaagcc atgtgtaaaa
361     ttgaccccac tctgtgtcac tttaaattgt acaagtcctg ctgcccacaa tgagagcgag
421     acaagagtaa acattgctc tttcaatata accacagatg taaagatag aaaacagaag
481     gtgaatgcaa ctttttatga ccttgatata gtaccactta gcagctctga caactctagc
541     aactctagtc tgtatagatt aataagttgt aatacctcaa ccataacaca gcctgtcca
601     aaggtctctt ttgacccaat tcctatacat tattgtgctc cagctggtta tgcgattcta
661     aaatgtaata ataagacatt cagtgggaaa ggaccatgtt ctaatgtcag tacagtacaa
721     tgtacacatg gaattaggcc agtggtatca actcaactgc tgttaaatgg tagcctagca
```

TABLE 4-continued

```
 781    gaagaagaga tagtaattag atctgaaaat ctgacagaca atgccaaaac aataatagta
 841    catcttaata aatctgtaga aattgagtgt ataagacctg caataatac  aagaaaaagt
 901    ataaggctag gaccaggaca acattctat  gcaacagggg atgtaatagg agacataaga
 961    aaggcatatt gtaaaattaa tggaagtgag tggaatgaaa ctttaacaaa agtaagtgaa
1021    aaattaaaag aatattttaa taaaacaata gatttgccc  agcactcggg aggggaccta
1081    gaagtgacaa cacatagctt taattgtaga ggagaattt  tctattgcaa tacatcagaa
1141    ctatttaata gtaatgcaac agaaagcaac atcacactcc catgcagaat aaaacaaatt
1201    ataaacatgt ggcagggggt aggacgagca atgtatgccc ctcccatcag aggagaaata
1261    aaatgtacat caaatatcac aggactacta ttaacacgcg atggaggcaa caacaataat
1321    tcaacagagg agatattcag acctgaagga ggaaatatga gggacaattg gagaagtgaa
1381    ttatacaaat ataaagtggt ggagattaag ccattgggaa tagcacccac tgaggcaaaa
1441    aggagagtgg tgcagagaga aaaaagagca gtgggaatag gagctgtgtt ccttgggttc
1501    ttgggagcag caggaagcac tatgggcgcg gcgtcaataa cgctgacggt acaggccaga
1561    caattattgt ctggtatagt gcaacagcaa agcaatttgc tgagggctat agaggcgcaa
1621    caacatctgt tgcaactcac agtctggggc attaagcagc tccaggcaag agtcctggct
1681    atagaaagat acctacagga tcaacagctc ctagggattt gggctgctc  tggaaaactc
1741    atctgcacca ctgcagtgcc ttggaactcc agttggagta ataaatctaa ggaagaaatt
1801    tggggcaaca tgacctggat gcagtgggat aaagaagtta gtaattacac attcacaata
1861    taccagttgc ttgaagaatc gcaataccag caggaacaaa atgaaaaaga actattagca
1921    ttgaacaagt ggaatgatct gtggagttgg tttaacataa caaattggtt gtggtatata
1981    aaatattca  taatgatagt aggaggctta ataggtttaa gaataatttt tgctgtactt
2041    tccatagtga atagagttag gcaggatac  tcaccttgt  cgtttcagac ccttaccccg
2101    aacccagggg gacccgacag gctcggaaga atcgaaggag aaggtggaga gcaagacaaa
2161    aacagatcca ttcgattagt gaacggattc ttagctctta tctgggacga cctgtggagc
2221    ctgtgccgct tcagctacca cctattgaga gacttcatat tgattgtagc gagagcggtg
2281    gaacttctgg gacgcagcag tctcaaggga ctacagaggg ggtgggaagc tcttaaatat
2341    ctgggaaatc ttatgcagta ttggggtctg gaactaaaaa gaagtgctat taatctgtta
2401    gatacaacag cagtagcagt agctgaagga acagatagga ttatagaatt agcacaaggc
2461    atttatagag ctatctgcaa cataccacta agaataagac agggctttga agcagcttta
2521    caataa
```

HIV-1 C C.ZM.02.02ZM109 Amino Acid Sequence (SEQ ID NO: 8)
```
  1    mrvkgilrnc qqwwiwgilg fwmlmicnvv gnlwvtvyyg vpvwkeaktt lfcasdaksy
 61    erevhnvwat hacvptdpdp qelvmanvte nfnmwkndmv dqmhediisl wdqslkpcvk
121    ltplcvtlnc tspaahnese trvkhcsfni ttdvkdrkqk vnatfydldi vplsssdnss
181    nsslyrlisc ntstitqacp kvsfdpipih ycapagyail kcnnktfsgk gpcsnvstvq
241    cthgirpvvs tqlllngsla eeeivirsen ltdnaktiiv hlnksveiec irpgnntrks
301    irlgpgqtfy atgdvigdir kayckingse wnetltkvse klkeyfnkti rfaqhsggdl
361    evtthsfncr geffycntse lfnsnatesn itlperikqi inmwqgvgra myappirgei
421    kctsnitgll ltrdggnnnn steeifrpeg gnmrdnwrse lykykvveik plgiapteak
481    rrvvqrekra vgigavflgf lgaagstmga asitltvgar qllsgivqqq snllraieaq
541    qhllqltvwg ikqlqarvla ierylqdqql lgiwgcsgkl icttavpwns swsnkskeei
```

TABLE 4-continued

```
601    wgnmtwmqwd kevsnytfti yqlleesqyq qeqnekella lnkwndlwsw fnitnwlwyi
661    kifimivggl iglriifavl sivnrvrqgy splsfqtltp npggpdrlgr iegeggeqdk
721    nrsirlvngf laliwddlws lcrfsyhllr dfilivarav ellgrsslkg lqrgwealky
781    lgnlmqywgl elkrsainll dttavavaeg tdriielaqg iyraicnipr rirqgfeaal
841    q
```

| HIV-1 O | O.BE.87.ANT70 | L20587.1 (REGION: 6273..8864) and AAA99883.1 |
|---|---|---|

HIV-1 O O.BE.87.ANT70 cDNA Acid Sequence (SEQ ID NO: 9)
```
   1    atgatagtga ctatgaaagc aatggagaag aggaacaaga agttatggac cttgtactta
  61    gccatggctt gataaccccc atgtttgagc cttagacagc tatatgcaac agtctatgct
 121    ggggtgcctg tatgggaaga tgcaacacca gtactattct gtgcttcaga tgctaaccta
 181    acaagcactg aaaagcataa tatttgggca tcacaagcct gtgttcctac agaccccact
 241    ccatatgaat atccattgca caatgtgaca gatgacttta atatatggaa aattacatg
 301    gtagaacaaa tgcaggaaga cattattagt ttatgggacc agagtcttaa accttgtgtt
 361    caaatgactt tcctgtgtgt acaatggag tgtacaaaca tagctggaac aacaaatgaa
 421    aaccttatga agaagtgtga gtttaatgta accactgtta tcaaagacaa aaaggagaaa
 481    aaacaggctc tattctatgt atcagatttg atggaactga atgagacaag cagcacaaat
 541    aagacaaaca gcaaaatgta tacattaact aattgtaact ccacaaccat cacgcaagcc
 601    tgtccaaagg tatcttttga accaattcca atacactatt gtgctccagc aggatatgct
 661    atctttaagt gtaacagcac agaatttaat ggaacaggca catgcagaaa cataacggta
 721    gttacttgta cacatggcat taggccaaca gtaagtactc agctaatatt aaatgggaca
 781    ctctctaaag gaaaaataag aatgatggca aagatattt tggaaggtgg aaaaaatatc
 841    atagtgaccc taaactctac cctaaacatg acctgtgaaa gaccacaaat agacatacaa
 901    gagatgagaa taggtccaat ggcctggtac agcatgggaa taggggaac agcaggaaac
 961    agctcaaggg cagcttattg caagtataat gccactgatt ggggaaaaat attaaaacaa
1021    acagctgaaa ggtatttaga actagtaaac aatacaggta gtattaacat gacattcaat
1081    cacagcagcg gtggagatct agaggtaacc catttacact taactgtca tggagaattc
1141    ttttattgta acacagctaa gatgtttaat tataccttt catgtaacgg aaccacctgt
1201    agtgttagta atgttagtca aggtaacaat ggcactctac cttgcaaact gagacaggtg
1261    gtaaggtcat ggataagggg acagtcggga ctctatgcac ctcccatcaa aggtaatcta
1321    acatgtatgt caaacataac tggaatgatc ctacaaatgg ataacacatg gaacagcagc
1381    aacaacaatg taacatttag accaataggg ggagacatga agatatatg gagaactgaa
1441    ttgttcaact acaaagtagt aagggtaaaa ccttttagtt tggcacccac acgtattgca
1501    aggccagtca taagcactag aactcataga gaaaaaagag cagtaggatt gggaatgcta
1561    ttcttgggg ttctaagtgc agcaggtagc actatgggcg cagcggcaac aacgctggcg
1621    gtacagaccc acactttgct gaagggtata gtgcaacagc aggacaacct gctaagagca
1681    atacaggccc agcagcaatt gctgaggcta tctrtatggg gtatcagaca actccgagct
1741    cgcctgctag ccttagaaac cttactacag aatcagcaac tcctaagcct atggggctgt
1801    aaaggaaagc tagtctgcta cacatcagta aaatggaata gaacatggat aggaaacgaa
1861    agcatttggg acaccttaac atggcaggaa tgggatcgg agataagcaa cataagctcc
1921    accatatatg aggaaataca aaggcacaa gtacagcagg aacaaaatga gaaaagttg
```

TABLE 4-continued

```
1981    ctggagttag atgaatgggc ctctatttgg aattggcttg acataactaa atggttgtgg
2041    tatataaaaa tagcaataat catagtagga gcactagtag gggtgagagt tatcatgata
2101    gtacttaata tagtgaaaaa cattaggcag ggatatcaac ccctctcgtt acagatcccc
2161    aaccatcacc aagaggaagc aggaacgcca ggaagaacag gaggaggagg tggagaagaa
2221    ggcaggccca ggtggatacc ctcgccgcaa gggttcttgc cactgttgta cacggacctc
2281    agaacaataa tattgtggac ttaccacctc ttgagcaact tagcatcagg gatccagaag
2341    gtgatcagct atctgaggct tggactgtgg atcctagggc agaagataat taatgtttgc
2401    agaatttgtg cagctgtaac acaatactgg ctacaagaat tgcagaatag tgctacaagc
2461    ttgctagaca cacttgcagt ggcagtagcc aattggactg acggcataat cgcagggata
2521    caaagaatag gaacaggaat tcgtaacatc ccaaggagaa ttagacaggg cttagaaaga
2581    agtttattgt aa
```

HIV-1 O O.BE.87.ANT70 Amino Acid Sequence (SEQ ID NO: 10)
```
  1     mivtmkamek rnkklwtlyl amalitpcls lrqlyatvya gvpvwedatp vlfcasdanl
 61     tstekhniwa sqacvptdpt pyeyplhnvt ddfniwknym veqmqediis lwdqslkpcv
121     qmtflcvqme ctniagttne nlmkkcefnv ttvikdkkek kqalfyvsdl melnetsstn
181     ktnskmytlt ncnsttitqa cpkvsfepip ihycapagya ifkcnstefn gtgtcrnitv
241     vtcthgirpt vstqlilngt lskgkirmma kdileggkni ivtlnstlnm tcerpqidiq
301     emrigpmawy smgiggtagn ssraayckyn atdwgkilkq taerylelvn ntgsinmtfn
361     hssggdlevt hlhfnchgef fycntakmfn ytfscngttc sysnvsqgnn gtlpcklrqv
421     vrswirgqsg lyappikgnl tcmsnitgml lqmdntwnss nnnvtfrpig gdmkdiwrte
481     lfnykvvrvk pfsvaptria rpvistrthr ekravglgml flgvlsaags tmgaaattla
541     vqthtllkgi vqqqdnllra lqaqqqllrl sxwgirqlra rllaletllq nqqllslwgc
601     kgklvcytsv kwnrtwigne siwdtltwqe wdrqlsniss tlyeelqkaq vqqeqnekkl
661     leldewasiw nwlditkwlw yikiaiiivg alvgvrvimi vinivknirq gyqplslqip
721     nhhqeeagtp grtgggggee grprwipspq gflpllytdl rtiilwtyhl lsnlasgiqk
781     visylrlglw ilgqklinvc ricaavtqyw lqelqnsats lldtlavava nwtdgiiagi
841     qrigtgirni prrirqgler sll
```

| SIVcpz | CPZ.CD.90.ANT | U42720.2 (REGION: 5678..8254) and AAB47730.2 |

SIVcpz CPZ.CD.90.ANT cDNA Acid Sequence (SEQ ID NO: 11)
```
  1     atgaggaagc cgatacatat tatttggggt ctggctttgc taatccagtt tatagagaag
 61     gggacgaatg aagactatgt aacagtattc tatggagtcc ctgtctggag aaatgcgaca
121     cctactctat tttgtgccac aaatgcctcc atgacaagta cagaggtgca caatgtatgg
181     gcaactacca gttgtgtgcc aatagatcca gatcctattg tagttaggct caatacctca
241     gtctggttta atgcttataa aaattatatg gtagaaagta tgacagaaga tatgntacaa
301     ttattccaac aaagccataa gccatgtgta aaactaacac ctatgtgtat aaaaatgaat
361     tgtacaggat acaatggaac acctacaaca ccaagtacaa caacaagtac agtaacacca
421     aagacaacaa caccaatagt agatggcatg aagctacaag aatgtaactt aatcagagc
481     acaggattta agataagaa acaaaaaatg aaagccatat tttataaagg agatcttatg
541     aagtgtcagg acaacaatga gactaactgc tattacttat ggcactgcaa caccacaact
601     atcacacaat cctgtgaaaa gtctactttt gaaccaattc ctatacatta ttgtgctcca
```

TABLE 4-continued

```
 661    gcaggatatg ctatattgag atgtgaagat gaggatttta caggagtagg gatgtgtaaa
 721    aatgtctcag tagtacattg cactcatgga ataagcccaa tggtggcaac atggttacta
 781    ttaaatggaa cttaccaaac aaacacttca gtagtaatga atggtcgcaa aaatgaatct
 841    gtgcttgtaa gatttggaaa agaattcgaa aacttaacaa ttacatgtat aagaccagga
 901    aataggacag taagaaatct acaaatagga ccaggaatga ctttctataa cgtagaaata
 961    gcaacaggag acactaggaa agcgttctgt acagtcaata agacgctatg gaacaagca
1021    cgtaacaaaa cagagcacgt tcttgcggag cattggaaaa agtagacaa caaaaccaat
1081    gcgaaaacaa tatggacatt ccaagatgga gatcctgaag taaaagtgca ttggtttaat
1141    tgccaaggag aattctttta ttgtgatata cacccttggt tcaatgccac atacacggga
1201    aacctcatca caaacggagc cctcatagca cattgcagaa ttaagcagat agttaatcat
1261    tggggcatag tttcaaaagg catttactta gcccctagga gagggaatgt ttcctgtact
1321    tccagcataa ctggaattat gttggaaggt caaatatata atgaaactgt taaagtgtca
1381    cctgctgcaa gagtagcaga ccaatggaga gcggagttgt ccaggtacca ggtggtagag
1441    attgrtccct tgtcagtagc cccaacaaca ggnaaaaggc cagaaataaa acaacactcc
1501    agacaaaaaa gaggcattgg aatagggctg ttcttcttgg gtcttctcag tgcagctggc
1561    agtacaatgg gcgcagcgtc aatagcgctg acggcacaga ccaggaattt gytccatggt
1621    attgtacaac agcaggccaa tctgctgcaa gccatagaga cacagcaaca tctgctacag
1681    ctctcggtct ggggagtaaa acaactccag gcaagaatgc ttgcagtcga gaagtaccta
1741    agagatcaac aactattgag cctctggggt tgtgctgaca aggtgacctg tcacactacg
1801    gtgccttgga ataattcctg ggtaaacttc acgcaaacat gtgcaaagaa cagcagtgat
1861    atacaatgta tttgggaaaa tatgacatgg caagaatggg acagattagt acagaattca
1921    acaggacaga tatataatat cttacaaata gcacatgagc aacaagagag aaataaaaag
1981    gaattatatg aactagacaa atggagctca ttatggaatt ggtttgacat aacacaatgg
2041    ctatggtata taaaaatatt tattatgata gtaggagcta ttgtaggact aagaattttg
2101    cttgtattag ttagttgctt aagaaaggtt aggcaggat atcatcctct gtcatttcag
2161    atccctaccc aaaaccagca ggatccagag cagccagaag aaataagaga agaaggtgga
2221    agaaaagaca ggatcaggtg gagggccttg cagcacgggt tcttcgcact cttgtgggtg
2281    gacctgacga gcataatcca gtggatctac cagatctgca gaacctgtct cttgaacctt
2341    tgggcagtcc tccaacacct ctgcagaatt actttcgac tgtgcaacca tctggagaac
2401    aatctcagca ccctctggac aataatcaga actgagatca ttaagaacat tgacagactt
2461    gctatttggg tagggggaaaa aacagatagc atacttctag ctctccaaac tatagtcaga
2521    atcataaggg aagtacctag cgcatcaga caagggttgg aaattgcatt aaattaa
```

SIVcpz CPZ.CD.90.ANT Amino Acid Sequence (SEQ ID NO: 12)

```
  1    mrkpihiiwg lalliqfiek gtnedyvtvf ygvpvwrnat ptlfcatnas mtstevhnvw
 61    attscvpidp dpivvrints vwfnayknym vesmtedmxq lfqqshkpcv kltpmcikmn
121    ctgyngtptt pstttstvtp ktttpivdgm klqecnfnqs tgfkdkkqkm kaifykgdlm
181    kcqdnnetnc yylwhcnttt itqscekstf epipihycap agyailrced edftgvgmck
241    nvsvvhcthg ispmvatwll lngtyqtnts vvmngrknes vlvrfgkefe nititcirpg
301    nrtvrnlqig pgmtfynvei atgdtrkafc tvnktlweqa rnktehvlae hwkkvdnktn
361    aktiwtfqdg dpevkvhwfn cqgeffycdi tpwfnatytg nlitngalia hcrikqivnh
421    wgivskgiyl aprrgnvsct ssitgimleg qiynetvkvs paarvadqwr aelsryqvve
```

TABLE 4-continued

| | |
|---|---|
| 481 | ixplsvaptt gkrpeikqhs rqkrgigigl fflgllsaag stmgaasial taqtrnlxhg |
| 541 | ivqqqanllq aietqqhllq lsvwgvkqlq armlavekyl rdqqllslwg cadkvtchtt |
| 601 | vpwnnswvnf tqtcaknssd iqciwenmtw qewdrlvqns tgqiynilqi aheqqernkk |
| 661 | elyeldkwss lwnwfditqw lwyikifimi vgaivglril lvlvsclrkv rqgyhplsfq |
| 721 | iptqnqqdpe qpeeireegg rkdrirwral qhgffallwv dltsliqwly qicrtcllnl |
| 781 | wavlqhlcri tfrlcnhlen nlstlwtiir teiiknidrl aiwvgektds illalgtivr |
| 841 | iirevprrir ggleialn |

| HIV-2 | H2A.GW.x.ALI | AF082339.1 (REGION: 6694..9282) and AAC95347.1 |
|---|---|---|

HIV-2 H2A.GW.x.ALI cDNA Acid Sequence (SEQ ID NO: 13)

| | |
|---|---|
| 1 | atgatgtcta gtagaaatca gctgcttgtt actatcttac tagctagtgc ttgcttagta |
| 61 | tattgtaaac aatatgtgac tgttttttat ggcgtgccag catggaaaaa tgcatccatt |
| 121 | cccctctttt gtgcaaccaa aaatagagat acttggggaa ccatacagtg cttaccagac |
| 181 | aatgatgatt atcaggaaat gctttgaat gtgacagagg ctttcgatgc atgggataat |
| 241 | acagtaacag aacaagcagt agaagatgtc tggagactat tgagacatc aataaaacca |
| 301 | tgtgtcaagt taacaccttt atgtatagca atgaagtgta gcaacataag cacagagagc |
| 361 | acaaccacat ccccgagccc agggagcaca ctcaaacccc tgataaatga gagcgatcca |
| 421 | tgcataaagg cagacaactg ccccagggga ctaggggatg aagagatggt caattgtcgg |
| 481 | ttcaacatga caggattaca gagagataag ccaaaacagt ataatgaaac atggtactca |
| 541 | aaagatgtgg tttgtgaacc atttaacacc accacaaacc agaccaggtg ttacatgaac |
| 601 | cattgcaaca catcagtcat cacagagtca tgtgataagc actattggga tgctataagg |
| 661 | tttagatact gtgcaccacc tggttacgcc ctactaagat gcgatgatat caattattca |
| 721 | ggctttgcac ccaattgctc taaagtagta gctgctacat gcacaaggat gatggagacg |
| 781 | caaacttcta cttggtttgg ctttaatggc actagggcag aaaatagaac atatatctat |
| 841 | tggcatggta gagataatag aactatcatc agcttaaaca acattataa tcttactatg |
| 901 | cattgtaaga ggccaggaaa taagacagtt gtaccaataa cacttatgtc agggttaata |
| 961 | tttcactccc agccaatcaa taaagaccc agacaagcat ggtgctggtt caaggcgaa |
| 1021 | tggaggaaag ccatgcagga ggtgaaggaa acccttgtaa acatcccag gtataaagga |
| 1081 | accaatgaca caaaccaaat taactttaca aaaccaggaa gaggctcaga tgcagaagtg |
| 1141 | gtatatatgt ggactaactg cagaggagaa tttctccatt gcaacatgac ttggttcctc |
| 1201 | aattgggtgg aaaacaaaac gggtcaggaa cagcacaatt atgcaccgtg ccatataaag |
| 1261 | caaataatta atctggca caaagcaggg aaaaatgtat atttgcctcc tagggaagga |
| 1321 | gagttgacct gcaactcaac agtaaccagc ttgattgcta acattgacac ggatggcaac |
| 1381 | cagacaaata ttaccttag tgcagaggtg gcagaactat accgattaga attgggggat |
| 1441 | tataaattag tagagataac accaattggc ttcgcaccta catcagaaag gagatactcc |
| 1501 | tctactccaa ggaggaataa aagaggtgtg ttcgtgctag gttcttagg ttttctcgcg |
| 1561 | acagcaggtt ctgcaatggg cacggcagct taacgctgt ctgctcagtc tcggactta |
| 1621 | ttggccggga tagtgcagca acagcaacag ctgttggacg tggtcaagag acaacaggaa |
| 1681 | atgttgcgac tgaccgtctg ggaacgaaa atctccagg caagagtcac tgctatcgag |
| 1741 | aaatacttaa aggaccaggc gcggctaaat tcatggggat gtgcatttag acaagtctgc |
| 1801 | cacactactg taccatgggt aaataactcc ttaaaaacctg attgggacaa catgacgtgg |

TABLE 4-continued

```
1861    caagagtggg aacaacaagt ccgttaccta gaggcaaata tcagtgaaca gttagaacgg
1921    gcacaaattc agcaagaaaa gaatacgtat gaactacaaa aattaaatag ctgggatgtt
1981    tttaccaact ggcttgactt aaccgcctgg gtcaagtata ttcaatatgg agtttatata
2041    atagtaggaa tagtagctct tagaatagta atatatgtag tgcaaatgtt aagtagactc
2101    aggaagggct ataggcctgt tttctcctcc cctcccggtt acatccaaca gatccatatc
2161    cacaaggacc aggaacagcc aaccagagga gaaacagaag aagacgttgg agacaacgtt
2221    ggggacagat tgtggccctg gccgatcgca tatttacatt tcctgatcca cctgctagct
2281    cgcctcttga tcgggctgta cagcatctgc agggacttac tatccaggat ctccccgatc
2341    ctccaaccga tcttccggag tcttcagaga gcgctgacaa caatcaggga ctggctgaga
2401    cttaaagcag cctacctgca gtatgggtgc gagtggatcc aagaagcgtt ccgggccttt
2461    gcaaggattg cgagagagac tcttacaaac acctggagag acttgtgggg ggcagtgcag
2521    tgggtcggga ggaggatact cgcagtccca aggaggatca ggcaggggc agaaattgcc
2581    ctcctgtga
```

HIV-2 H2A.GW.x.ALI Amino Acid Sequence (SEQ ID NO: 14)
```
  1     mmssrnqllv tillasaclv yckqyvtvfy gvpawknasi plfcatknrd twgtiqclpd
 61     nddyqeialn vteafdawdn tvtegavedv wrlfetsikp cvkltplcia mkcsnistes
121     tttspspgst lkplinesdp cikadncprg lgdeemvncr fnmtglqrdk pkqynetwys
181     kdvvcepfnt ttnqtrcymn hcntsvites cdkhywdair frycappgya llrcddinys
241     gfapncskvv aatctrmmet qtstwfgfng traenrtyiy whgrdnrtii slnkhynitm
301     hckrpgnktv vpitlmsgli fhsqpinkrp rqawcwfkge wrkamqevke tivkhprykg
361     tndtnqinft kpgrgsdaev vymwtncrge flhcnmtwfl nwvenktgqe qhnyapchik
421     qiiniwhkag knvylppreg eltcnstvts lianidtdgn qtnitfsaev aelyrlelgd
481     yklveitpig faptserrys stprrnkrgv fvlgflgfla tagsamgtaa ltlsaqsrtl
541     lagivqqqqq lldvvkrqqe mlrltvwgtk nlqarvtaie kylkdqarin swgcafrqvc
601     httvpwvnns lkpdwdnmtw qeweqqvryl eaniseqler aqiqqeknty elqklnswdv
661     ftnwldltaw vkyiqygvyi ivgivalriv iyvvqmlsrl rkgyrpvfss ppgyiqqihi
721     hkdqeqptrg eteedvgdnv gdrlwpwpia ylhflihlla rlliglysic rdllsrispi
781     lqpifrslqr alttirdwlr lkaaylqygc ewiqeafraf ariaretltn twrdlwgavq
841     wvgrrilavp rrirqgaeia ll
```

| SIVmac | MAC.US.x.239 | M33262.1 (REGION: 6860..9499) and AAA47637.1 |

SIVmac MAC.US.x.239 cDNA Acid Sequence (SEQ ID NO: 15)
```
  1     atgggatgtc ttgggaatca gctgcttatc gccatcttgc ttttaagtgt ctatgggatc
 61     tattgtactc tatatgtcac agtctttat ggtgtaccag cttggaggaa tgcgacaatt
121     ccctctttt gtgcaaccaa gaatagggat acttggggaa caactcagtg cctaccagat
181     aatggtgatt attcagaagt ggcccttaat gttacagaaa gctttgatgc ctggaataat
241     acagtcacag aacaggcaat agaggatgta tggcaactct tgagacctc aataaagcct
301     tgtgtaaaat atccccatt atgcattact atgagatgca ataaaagtga cagataga
361     tgggggattga caaaatcaat aacaacaaca gcatcaacaa catcaacgac agcatcagca
421     aaagtagaca tggtcaatga gactagttct tgtatagccc aggataattg cacaggcttg
481     gaacaagagc aaatgataag ctgtaaattc aacatgacag ggttaaaaag agacaagaaa
```

TABLE 4-continued

```
541   aaagagtaca atgaaacttg gtactctgca gatttggtat gtgaacaagg gaataacact
601   ggtaatgaaa gtagatgtta catgaaccac tgtaacactt ctgttatcca agagtcttgt
661   gacaaacatt attgggatgc tattagattt aggtattgtg cacctccagg ttatgctttg
721   cttagatgta atgcacacaaa ttattcaggc tttatgccta aatgttctaa ggtggtggtc
781   tcttcatgca aaggatgat ggagacacag acttctactt ggtttggctt aatggaact
841   agagcagaaa atagaactta tatttactgg catggtaggg ataataggac tataattagt
901   ttaaataagt attataatct aacaatgaaa tgtagaagac caggaaataa gacagtttta
961   ccagtcacca ttatgtctgg attggttttc cactcacaac caatcaatga taggccaaag
1021  caggcatggt gttggtttgg aggaaaatgg aaggatgcaa taaaagaggt gaagcagacc
1081  attgtcaaac atcccaggta tactgaaact aacaatactg ataaaatcaa tttgacggct
1141  cctggaggag gagatccgga agttaccttc atgtggacaa attgcagagg agagttcctc
1201  tactgtaaaa tgaattggtt tctaaattgg gtagaagata ggaatacagc taaccagaag
1261  ccaaaggaac agcataaaag gaattacgtg ccatgtcata ttagacaaat aatcaacact
1321  tggcataaag taggcaaaaa tgtttatttg cctccaagag agggagacct cacgtgtaac
1381  tccacagtga ccagtctcat agcaaacata gattggattg atggaaacca aactaatatc
1441  accatgagtg cagaggtggc agaactgtat cgattggaat tgggagatta taaattagta
1501  gagatcactc caattggctt ggcccccaca gatgtgaaga ggtacactac tggtggcacc
1561  tcaagaaata aaagaggggt ctttgtgcta gggttcttgg gttttctcgc aacggcaggt
1621  tctgcaatgg gcgcggcgtc gttgacgctg accgctcagt cccgaacttt attggctggg
1681  atagtgcagc aacagcaaca gctgttggac gtggtcaaga caacaagaa attgttgcga
1741  ctgaccgtct ggggaacaaa gaacctccag actagggtca ctgccatcga gaagtactta
1801  aaggaccagg cgcagctgaa tgcttgggga tgtgcgttta gacaagtctg ccacactact
1861  gtaccatggc caaatgcaag tctaacacca aagtggaaca atgagacttg gcaagagtgg
1921  gagcgaaagg ttgacttctt ggaagaaaat ataacagccc cctagagga ggcacaaatt
1981  caacaagaga agaacatgta tgaattacaa aagttgaata gctgggatgt gtttggcaat
2041  tggtttgacc ttgcttcttg gataaagtat atacaatatg gagtttatat agttgtagga
2101  gtaatactgt taagaatagt gatctatata gtacaaatgc tagctaagtt aaggcagggg
2161  tataggccag tgttctcttc cccacccctct tatttccagc agacccatat ccaacaggac
2221  ccggcactgc caaccagaga aggcaaagaa agagacggtg agaaggcgg tggcaacagc
2281  tcctggcctt ggcagataga atatattcat ttcctgatcc gccaactgat acgcctcttg
2341  acttggctat tcagcaactg cagaaccttg ctatcgagag tataccagat cctccaacca
2401  atactccaga ggctctctgc gaccctacag aggattcgag aagtcctcag gactgaactg
2461  acctacctac aatatgggtg gagctatttc catgaggcgg tccaggccgt ctggagatct
2521  gcgacagaga ctcttgcggg cgcgtgggga gacttatggg agactcttag gagaggtgga
2581  agatggatac tcgcaatccc caggaggatt agacaagggc ttgagctcac tctcttgtga
```

SIVmac MAC.US.x.239 Amino Acid Sequence (SEQ ID NO: 16)
```
  1   mgclgnqlli ailllsvygi yctlyvtvfy gvpawrnati plfcatknrd twgttqclpd
 61   ngdysevaln vtesfdawnn tvteqaledv wqlfetsikp cvklsplcit mrcnksetdr
121   wgltksittt asttsttasa kvdmvnetss claqdnctgl eqeqmisckf nmtglkrdkk
181   keynetwysa dlvceqgnnt gnesrcymnh cntsviqesc dkhywdairf rycappgyal
241   lrcndtnysg fmpkcskvvv ssctrmmetq tstwfgfngt raenrtyiyw hgrdnrtiis
```

TABLE 4-continued

| | |
|---|---|
| 301 | lnkyynitmk crrpgnktvl pvtimsglvf hsqpindrpk qawcwfggkw kdalkevkqt |
| 361 | ivkhprytgt nntdkinita pgggdpevtf mwtncrgefl yckmnwflnw vedrntanqk |
| 421 | pkeqhkrnyv pchirqiint whkvgknvyl ppregdltcn stvtsliani dwidgnqtni |
| 481 | tmsaevaely rlelgdyklv eitpiglapt dvkryttggt srnkrgvfvl gflgflatag |
| 541 | samgaasltl taqsrtllag ivqqqqllld vvkrqqellr ltvwgtknlq trvtaiekyl |
| 601 | kdqaqlnawg cafrqvchtt vpwpnasltp kwnnetwqew erkvdfleen italleeaqi |
| 661 | qqeknmyelq klnswdvfgn wfdlaswiky iqygvylvvg villriviyi vqmlaklrqg |
| 721 | yrpvfsspps yfqqthiqqd palptregke rdggegggns swpwqleylh flirglirll |
| 781 | twlfsncrtl lsrvyqilqp ilqrlsatlq rirevlrtel tylqygwsyf heavgavwrs |
| 841 | atetlagawg dlwetlrrgg rwilaiprri rqgleltll |

| SIVsmm | SMM.US.x.PT573 | AY221511.1 (REGION: 646..3309) and AAO67291.1 |
|---|---|---|

SIVsmm SMM.US.x.PT573 cDNA Acid Sequence (SEQ ID NO: 17)

| | |
|---|---|
| 1 | atgggatgtc ttgggaatca gctgcttatc gcgctcttgc tagtaagtgt tttagagatt |
| 61 | tgttgtgttc aatatgtaac agtattctat ggtgtaccag catggaagaa tgcgacaatt |
| 121 | cccctcttct gtgcaaccag gaatagggac acttggggaa caacacaatg cttgcctgat |
| 181 | aatgatgatt actcagaatt ggcagtcaat atcacagagg cttttgatgc ttggaataat |
| 241 | acagtcacag aacaagcaat agaggatgtg tggaacctct tgaaacatc cattaagccc |
| 301 | tgtgtaaaac ttaccccact atgtatagca atgaggtgta ataaaactga dacagatagg |
| 361 | tggggtttga caggaagagc agagacaaca caacagcga atcaacaac atcaacaaca |
| 421 | acaacaacag taacaccaaa ggtcataaat gaaggtgatt cttgcataaa agataatagt |
| 481 | tgtgcaggct tggaacagga gcccatgata ggttgtaaat ttaacatgac aggattaaag |
| 541 | agggacaaaa agatagaata taatgaaaca tggtattcaa gagatttaat ctgtgagcag |
| 601 | tcagcaaatg aagtgagag taaatgttac atgcagcatt gtaacaccag tgttattcag |
| 661 | gaatcctgtg acaagcatta ttgggatgct attagattta gatactgtgc accgccaggt |
| 721 | tatgctttgc ttaggtgtaa tgattcaaat tattcaggct tgctcctaa atgttctaag |
| 781 | gtagtggttt cttcatgcac aagaatgatg agacgcaaa cctctacttg gtttggcttc |
| 841 | aatggtacta gggcagaaaa tagaacatac atttattggc atggcaatag taatagaacc |
| 901 | ataattagct taaataagta ttataatcta acaataagat gtaaaagacc aggaaataag |
| 961 | acagttttac cagtcaccat tatgtcaggg ttggtcttcc attcgcaaac cataaatacg |
| 1021 | agaccaaaac aggcctggtg ctggtttgaa ggaaactgga caaggccat ccaggaagtg |
| 1081 | aaggaaacct tggtcaaaca tcccaggtat acgggaacta atgatactag gaaaattaat |
| 1141 | ctaacagctc cagcaagagg aaatccagaa gtcactttta tgtggacaaa ttgtcgagga |
| 1201 | gaattcttat actgcaaaat gaattggttt ctcaattggg tagaggacag agaccaaat |
| 1261 | agtaacagat ggaaacaaca aaaggagtca gagcaaaaga agagaaatta tgtgccatgt |
| 1321 | catattagac aaataatcaa cgcgtggcac aaagtaggca aaaatgtata tttgcctcct |
| 1381 | agggaaggag acctgacatg taattccact gtaactagtc tcatagcaaa gatagattgg |
| 1441 | atcaataaca tgagaccaa atcaccatg agtgcagagg tggcagaact gtatcgattg |
| 1501 | gagttgggag attacaaatt agtagagatt actccaattg gcttggcccc cacaaatgta |
| 1561 | agaagtaca ccacaactgg tgcctcaaga aataagagag gggtctttgt gctagggttc |
| 1621 | ttgggttttc tcgcgacagc aggttctgca atgggcgcgg cgtcgctgac gctgtcggct |

TABLE 4-continued

```
1681    cagtcccgga ctttgttggc tgggatagtg cagcaacagc aacagctgtt ggatgtggtc
1741    aagagacaac aagaattgtt gcgactgacc gtctggggaa ctaagaacct ccagactaga
1801    gtcactgcta tcgagaagta cctgaaggat caggcgcggc taaattcatg gggatgtgct
1861    tttaggcaag tctgtcacac tactgtacca tggccaaatg actcattggt gcctaattgg
1921    gacaatatga cttggcaaga gtgggaagga aaggttaact tcctagaggc aaatataact
1981    caattattag aagaagcaca aattcagcaa gaaagaata tgtatgaatt gcaaaaacta
2041    aatagctggg atatctttgg caattggttt gaccttactt cttggataag atatatacaa
2101    tatggtgtac taatagtttt aggagtagta gggttaagaa tagtgatata tgtagtgcaa
2161    atgctagcta ggttaagaca gggttatagg ccagtgttct cttcccctcc cgcttatgtt
2221    cagcagatcc ctatccacaa ggaccaggaa ccgccaacca agaaggaga agaaggagaa
2281    ggtggagaca gaggtggcag cagatcttgg ccttggcaga tagaatatat tcatttccta
2341    atccgccaac tgatacgcct cttgacttgg ctattcagca gctgcaggga ttggctattg
2401    aggatctacc agatcctcca accagtgctc cagagactct caaggacgct gcaaagagtt
2461    cgtgaagtca tcagaattga ataacctac ctacaacatg ggtggagcta tttccaagaa
2521    gcagcacagg cgtggtggaa atttgcgcga gagactcttg cgagcgcgtg gagagacata
2581    tgggagactc tgggaagggt tggaagaggg atactcgcaa tccctaggcg cgtcaggcaa
2641    gggcttgagc tcactctctt gtga
```

SIVsmm SMM.US.x.PT573 Amino Acid Sequence (SEQ ID NO: 18)
```
  1    mgclgnqlli alllvsvlei ccvqyvtvfy gvpawknati plfcatrnrd twgttqclpd
 61    nddyselavn iteafdawnn tvtegaiedv wnlfetsikp cvkltplcia mrcnktetdr
121    wgltgraett ttaksttstt tttvtpkvin egdscikdns cagleqepmi gckfnmtglk
181    rdkkieynet wysrdliceq sangseskcy mqhcntsviq escdkhywda irfrycappg
241    yallrcndsn ysgfapkcsk vvvssctrmm etqtstwfgf ngtraenrty iywhgnsnrt
301    iislnkyynl tirckrpgnk tvlpvtimsg lvfhsqtint rpkqawcwfe gnwskaiqev
361    ketivkhpry tgtndtrkin ltapargnpe vtfmwtncrg eflyckmnwf lnwvedrdqn
421    snrwkqqkes eqkkrnyvpc hirqiinawh kvgknvylpp regdltcnst vtsliakidw
481    innnetnitm saevaelyrl elgdyklvei tpiglaptnv rrytttgasr nkrgvfvlgf
541    lgflatagsa mgaasltlsa qsrtllagiv qqqqqlldvv krqqellrlt vwgtknlqtr
601    vtaiekylkd qarinswgca frqvchttvp wpndslvpnw dnmtwqeweg kvnfleanit
661    qlleeaqiqq eknmyelqkl nswdifgnwf dltswiryiq ygvlivlgvv glriviyvvq
721    mlarlrqgyr pvfssppayv qqipihkdqe pptkegeege ggdrggsrsw pwqieyihfl
781    irqlirlltw lfsscrdwll riyqilqpvl qrlsrtlqry revirieity lqhgwsyfqe
841    aaqawwkfar etlasawrdi wetlgrvgrg ilaiprrvrq gleltll
```

TABLE 5

List of interprotomer and intersubunit contacts within the HIV-1 Env trimer*

| | Residue 1 [atom(s)] | Distance (Å) | Residue 2 [atom(s)] | Predicted Bond in wild-type Env |
|---|---|---|---|---|
| 1 | ASP 185[OD1/OD2] | 3.69/2.69 | ARG 192[NH1] | Salt bridge |
| 2 | ASP 185[OD1] | 3.28 | SER 195[N] | Hydrogen bonds |
| 3 | ASP 185[OD1] | 3.26 | ILE 194[N] | Hydrogen bonds |
| 4 | HIS 92 [NE2] | 3.27 | GLU 560[OE2] | Salt bridge |

TABLE 5-continued

List of interprotomer and intersubunit contacts within the HIV-1 Env trimer*

| | Residue 1 [atom(s)] | Distance (Å) | Residue 2 [atom(s)] | Predicted Bond in wild-type Env |
|---|---|---|---|---|
| 5 | ARG 503[NH1/2] | 3.17/2.51 | GLU 654[OE1/2] | Salt bridge |
| 6 | GLU 91 [OE1] | 2.86/2.62 | ARG 557[NH1] | Salt bridge |
| 7 | GLU 509[OE1] | 3.19 | ARG 542[NE] | Salt bridge |
| 8 | LYS 510[NZ] | 3.41 | GLU 662[OE2] | Salt bridge |
| 9 | LYS 510[NZ] | 2.83 | GLU 659[OE1] | Salt bridge |
| 10 | SER 511[O] | 2.25 | ALA 512[N] | Salt bridge |
| 11 | VAL 38[N] | 2.73 | TRP 596[O] | Hydrogen bonds |
| 12 | TYR 39[N] | 2.89 | TRP 596[O] | Hydrogen bonds |
| 13 | GLN 82[NE2] | 3.03 | TRP 571[O] | Hydrogen bonds |
| 14 | GLN 246[NE2] | 3.52 | THR 569[O] | Hydrogen bonds |
| 15 | LYS 500[NZ] | 2.80 | ALA 532[O] | Hydrogen bonds |
| 16 | LYS 502[NZ] | 3.45 | GLY 527[O] | Hydrogen bonds |
| 17 | ARG 503[NH2] | 2.51 | GLU 654[OE2] | Hydrogen bonds |
| 18 | GLU 32[OE1] | 2.61 | SER 668[OG] | Hydrogen bonds |
| 19 | VAL 36[O] | 2.83 | TRP 596[N] | Hydrogen bonds |
| 20 | TYR 40[O] | 3.62 | TYR 586[OH] | Hydrogen bonds |
| 21 | VAL 44[O] | 3.30 | THR 569[OG1] | Hydrogen bonds |
| 22 | GLU 47[O] | 2.81 | TRP 571[NE1] | Hydrogen bonds |
| 23 | GLU 87[OE2] | 2.91 | GLN 577[NE2] | Hydrogen bonds |
| 24 | ASN 88[O] | 3.69 | GLN 563[NE2] | Hydrogen bonds |
| 25 | VAL 89[O] | 3.36 | GLN 563[NE2] | Hydrogen bonds |
| 26 | GLU 91[OE2] | 2.62 | ARG 557[NH2] | Hydrogen bonds |
| 27 | THR 244[OG1] | 2.66 | GLN 567[NE2] | Hydrogen bonds |
| 28 | GLN 246[OE1] | 3.61 | GLY 572[N] | Hydrogen bonds |
| 29 | GLN 246[OE1] | 2.61 | TRP 571[N] | Hydrogen bonds |
| 30 | LYS 490[O] | 3.47 | ARG 564[NH2] | Hydrogen bonds |
| 31 | LYS 502[O] | 3.02 | GLN 652[NE2] | Hydrogen bonds |
| 32 | SER 508[O] | 3.53 | ALA 512[N] | Hydrogen bonds |
| 33 | GLU 509[OE1] | 3.19 | ARG 542[NH2] | Hydrogen bonds |
| 34 | GLU 509[O] | 2.79 | ALA 512[N] | Hydrogen bonds |
| 35 | GLU 632[OE1] | 3.60 | ARG 633[NH1] | Salt bridge |
| 36 | GLU 647[OE1/OE2] | 3.48/2.53 | LYS 601[NZ] | Salt bridge |
| 37 | ARG 707[NH2] | 2.13 | SER 703[OG] | Hydrogen bonds |
| 38 | GLU 641[OE2] | 2.12 | SER 599[OG] | Hydrogen bonds |
| 39 | LEU 645[O] | 2.94 | LEU 602[N] | Hydrogen bonds |
| 40 | LEU 697[O] | 3.78 | ARG 696[NH2] | Hydrogen bonds |
| 41 | THR 700 [OG1] | 2.70 | ARG 696 [NH2] | Hydrogen bonds |
| 42 | ILE 184 | 2.89 | LEU 193 | Hydrophobic |
| 43 | PRO 183 | 4.69 | ILE 194 | Hydrophobic |
| 44 | LEU 34 | 4.07 | TRP 610 | Hydrophobic |
| 45 | TRP 35 | 2.98 | TRP 596 | Hydrophobic |
| 46 | TRP 35 | 3.32 | PHE 522 | Hydrophobic |
| 47 | VAL 44 | 4.68 | ILE 573 | Hydrophobic |
| 48 | VAL 44 | 3.22 | LEU 576 | Hydrophobic |
| 49 | VAL 38 | 3.76 | LEU 595 | Hydrophobic |
| 50 | LEU 86 | 3.74 | VAL 580 | Hydrophobic |
| 51 | ILE 491 | 3.23 | LEU 568 | Hydrophobic |
| 52 | PRO 493 | 3.39 | LEU 568 | Hydrophobic |
| 53 | ALA 221 | 3.55 | VAL 570 | Hydrophobic |
| 54 | LEU 602 | 3.84 | LEU 645 | Hydrophobic |
| 55 | ILE 603 | 4.63 | LEU 645 | Hydrophobic |
| 56 | LEU 602 | 6.41 | ILE 646 | Hydrophobic |
| 57 | TRP 628 | 3.22 | PHE 685 | Hydrophobic |
| 58 | TRP 628 | 3.73 | VAL 689 | Hydrophobic |
| 59 | PHE 699 | 3.82 | ILE 704 | Hydrophobic |

TABLE 6

List of interprotomer bonds useful for increasing the stability of Env trimmers

| Env Residues* | Region | $C_\beta - C_\beta$ Distance (Å) | Preferred Mutations |
|---|---|---|---|
| Ile 184 - Leu 193 | TAD TABLE 6-continued List of interprotomer bonds useful for increasing the stability of Env trimmers

| Env Residues* | Region | $C_\beta$ - $C_\beta$ Distance (Å) | Preferred Mutations |
|---|---|---|---|
| Asn 185 - Ser 195 | TAD - TAD | 6-7 | Cys-Cys substitution |
| Ile 184 - Arg 192 | TAD - TAD | 6-7 | Cys-Cys substitution |
| Ile 184 - Ile 194 | TAD - TAD | 6-7 | Cys-Cys substitution |
| Pro 183 - Arg 192 | TAD - TAD | 6-7 | Cys-Cys substitution |
| Val 182 - Arg 192 | TAD - TAD | 6-7 | Cys-Cys substitution |
| Val 182 - Ile 194 | TAD - TAD | 6-7 | Cys-Cys substitution |
| Val 181 - Ile 194 | TAD - TAD | 6-7 | Cys-Cys substitution |
| Val 182 - Leu 193 | TAD - TAD | 6.25 | 182 Lys-193 Asp<br>182 Arg-193 Asp |
| Gly 600 - Thr 644 | MPD - MPD | 6.05 ($C_\alpha$-$C_\alpha$)<br>5.46 ($C_\alpha$-$C_\beta$) | Cys-Cys substitution |
| Ser 599 - Thr 644 | MPD - MPD | 5.83 | Cys-Cys substitution |
| Ser 599 - Glu 641 | MPD - MPD | 6.31 | Ser 599Lys (salt bridge) |
| Ser 599 - Glu 641 | MPD - MPD | 6.31 | Ser 599Arg (salt bridge) |
| Ser 599 - Thr 644 | MPD - MPD | 5.83 | Ser 599Arg + Thr 644Glu (double salt bridge between 599 and 641 and 644) |
| Leu 602 - Leu 645 | MPD - MPD | 6.69<br>4.95 ($C_\alpha$-$C_\alpha$) | Loop rotation can allow disulfide; Cys-Cys substitution |
| Arg 696 - Thr 700 | MID - MID | nh2 of 696 is 2.7 Å away from og1 of 700 | Thr 700Asp can form an intramembrane salt bridge |

*The TAD residues predicted to exhibit the best distances for disulfide bond formation when cysteine substitutions are made are listed. However, due to some structural flexibility in the TAD, other combinations of Cys-Cys substitutions may be effective in forming disulfide bonds between the gp120 residues in Set A (residues 180-186) and Set B (resides 190-195). For example, Table 5 shows that Asp 185 and Arg 192 are in close contact; substitution of cysteine residues for Asp 185 and Arg 192 could stabilize TAD-TAD interactions (and thus stabilize the Env trimer.)

TABLE 7

List of intersubunit residue pairs useful for increasing the stability of Env trimers, especially using disulfide bonds

| gp120 | gp41 | Distance $C_\beta$ - $C_\beta$ (Å) |
|---|---|---|
| Thr 37 | Trp 596 | 3.398 |
| Val 42 | Gln 575 | 4.59 |
| Lys 46 | Val 570 | 4.4 |
| Lys 46 | Trp 571 | 3.96 |
| Ala 48 | Val 570 | 4.88 |
| Glu 82 | Trp 571 | 3.45 |
| Ala 221 | Val 570 | 4.565 |
| Gln 246 | Val 570 | 4.71 |
| Pro 493 | Leu 568 | 4.16 |
| Pro 498 | Ala 532 | 4.91 |
| Lys 500 | Met 535 | 3.62 |
| Lys 500 | Ala 532 | 4.74 |
| Lys 502 | Gln 652 | 4.02 |
| Val 506 | Lys 655 | 4.84 |
| Glu 509 | Ala 512 | 4.71 |
| Glu 509 | Ala 517 | 4.86 |

TABLE 8

List of intrasubunit residue pairs useful for increasing the stability of Env trimers, especially using disulfide bonds or promoting hydrophobic interactions

| Residue 1 | Distance (Å) | Residue 2 | Preferred Mutations |
|---|---|---|---|
| VAL 134 | 3.51 | HIS 308 | |
| ASP 133 | 4.27 | ILE 309 | |
| Glu 150 | 3.57 | ARG 315 | Salt bridge |
| Glu 153 | 2.67 | LYS 305 | Salt bridge |

TABLE 9

List of residues useful for increasing the stability of Env trimers by increasing the solubility of the trimmers

| Residue | Preferred Mutations |
|---|---|
| ILE 684 | Hydrophobic |
| ILE 688 | Hydrophobic |
| LEU 692 | Hydrophobic |
| VAL 698 | Hydrophobic |
| LEU 702 | Hydrophobic |
| VAL 705 | Hydrophobic |

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A stabilized primate immunodeficiency virus (PIV) envelope polypeptide trimer complex, wherein (a) each protomeric unit of the complex comprises a gp120 subunit and a gp41 subunit, or immunogenic fragments thereof, (b) one or more subunits of the complex comprises one or more mutated amino acid residues that increases the stability of the complex, wherein (i) the positions of the one or more mutated residues of the gp120 subunit and/or the gp41 subunit are selected from the group consisting of the residues listed in Tables 6-9 and combinations thereof and (ii) the one or more mutated residues is not at position 535 or 596 of gp41 from HIV-1-JR-FL, and (c) the one or more mutated amino acid residues does not substantially alter the conformation of the native complex, in which the amino acid residues at the positions of the one or more mutated residues are not mutated.

2. The trimeric complex of claim 1, wherein the PIV is simian immunodeficiency virus (SIV), human immunodeficiency virus type 1 (HIV-1), or human immunodeficiency virus type 2 (HIV-2).

3. An isolated polypeptide comprising the amino acid sequences of gp120 and gp41 subunits of a PIV envelope polypeptide, wherein (a) one or more subunits comprises one or more mutated amino acid residues that increases the stability of envelope polypeptide trimer complexes comprising the polypeptide, wherein (i) the positions of the one or more mutated residues of the gp120 subunit and/or the gp41 subunit are selected from the group consisting of the residues listed in Tables 6-9 and combinations thereof and (ii) the one or more mutated residues is not at position 535 or 596 of gp41 from HIV-1-JR-FL, and (b) the one or more mutated amino acid residues does not substantially alter the conformation of the native envelope polypeptide trimer complex, in which the amino acid residues at the positions of the one or more mutated residues are not mutated.

4. The isolated polypeptide comprising the amino acid sequences of gp120 and gp41 subunits of a PIV envelope polypeptide of claim 3, wherein the PIV is SIV, HIV-1, or HIV-2.

5. A method of eliciting an immune response in a subject against a primate immunodeficiency virus comprising administering to the subject a therapeutically effective amount of an agent selected from the group consisting of:
   i) a stabilized primate immunodeficiency virus (PIV) envelope polypeptide trimer complex, wherein (a) each protomeric unit of the complex comprises a gp120 subunit and a gp41 subunit, or immunogenic fragments thereof, (b) one or more subunits of the complex comprises one or more mutated amino acid residues that increases the stability of the complex, wherein (i) the positions of the one or more mutated residues of the gp120 subunit and/or the gp41 subunit are selected from the group consisting of the residues listed in Tables 6-9 and combinations thereof and (ii) the one or more mutated residues is not at position 535 or 596 of gp41 from HIV-1-JR-FL, and (c) the one or more mutated amino acid residues does not substantially alter the conformation of the native complex, in which the amino acid residues at the positions of the one or more mutated residues are not mutated;

ii) an isolated polypeptide comprising the amino acid sequences of gp120 and gp41 subunits of a PIV envelope polypeptide, wherein (a) one or more subunits comprises one or more mutated amino acid residues that increases the stability of envelope polypeptide trimer complexes comprising the polypeptide, wherein (i) the positions of the one or more mutated residues of the gp120 subunit and/or the gp41 subunit are selected from the group consisting of the residues listed in Tables 6-9 and combinations thereof and (ii) the one or more mutated residues is not at position 535 or 596 of gp41 from HIV-1-JR-FL, and (b) the one or more mutated amino acid residues does not substantially alter the conformation of the native complex, in which the amino acid residues at the positions of the one or more mutated residues are not mutated;

iii) an isolated nucleic acid which encodes the polypeptide of ii);

iv) an expression vector comprising the nucleic acid sequence of iii);

v) an isolated host cell comprising the expression vector of iv); and vi) an immunogenic composition comprising the trimeric complex of i) or the polypeptide of ii), and a pharmaceutically acceptable carrier, to thereby elicit the immune response.

6. A method for delaying the onset of, or slowing the rate of progression of, a primate immunodeficiency virus-related disease in a subject infected with a primate immunodeficiency virus, comprising administering to the subject a therapeutically effective amount of an agent selected from the group consisting of:

i) a stabilized primate immunodeficiency virus (PIV) envelope polypeptide trimer complex, wherein (a) each protomeric unit of the complex comprises a gp120 subunit and a gp41 subunit, or immunogenic fragments thereof, (b) one or more subunits of the complex comprises one or more mutated amino acid residues that increases the stability of the complex, wherein (i) the positions of the one or more mutated residues of the gp120 subunit and/or the gp41 subunit are selected from the group consisting of the residues listed in Tables 6-9 and combinations thereof and (ii) the one or more mutated residues is not at position 535 or 596 of gp41 from HIV-1-JR-FL, and (c) the one or more mutated amino acid residues does not substantially alter the conformation of the native complex, in which the amino acid residues at the positions of the one or more mutated residues are not mutated;

ii) an isolated polypeptide comprising the amino acid sequences of gp120 and gp41 subunits of a PIV envelope polypeptide, wherein (a) one or more subunits comprises one or more mutated amino acid residues that increases the stability of envelope polypeptide trimer complexes comprising the polypeptide, wherein (i) the positions of the one or more mutated residues of the gp120 subunit and/or the gp41 subunit are selected from the group consisting of the residues listed in Tables 6-9 and combinations thereof and (ii) the one or more mutated residues is not at position 535 or 596 of gp41 from HIV-1-JR-FL, and (b) the one or more mutated amino acid residues does not substantially alter the conformation of the native complex, in which the amino acid residues at the positions of the one or more mutated residues are not mutated;

iii) an isolated nucleic acid which encodes the polypeptide of ii);

iv) an expression vector comprising the nucleic acid sequence of iii);

v) an isolated host cell comprising the expression vector of iv); and vi) an immunogenic composition comprising the trimeric complex of i) or the polypeptide of ii), and a pharmaceutically acceptable carrier, thereby delaying the onset of, or slowing the rate of progression of, the primate immunodeficiency virus-related disease in the subject.

7. The method of claim 6 wherein the PIV is SIV, HIV-1, or HIV-2.

* * * * *